(12) United States Patent
Zhou et al.

(10) Patent No.: US 11,046,746 B2
(45) Date of Patent: Jun. 29, 2021

(54) METHOD OF TREATMENT OF CEREBRAL AMYLOID ANGIOPATHY WITH P75ECD PEPTIDE AND/OR P75ECD-FC FUSION PROTEIN

(71) Applicant: Suzhou Auzone Biological Technology Co., Ltd, Suzhou (CN)

(72) Inventors: Xinfu Zhou, Adelaide (AU); Yanjiang Wang, Chongqing (CN)

(73) Assignee: SUZHOU AUZONE BIOLOGICAL TECHNOLOGY CO., LTD

(*) Notice: Subject to any disclaimer, the term of this patent is extended or adjusted under 35 U.S.C. 154(b) by 0 days.

(21) Appl. No.: 15/560,944

(22) PCT Filed: Mar. 25, 2016

(86) PCT No.: PCT/CN2016/077412
§ 371 (c)(1),
(2) Date: Sep. 22, 2017

(87) PCT Pub. No.: WO2016/150403
PCT Pub. Date: Sep. 29, 2016

(65) Prior Publication Data
US 2018/0170996 A1 Jun. 21, 2018

(30) Foreign Application Priority Data
Mar. 26, 2015 (AU) .............................. 2015901100

(51) Int. Cl.
| | | |
|---|---|---|
| *C07K 14/705* | (2006.01) | |
| *C07K 14/71* | (2006.01) | |
| *A61P 25/28* | (2006.01) | |
| *A61K 38/00* | (2006.01) | |
| *A61K 38/17* | (2006.01) | |
| *A61K 47/68* | (2017.01) | |
| *C12N 15/86* | (2006.01) | |
| *G01N 33/68* | (2006.01) | |
| *C07K 16/28* | (2006.01) | |
| *A61P 9/10* | (2006.01) | |
| *A61K 39/00* | (2006.01) | |

(52) U.S. Cl.
CPC ...... *C07K 14/70578* (2013.01); *A61K 38/179* (2013.01); *A61K 47/6811* (2017.08); *A61P 9/10* (2018.01); *A61P 25/28* (2018.01); *C07K 14/71* (2013.01); *C07K 16/2878* (2013.01); *C12N 15/86* (2013.01); *G01N 33/6896* (2013.01); *A61K 38/00* (2013.01); *A61K 2039/505* (2013.01); *C07K 2319/30* (2013.01); *C12N 2750/14143* (2013.01); *G01N 2333/71* (2013.01)

(58) Field of Classification Search
CPC .............. C07K 14/70578; C07K 14/71; C07K 16/2878; A61P 9/10; A61P 25/28; A61K 47/68
See application file for complete search history.

(56) References Cited

U.S. PATENT DOCUMENTS

2007/0054848 A1* 3/2007 Tohyama ................ A61P 25/28
514/44 R

FOREIGN PATENT DOCUMENTS

| CN | 101478977 A | 3/2007 |
|---|---|---|
| CN | 102233128 A | 11/2011 |
| CN | 102326083 A | 1/2012 |
| JP | 2008-540445 | 11/2008 |
| JP | 2012-518042 | 8/2012 |
| WO | WO 2007/109851 | 10/2007 |
| WO | 2010096470 A2 | 8/2010 |
| WO | 2012103577 A1 | 8/2012 |

OTHER PUBLICATIONS

Bugiani O. Abeta-related cerebral amyloid angiopathy. Neurol. Sci. 24:S1-S2. (Year: 2004).*
Klohs J et al. Imaging of cerebrovascular pathology in animal models of Alzheimer's disease. Frontiers in Aging Neuroscience, Mar. 13, 2014, 6(32), pp. 1-30. (Year: 2014).*
Shepheard, S.R. et al., "The Extracellular Domain of Neurotrophin Receptor p75 as a Candidate Biomarker for Amyotrophic Lateral Sclerosis", PLOS ONE, vol. 9, No. 1, Jan. 27, 2014, 9 pp., p. e87398.
Jiao, Shusheng et al., "p75NTR-ECD: a novel diagnostic biomarker for AD", China Proceedings of Conference Full-text Database: Proceedings of 17th National Conference of Neurology, Chinese Medical Association, Sep. 19, 2014, p. 453.
Jiao, S.S. et al., "Differential levels of p75NTR ectodomain in CSF and blood in patients with Alzheimer's disease: a novel diagnostic marker", Translational Psychiatry, vol. 5, Oct. 6, 2015, 7 pp., p. c650.
WIPO, International Search Report and Written Opinion for International Application No. PCT/CN2016/077412, dated Jul. 12, 2016.
Changyue Gao, etal.; "The effects of intracerebroventricular administration of p75$^{NTR-ECD}$ DCX expression in the hippocampus and cognitive function changes in Alzheimer's disease mice;" Chin. J. Nerv. Ment. Dis., vol. 36 No. 12; 2010; pp. 723-726. (English Abstract).
Yan-Jiang Wang, et al.; "p75NTR Regulates Aβ Deposition by Increasing Aβ Production But Inhibiting Aβ Aggregation with Its Extracellular Domain;" The Journal of Neuroscience, Feb. 9, 2011; pp. 2291-2304.

(Continued)

Primary Examiner — Kimberly Ballard
(74) Attorney, Agent, or Firm — Haynes and Boone, LLP

(57) ABSTRACT

A method of treating and/or preventing neurological conditions, comprising administering to a subject in need thereof a therapeutically effective amount of a p75 extracellular domain (p75ECD) or a functional fragment, variant, analogue or derivative thereof. Also provided is a method of diagnosing and/or prognosing Alzheimer's disease (AD) in a test subject comprising comparing the concentration of p75ECD and/or p75FL and/or the ratio of p75ECD:p75FL in a biological sample of the test subject to non-demented control subject(s).

4 Claims, 21 Drawing Sheets
Specification includes a Sequence Listing.

(56) References Cited

OTHER PUBLICATIONS

Balu Chakravarthy, et aL; "Hippocampal Membrane-Associated $p75^{NTR}$ Levels are Increased in Alzheimer's Disease;" *Journal of Alzheimer's Disease* 30; 2012; pp. 675-684.

Gong-Ling Hu, et al.; "Extracellular Domain of P75NTR Attenuates Beta-Amyloid-Induced Neurotoxicity and Tau Hyperphosphorylation;" *Alzheimer's & Dementia*, vol. 8, No. 4, Supplement 1, 2012, p. 260, O2-12-04.

Yue-Hui Li, etal.; "A Monoclonal Antibody Against the Extracellular Domain of P75 Neurotrophin Receptor;" *Monoclonal Antibodies in Immunodiagnosis and Immunotherapy*, vol. 32, No. 1, 2013; pp. 55-59.

Yao, X-Q et al.; "p75NTR ectodomain is a physiological neuroprotective molecule against amyloid-beta toxicity in the brain of Alzheimer's disease;" *Molecular Psychiatry* (2015) 20, pp. 1301-1310; published online Apr. 28, 2015.

Wilcock, DM et al., "Passive immunotherapy against Abeta in aged APP-transgenic mice reverses cognitive deficits and depletes parenchymal amyloid deposits in spite of increased vascular amyloid and microhemorrhage," J. Neuroinflammation, (2004) 1(1):24.

Patton, RL et al., "Amyloid-beta peptide remnants in AN-1792-immunized Alzheimer's disease patients: a biochemical analysis," Am. J. Pathol., (2006) 169(3):1048-63.

Liu, YH et al., "Immunotherapy for Alzheimer disease: the challenge of adverse effects," Nat. Rev. Neurol., (2012), 8(8):465-469 (2012).

Wang, Yeran; "The expression of p75NTR in the brain of Alzheimer's disease and interaction sites between p75NTR and Aβ"; Chinese Master's Theses Data (Medicine and Health Sciences), No. 1, 2015 (electronic journal), including a master's thesis dated May 2014.

Chinese Patent Office; CN Office Action and Search Report dated Apr. 26, 2020 (no translation); CN Application No. 2016800008477.

* cited by examiner

SEQUENCE LISTING

```
<160> NUMBER OF SEQ ID NOS: 13

<210> SEQ ID NO 1
<211> LENGTH: 1284
<212> TYPE: DNA
<213> ORGANISM: Homo sapiens

<400> SEQUENCE: 1
atgggggcag gtgccaccgg ccgcgccatg gacgggccgc gcctgctgct gttgctgctt     60
ctgggggtgt cccttggagg tgccaaggag gcatgcccca caggcctgta cacacacagc    120
ggtgagtgct gcaaagcctg caacctgggc gagggtgtgg cccagccttg tggagccaac    180
cagaccgtgt gtgagccctg cctggacagc gtgacgttct ccgacgtggt gagcgcgacc    240
gagccgtgca agccgtgcac cgagtgcgtg gggctccaga gcatgtcggc gccgtgcgtg    300
gaggccgacg acgccgtgtg ccgctgcgcc tacggctact accaggatga gacgactggg    360
cgctgcgagg cgtgccgcgt gtgcgaggcg ggctcgggcc tcgtgttctc ctgccaggac    420
aagcagaaca ccgtgtgcga ggagtgcccc gacggcacgt attccgacga ggccaaccac    480
gtggaccccg gcctgccctg caccgtgtgc gaggacaccg agcgccagct ccgcgagtgc    540
```

```
acacgctggg ccgacgccga gtgcgaggag atccctggcc gttggattac acggtccaca    600
cccccagagg gctcggacag cacagccccc agcacccagg agcctgaggc acctccagaa    660
caagacctca tagccagcac ggtggcaggt gtggtgacca cagtgatggg cagctcccag    720
cccgtggtga cccgaggcac caccgacaac ctcatccctg tctattgctc catcctggct    780
gctgtggttg tgggccttgt ggcctacata gccttcaaga ggtggaacag ctgcaagcag    840
aacaagcaag gagccaacag ccggccagtg aaccagacgc ccccaccaga gggagaaaaa    900
ctccacagcg acagtggcat ctccgtggac agccagagcc tgcatgacca gcagccccac    960
acgcagacag cctcgggcca ggccctcaag ggtgacggag gcctctacag cagcctgccc   1020
ccagccaagc gggaggaggt ggagaagctt ctcaacggct ctgcggggga cacctggcgg   1080
cacctggcgg gcgagctggg ctaccagccc gagcacatag actcctttac ccatgaggcc   1140
tgccccgttc gcgccctgct tgcaagctgg gccacccagg acagcgccac actggacgcc   1200
ctcctggccg ccctgcgccg catccagcga gccgacctcg tggagagtct gtgcagtgag   1260
tccactgcca catccccggt gtga                                          1284
```

<210> SEQ ID NO 2  
<211> LENGTH: 420  
<212> TYPE: PRT  
<213> ORGANISM: Homo sapiens

<400> SEQUENCE: 2

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Glu Gln Asp Leu Ile
    210                 215                 220

Ala Ser Thr Val Ala Gly Val Val Thr Thr Val Met Gly Ser Ser Gln
225                 230                 235                 240
```

```
Pro Val Val Thr Arg Gly Thr Thr Asp Asn Leu Ile Pro Val Tyr Cys
                245                 250                 255

Ser Ile Leu Ala Ala Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Glu Gly Glu Lys Leu His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu
            420

<210> SEQ ID NO 3
<211> LENGTH: 1188
<212> TYPE: DNA
<213> ORGANISM: Homo sapiens

<400> SEQUENCE: 3
aaggaggcat gccccacagg cctgtacaca cacagcggtg agtgctgcaa agcctgcaac      60
ctgggcgagg gtgtggccca gccttgtgga gccaaccaga ccgtgtgtga gccctgcctg     120
gacagcgtga cgttctccga cgtggtgagc gcgaccgagc cgtgcaagcc gtgcaccgag     180 tgcgtgggc tccagagcat gtcggcgccg tgcgtggagg ccgacgacgc cgtgtgccgc     240
tgcgcctacg gctactacca ggatgagacg actgggcgct gcgaggcgtg ccgcgtgtgc     300
gaggcgggct cgggcctcgt gttctcctgc aggacaagc agaacaccgt gtgcgaggag     360
tgccccgacg gcacgtattc cgacgaggcc aaccacgtgg accgtgcct gccctgcacc     420 gtgtgcgagg acaccgagcg ccagctccgc gagtgcacac gctgggccga cgccgagtgc     480
gaggagatcc ctggccgttg gattacagac aaaactcaca catgcccacc gtgcccagca     540
cctgaactcc tggggggacc gtcagtcttc ctcttccccc caaaacccaa ggacaccctc     600
atgatctccc ggacccctga ggtcacatgc gtggtggtgg acgtgagcca cgaagaccct     660
gaggtcaagt tcaactggta cgtggacggc gtggaggtgc ataatgccaa gacaaagccg     720
cgggaggagc agtacaacag cacgtaccgg gtggtcagcg tcctcaccgt cctgcaccag     780
gactggctga atggcaagga gtacaagtgc aaggtctcca acaaagccct cccagccccc     840
atcgagaaaa ccatctccaa agccaagggg cagccccgag aaccacaggt gtacaccctg     900
cccccatccc gggatgagct gaccaagaac caggtcagcc tgacctgcct ggtcaaaggc     960
ttctatccca gcgacatcgc cgtggagtgg gagagcaatg ggcagccgga gaacaactac    1020
```

```
aagaccacgc tcccgtgctg gactccgac ggctccttct tcctctacag caagctcacc      1080
gtggacaaga gcaggtggca gcagggaac gtcttctcat gctccgtgat gcatgaggct      1140
ctgcacaacc actacacgca aagagcctc tccctgtctc cgggtaaa                   1188
```

<210> SEQ ID NO 4
<211> LENGTH: 221
<212> TYPE: PRT
<213> ORGANISM: Homo sapiens

<400> SEQUENCE: 4

```
Glu Ala Cys Pro Thr Gly Leu Tyr Thr His Ser Gly Glu Cys Cys Lys
1               5                   10                  15

Ala Cys Asn Leu Gly Glu Gly Val Ala Gln Pro Cys Gly Ala Asn Gln
            20                  25                  30

Thr Val Cys Glu Pro Cys Leu Asp Ser Val Thr Phe Ser Asp Val Val
        35                  40                  45

Ser Ala Thr Glu Pro Cys Lys Pro Cys Thr Glu Cys Val Gly Leu Gln
    50                  55                  60

Ser Met Ser Ala Pro Cys Val Glu Ala Asp Asp Ala Val Cys Arg Cys
65                  70                  75                  80

Ala Tyr Gly Tyr Tyr Gln Asp Glu Thr Thr Gly Arg Cys Glu Ala Cys
                85                  90                  95

Arg Val Cys Glu Ala Gly Ser Gly Leu Val Phe Ser Cys Gln Asp Lys
            100                 105                 110

Gln Asn Thr Val Cys Glu Glu Cys Pro Asp Gly Thr Tyr Ser Asp Glu
        115                 120                 125

Ala Asn His Val Asp Pro Cys Leu Pro Cys Thr Val Cys Glu Asp Thr
    130                 135                 140

Glu Arg Gln Leu Arg Glu Cys Thr Arg Trp Ala Asp Ala Glu Cys Glu
145                 150                 155                 160

Glu Ile Pro Gly Arg Trp Ile Thr Arg Ser Thr Pro Pro Glu Gly Ser
                165                 170                 175

Asp Ser Thr Ala Pro Ser Thr Gln Glu Pro Glu Ala Pro Pro Glu Gln
            180                 185                 190

Asp Leu Ile Ala Ser Thr Val Ala Gly Val Val Thr Val Met Gly
        195                 200                 205

Ser Ser Gln Pro Val Val Thr Arg Gly Thr Thr Asp Asn
    210                 215                 220
```

<210> SEQ ID NO 5
<211> LENGTH: 1188
<212> TYPE: DNA
<213> ORGANISM: Artificial Sequence
<220> FEATURE:
<223> OTHER INFORMATION: human p75ECD - linker - human Fc fusion

<400> SEQUENCE: 5

```
aaggaggcat gccccacagg cctgtacaca cacagcggtg agtgctgcaa agcctgcaac      60
ctgggcgagg gtgtggccca gccttgtgga gccaaccaga ccgtgtgtga gccctgcctg     120
gacagcgtga cgttctccga cgtggtgagc gcgaccgagc cgtgcaagcc gtgcaccgag     180 tgcgtgggc tccagagcat gtcggcgccg tgcgtggagg ccgacgacgc cgtgtgccgc     240
tgcgcctacg gctactacca ggatgagacg actgggcgct gcgaggcgtg ccgcgtgtgc     300
gaggcgggct cgggcctcgt gttctcctgc aggacaagc agaacaccgt gtgcgaggag     360
tgccccgacg gcacgtattc cgacgaggcc aaccacgtgg acccgtgcct gccctgcacc     420
```

```
gtgtgcgagg acaccgagcg ccagctccgc gagtgcacac gctgggccga cgccgagtgc    480
gaggagatcc ctggccgttg gattacagac aaaactcaca catgcccacc gtgcccagca    540
cctgaactcc tggggggacc gtcagtcttc ctcttccccc caaaacccaa ggacaccctc    600
atgatctccc ggacccctga ggtcacatgc gtggtggtgg acgtgagcca cgaagaccct    660
gaggtcaagt tcaactggta cgtggacggc gtggaggtgc ataatgccaa gacaaagccg    720
cgggaggagc agtacaacag cacgtaccgg gtggtcagcg tcctcaccgt cctgcaccag    780
gactggctga atggcaagga gtacaagtgc aaggtctcca acaaagccct cccagccccc    840
atcgagaaaa ccatctccaa agccaaaggg cagccccgag aaccacaggt gtacaccctg    900
cccccatccc gggatgagct gaccaagaac caggtcagcc tgacctgcct ggtcaaaggc    960
ttctatccca gcgacatcgc cgtggagtgg gagagcaatg ggcagccgga gaacaactac   1020
aagaccacgc ctcccgtgct ggactccgac ggctccttct tcctctacag caagctcacc   1080
gtggacaaga gcaggtggca gcaggggaac gtcttctcat gctccgtgat gcatgaggct   1140
ctgcacaacc actacacgca gaagagcctc tccctgtctc cgggtaaa               1188
```

```
<210> SEQ ID NO 6
<211> LENGTH: 396
<212> TYPE: PRT
<213> ORGANISM: Artificial Sequence
<220> FEATURE:
<223> OTHER INFORMATION: human p75ECD - linker - human Fc fusion

<400> SEQUENCE: 6
```

```
Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Asp Lys Thr His Thr Cys Pro
                165                 170                 175

Pro Cys Pro Ala Pro Glu Leu Leu Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe
    210                 215                 220
```

```
Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
    290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
        355                 360                 365

Gly Asn Val Phe Ser Cys Ser Val Met His Glu Ala Leu His Asn His
    370                 375                 380

Tyr Thr Gln Lys Ser Leu Ser Leu Ser Pro Gly Lys
385                 390                 395
```

<210> SEQ ID NO 7
<211> LENGTH: 35
<212> TYPE: DNA
<213> ORGANISM: Artificial Sequence
<220> FEATURE:
<223> OTHER INFORMATION: Forward PCR primer for human p75ECD

<400> SEQUENCE: 7
gcgctctaga ccaccatggg ggcaggtgcc accgg    35

<210> SEQ ID NO 8
<211> LENGTH: 33
<212> TYPE: DNA
<213> ORGANISM: Artificial Sequence
<220> FEATURE:
<223> OTHER INFORMATION: Reverse PCR primer for human p75ECD

<400> SEQUENCE: 8
ctctgtcgac ttatcattta cccggagaca ggg    33

<210> SEQ ID NO 9
<211> LENGTH: 27
<212> TYPE: DNA
<213> ORGANISM: Artificial Sequence
<220> FEATURE:
<223> OTHER INFORMATION: Forward PCR primer for human Fc

<400> SEQUENCE: 9
aaccatgggc gacaaaactc acacatg    27

<210> SEQ ID NO 10
<211> LENGTH: 26
<212> TYPE: DNA
<213> ORGANISM: Artificial Sequence
<220> FEATURE:
<223> OTHER INFORMATION: Reverse PCR primer for human Fc

<400> SEQUENCE: 10

```
aagaattctc atttacccgg agacag                                            26
```

```
<210> SEQ ID NO 11
<211> LENGTH: 30
<212> TYPE: DNA
<213> ORGANISM: Artificial Sequence
<220> FEATURE:
<223> OTHER INFORMATION: Forward PCR primer for human Fc

<400> SEQUENCE: 11
ttggattaca gacaaaactc acacatgccc                                        30

<210> SEQ ID NO 12
<211> LENGTH: 33
<212> TYPE: DNA
<213> ORGANISM: Artificial Sequence
<220> FEATURE:
<223> OTHER INFORMATION: Reverse PCR primer for human Fc

<400> SEQUENCE: 12
ctctgtcgac ttatcattta cccggagaca ggg                                    33

<210> SEQ ID NO 13
<211> LENGTH: 2217
<212> TYPE: DNA
<213> ORGANISM: Artificial Sequence
<220> FEATURE:
<223> OTHER INFORMATION: Adeno-associated virus (AAV)8 capsid sequence
      with an AAV2 phospholipase domain

<400> SEQUENCE: 13
atggctgccg atggttatct tccagattgg ctcgaggaca ctctctctga aggaataaga        60
cagtggtgga agctcaaacc tggcccacca ccaccaaagc ccgcagagcg cataaggac        120 gacagcaggg gtcttgtgct tcctgggtac aagtacctcg acccttcaa cggactcgac        180 aagggagagc cggtcaacga ggcagacgcc gcggccctcg agcacgacaa agcctacgac        240
cggcagctcg acagcggaga caacccgtac ctcaagtaca accacgccga cgcggagttt        300
caggagcgcc ttaaagaaga tacgtctttt gggggcaacc tcggacgagc agtcttccag        360
gcgaaaaaga gggttcttga acctctgggc ctggttgagg aacctgttaa gacggctccg        420
ggaaagaaga gaccggtaga gccatcaccc cagcgttctc cagactcctc tacgggcatc        480
ggcaagaaag gccaacagcc cgccagaaaa agactcaatt ttggtcagac tggcgactca        540
gagtcagttc cagaccctca acctctcgga gaacctccag cagcgccctc tggtgtggga        600
cctaatacaa tggctgcagg cggtggcgca ccaatggcag acaataacga aggcgccgac        660
ggagtgggta gttcctcggg aaattggcat gcgattcca catggctggg cgacagagtc        720
atcaccacca gcacccgaac ctgggccctg cccacctaca acaaccacct ctacaagcaa        780
atctccaacg gacatcggg aggagccacc aacgacaaca cctacttcgg ctacagcacc        840
ccctgggggt attttgactt taacagattc cactgccact tttcaccacg tgactggcag        900
cgactcatca acaacaactg gggattccgg cccaagagac tcagcttcaa gctcttcaac        960
atccaggtca aggaggtcac gcagaatgaa ggcaccaaga ccatcgccaa taacctcacc        1020
agcaccatcc aggtgtttac ggactcggag taccagctgc cgtacgttct cggctctgcc        1080
caccagggct gcctgcctcc gttcccggcg gacgtgttca tgattcccca gtacggctac        1140
ctaacactca acaacggtag tcaggccgtg gacgctcct ccttctactg cctggaatac        1200
tttccttcgc agatgctgag aaccggcaac aacttccagt ttacttacac cttcgaggac        1260
```

```
gtgcctttcc acagcagcta cgcccacagc cagagcttgg accggctgat gaatcctctg    1320
attgaccagt acctgtacta cttgtctcgg actcaaacaa caggaggcac ggcaaatacg    1380
cagactctgg gcttcagcca aggtgggcct aatacaatgg ccaatcaggc aaagaactgg    1440
ctgccaggac cctgttaccg ccaacaacgc gtctcaacga caaccgggca aaacaacaat    1500
agcaactttg cctggactgc tgggaccaaa taccatctga atggaagaaa ttcattggct    1560
aatcctggca tcgctatggc aacacacaaa gacgacgagg agcgtttttt tcccagtaac    1620
gggatcctga ttttttggcaa acaaaatgct gccagagaca atgcggatta cagcgatgtc    1680
atgctcacca gcgaggaaga aatcaaaacc actaaccctg tggctacaga ggaatacggt    1740
atcgtggcag ataacttgca gcagcaaaac acggctcctc aaattggaac tgtcaacagc    1800 caggggggcct tacccggtat ggtctggcag aaccgggacg tgtacctgca gggtcccatc    1860
tgggccaaga ttcctcacac ggacggcaac ttccacccgt ctccgctgat gggcggcttt    1920
ggcctgaaac atcctccgcc tcagatcctg atcaagaaca cgcctgtacc tgcggatcct    1980
ccgaccacct tcaaccagtc aaagctgaac tctttcatca cgcaatacag caccggacag    2040
gtcagcgtgg aaattgaatg ggagctgcag aaggaaaaca gcaagcgctg gaacccccgag    2100 atccagtaca cctccaacta ctacaaatct acaagtgtgg actttgctgt taatacagaa    2160
ggcgtgtact ctgaaccccg ccccattggc acccgttacc tcacccgtaa tctgtaa       2217
```

METHOD OF TREATMENT OF CEREBRAL AMYLOID ANGIOPATHY WITH P75ECD PEPTIDE AND/OR P75ECD-FC FUSION PROTEIN

CROSS-REFERENCE TO RELATED APPLICATION(S)

This application is a § 371 national phase of International Application No. PCT/CN2016/077412, filed on Mar. 25, 2016, which claims the benefit of Australian Patent Application No. 2015901100, filed on Mar. 26, 2015, the contents of each of which are hereby incorporated herein in their entirety by express reference thereto.

TECHNICAL FIELD

The present disclosure relates to methods of diagnosing, detecting and/or prognosing neurological disorders and/or methods of treating neurological disorders. In a particular form the present disclosure relates to the use of neurotrophin receptor p75 and/or the extracellular domain thereof.

BACKGROUND

Neurotrophins are a small family of secreted neurotrophic factors that act via complicated signalling pathways that result in a broad spectrum of actions in the nervous system, including involvement in neurogenesis, neuronal survival, proliferation, differentiation, myelination, axonal growth and synaptic plasticity, and conversely, apoptosis and cell death, at all stages of neuronal development, adult life, neuronal injury and disease. The neurotrophin family includes nerve growth factor (NGF), brain-derived neurotrophic factor (BDNF), neurotrophin-3 (NT3) and neurotrophin-4/5 (NT4/5). Neurotrophins mediate their effects by binding to at least three different types of receptors, tropomyosin-related kinase (Trk) receptors (TrkA, TrkB and TrkC), sortilin, and the p75 neurotrophin receptor (p75; synonyms include p75NTR, p75(NTR), Gp80-LNGFR, Low-affinity nerve growth factor receptor, Low affinity neurotrophin receptor, NGF receptor, and tumour necrosis factor receptor superfamily member 16 precursor (TNFRSF16)). High affinity binding of neurotrophins frequently involves two of these receptor types interacting as co-receptors.

p75 mediates survival or apoptosis of neurons depending on relative expression levels of high affinity neurotrophin Trk receptors. p75 undergoes extracellular domain (or ectodomain) shedding, wherein the extracellular domain of p75 (p75ECD) is cleaved from the full length protein. p75ECD shedding is physiologically regulated by tumor necrosis factor-alpha-converting enzyme (TACE), followed by regulated-intramembraneous proteolysis by gamma-secretase. However, the physiological and pathological significance of p75 shedding is not known. The regulation of p75 shedding and the function of diffusible p75ECD after shedding in vivo are yet to be determined.

Alteration in neurotrophin levels and signalling pathways have been implicated with the neuronal survival and pathophysiology in a wide variety of neurodegenerative and psychiatric disorders including Alzheimer's Disease (AD), cerebral amyloid angiopathy (CAA), Huntington's Disease, Parkinson's Disease and amyotrophic lateral sclerosis (ALS) and tauopathies, as well as neuronal injury such as spinal cord injury; although no human disease has yet been shown to be caused directly by a defect in neurotrophins or their receptors.

AD is the most common form of dementia, with approximately 24 million people suffering from the disease worldwide. AD is characterised by progressive cognitive deterioration, including memory loss, declining ability to perform daily living activities and by neuropsychiatric symptoms or behavioural changes. Pathologically, the brains of AD sufferers are characterised by "neurofibrillary tangles" (NFT) and "amyloid plaques" that are not seen in normal brains. The amyloid plaques in AD are formed by the accumulation of a misfolded and toxic amyloid-β (Aβ) protein in the cerebral cortex and hippocampus. Aβ is a metabolic product of amyloid precursor protein (APP), and in the normal brain, a steady-state level of Aβ is maintained by the balance between Aβ production and clearance. This balance is lost in AD sufferers. Interestingly, the Aβ peptide has been found to be a ligand for p75, and it can activate signalling cascades. It has been proposed that p75 mediates Aβ-induced neurotoxicity.

Cerebral amyloid angiopathy (CAA) is being increasingly recognised as an important cause of spontaneous intracerebral haemorrhage (ICH) and cognitive impairment in elderly people. It is characterised by progressive deposition of Aβ in the wall of small to medium-sized blood vessels in the cerebral cortex and leptomeninges causing vascular dementia. It favours posterior cortical regions, followed by frontal temporal and parietal lobes. CAA can also affect cerebellar vessels, but only rarely those in the brain stem or basal ganglia. CAA and AD are distinct conditions. However, a systematic review of four population-based post-mortem studies indicated a CAA prevalence of 28-38% in nondemented patients and 55-69% in patients with dementia (Keage et al. 2009). CAA is found in 82-98% of AD cases, although severe CAA is seen in only 25% of AD cases (Charidimou et al. 2012; Jellinger, 2002).

Tauopathies are a heterogeneous class of neurodegenerative diseases characterised by the pathological aggregation of tau protein in the brain. The tau protein is a microtubule-associated protein (MAP), which interacts with tubulin to stabilize axonal microtubules and promote tubulin assembly into microtubules in normal individuals. Tau proteins are abundant in neurons of the central nervous system and are less common elsewhere, but are also expressed at very low levels in CNS astrocytes and oligodendrocytes. Tauopathies can result when tau proteins become defective and no longer stabilize microtubules properly. This can lead to intracellular accumulation of and formation of neurofibrillary tangles (NFT). Tau is a phosphoprotein with up to 79 potential serine (Ser) and threonine (Thr) phosphorylation sites on the longest tau isoform. Phosphorylation has been reported on approximately 30 of these sites in normal tau proteins; however, hyperphosphorylation is associated with the self-assembly of NFT.

NFTs can be observed in a range of tauopathic diseases including AD, progressive supranuclear palsy, dementia pugilistica (chronic traumatic encephalopathy), frontotemporal dementia and parkinsonism linked to chromosome 17, Lytico-Bodig disease (Parkinson-dementia complex of Guam), tangle-predominant dementia (which has NFTs similar to AD, but without plaques), ganglioglioma and gangliocytoma, meningioangiomatosis, subacute sclerosing panencephalitis, Huntington's disease etc. AD patients may have a varying degree of NFT involvement; however, NFT may be present in patients that do not suffer from AD.

Accordingly, tauopathy is a distinct component of AD that is not associated with the amyloid plaques.

As disclosed herein, p75ECD has been advantageously realised to be a neuroprotective factor that may be utilised to diagnose, prevent or treat neurological disorders and/or protect neurons from apoptosis and neurodegeneration. Moreover, the role of full length p75 (p75FL) may advantageously additionally or alternatively be utilised to diagnose neurological disorders, and/or this factor may be targeted to prevent or treat neurological disorders and/or protect neurons from apoptosis and neurodegeneration.

SUMMARY

According to an aspect of the present disclosure, there is provided a method of diagnosing and/or prognosing Alzheimer's Disease (AD) in a test subject comprising
(a) obtaining a biological sample from the test subject,
(b) measuring concentration of p75 extracellular domain (p75ECD) and/or full length p75 (P75FL) in the biological sample of the test subject, and
(c) comparing the concentration of the p75ECD and/or p75FL and/or the ratio of p75ECD:p75FL in the biological sample of the test subject to the concentration of the p75ECD and/or p75FL and/or the ratio of p75ECD:p75FL in a comparable biological sample obtained from a non-demented control subject or group of non-demented control subjects,
wherein Alzheimer's disease is diagnosed and/or prognosed when the concentration of the p75ECD and/or p75FL and/or the ratio of p75ECD:p75FL in the test subject is altered compared to the concentration of the p75ECD and/or p75FL and/or the ratio of p75ECD:p75FL in the non-demented control subject or group of non-demented control subjects.

In an embodiment, the method comprises
(a) obtaining a biological sample from the test subject,
(b) measuring concentration of p75 extracellular domain (p75ECD) in the biological sample of the test subject, and
(c) comparing the concentration of p75ECD in the biological sample of the test subject to the concentration of p75ECD in a comparable biological sample obtained from a non-demented control subject or group of non-demented control subjects,
wherein Alzheimer's disease is diagnosed and/or prognosed when the concentration of p75ECD in the test subject is decreased compared to the non-demented control subject or group of non-demented control subjects.

In an embodiment, the method comprises
(a) obtaining a biological sample from the test subject,
(b) measuring concentration of p75ECD and p75FL in the biological sample of the test subject, and
(c) comparing the concentration of p75ECD and p75FL in the biological sample of the test subject to the concentration of p75ECD and p75FL in a comparable biological sample obtained from a non-demented control subject or group of non-demented control subjects,
wherein Alzheimer's disease is diagnosed and/or prognosed when the ratio of p75ECD:p75FL in the test subject is decreased compared to the non-demented control subject or group of non-demented control subjects.

In an embodiment, the method comprises
(a) obtaining a biological sample from the test subject,
(b) measuring concentration of p75FL in the biological sample of the test subject, and
(c) comparing the concentration of p75FL in the biological sample of the test subject to the concentration of p75FL in a comparable biological sample obtained from a non-demented control subject or group of non-demented control subjects,
wherein Alzheimer's disease is diagnosed and/or prognosed the concentration of p75FL in the test subject is increased compared to the non-demented control subject or group of non-demented control subjects.

According to another aspect of the present disclosure, there is provided a method of treating and/or preventing cerebral amyloid angiopathy (CAA) or a tauopathy, comprising administering to a subject in need thereof a therapeutically effective amount of p75 extracellular (p75ECD) or a functional fragment, variant, analogue or derivative thereof.

In a further aspect of the present disclosure, there is provided a method of protecting neurons against apoptosis and/or neurodegeneration induced by neurotoxic factors such as Aβ, comprising administering to a subject in need thereof a therapeutically effective amount of a p75ECD or a functional fragment, variant, analogue or derivative thereof.

In an embodiment, the p75ECD or functional fragment, variant, analogue or derivative thereof is p75ECD. In an embodiment, the p75ECD has an amino acid sequence provided by SEQ ID NO: 4. In an embodiment, the p75ECD is a p75ECD-Fc fusion. In an embodiment, the p75ECD-Fc has an amino acid sequence provided by SEQ ID NO: 6. In an embodiment, the p75ECD-Fc fusion is administered as p75ECD-Fc fusion adeno-associated virus (AAV) vector. In an embodiment, the p75ECD-Fc fusion is a recombinant peptide. In an embodiment, the p75ECD is administered via intraperitoneal, intraventricular, intracranial or intramuscular injection.

In an embodiment, the subject is human.

DETAILED DESCRIPTION

Figure 1:
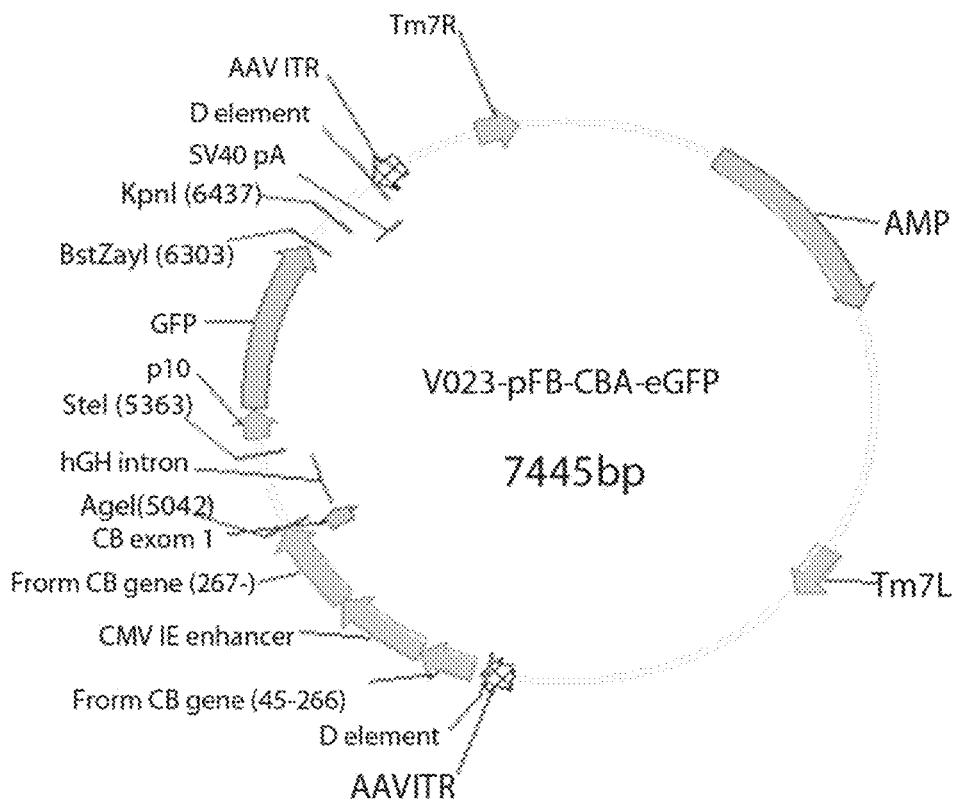
FIG. 1 provides AAV-p75ECD-Fc vector construction and characterization with (a) the plasmid map showing AAV-GFP vector design, and (b) SDS-PAGE analysis showing the purity and homogeneity of AAV-GFP and AAV-p75ECD-Fc preparations, and (c), the plasmid map showing AAV-p75ECD-Fc vector design.
Figure 1:
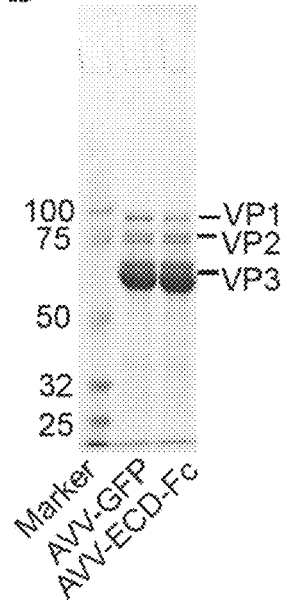
Figure 1:
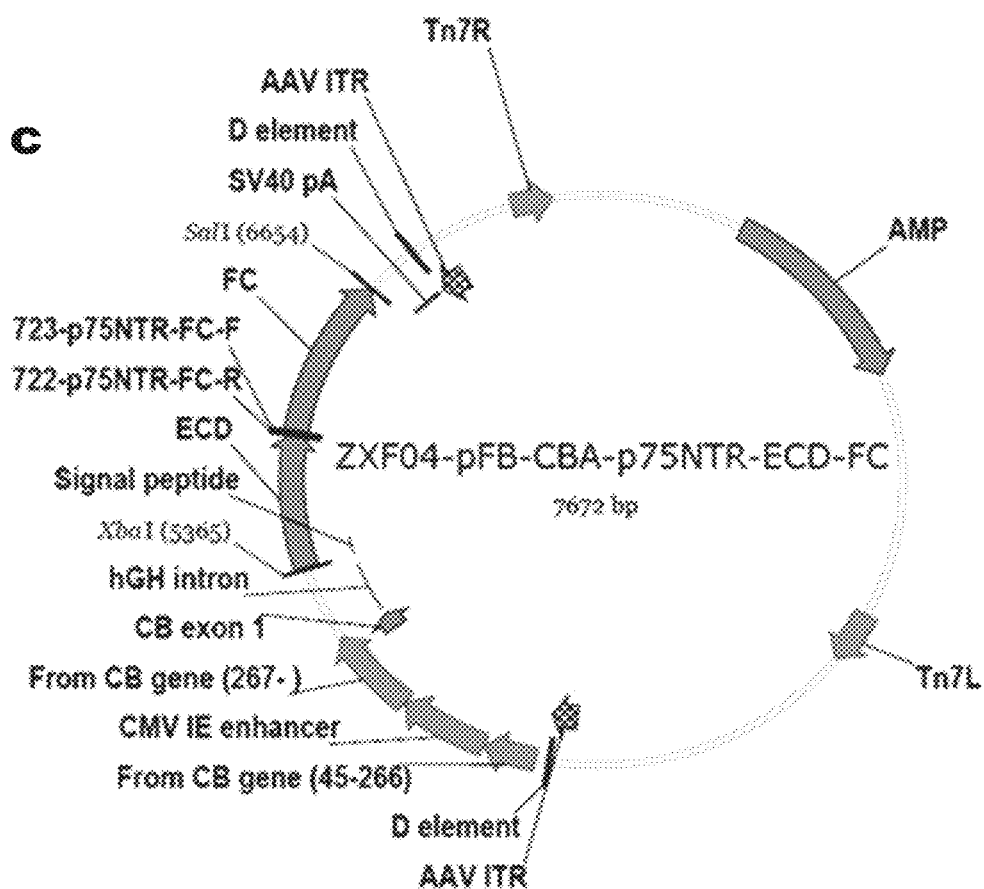

As disclosed herein, it has been realised that the balance of full length p75 and the extracellular domain of p75 (p75ECD) present within an individual may dictate whether the individual suffers from neurodegeneration, which can lead to a range of neurological diseases. Specifically, it has been realised that p75ECD is a neuroprotective factor. While not wanting to be bound by theory, it is believed that soluble p75ECD competes with cell membrane bound p75 for ligands such as neurotrophins, thereby preventing p75 signalling that can lead to neuronal degeneration and/or apoptosis.

The levels of p75ECD in the brain and cerebrospinal fluid (CSF) of AD patients and mouse models of AD have been investigated as described herein. In one aspect, it has been realised that AD is associated with low levels of p75ECD, high levels of full length p75 (referred to as p75 or p75FL herein) and/or a low p75ECD:p75FL ratio compared to normal, non-demented control subjects. Further, it had been realised that concentration of p75ECD, p75FL and/or a p75ECD:p75FL ratio can be used as diagnostic or prognostic markers. Moreover, in another aspect disclosed herein, it has been found that the restoration of p75ECD levels, for example, by administration of p75ECD, reduces neurodegenerative diseases such as AD, cerebral amyloid angiopathy (CAA) and Tau pathologies and improves learning and memory in both early and later phases of AD in an APP/PS1 mouse model.

Accordingly, in an aspect, the present disclosure provides a method of diagnosing and/or prognosing Alzheimer's Disease (AD) in a test subject comprising
(a) obtaining a biological sample from the test subject,
(b) measuring concentration of p75 extracellular domain (p75ECD) and/or full length p75 (P75FL) in the biological sample of the test subject, and
(c) comparing the concentration of the p75ECD and/or p75FL and/or the ratio of p75ECD:p75FL in the biological sample of the test subject to the concentration of the p75ECD and/or p75FL and/or the ratio of p75ECD:p75FL in a comparable biological sample obtained from a non-demented control subject or group of non-demented control subjects,
wherein Alzheimer's disease is diagnosed and/or prognosed when the concentration of the p75ECD and/or p75FL and/or the ratio of p75ECD:p75FL in the test subject is altered compared to the concentration of the p75ECD and/or p75FL and/or the ratio of p75ECD:p75FL in the non-demented control subject or group of non-demented control subjects.

The terms "p75FL", "full length p75", "p75" and "p75NTR" are used interchangeably and as used herein refer to the entire (full length) p75 neurotrophin receptor (also known as p75 or p75NTR.

The terms "extracellular domain of p75", "p75ECD", "p75 extracellular domain", "ectoderm domain of p75" and "p75 ectoderm" are used interchangeably and all refer to a fragment of that can be derived from the full length p75 peptide following cleavage of p75 by tumour necrosis factor alpha-converting enzyme (TACE)/ADAM17 at the juxtamembrane region, which releases or "sheds" the extracellular domain of p75FL (p75ECD) (Weskamp et al 2004) as a soluble peptide. In an embodiment, the p75ECD is shed from the p75FL peptide, and, in this embodiment, the p75ECD is soluble. As used herein, the term "soluble" indicates that the protein, polypeptide, or peptide is not, and does not become, bound to a cellular membrane, and is, accordingly, characterised by the absence or functional disruption of all or a substantial part of the transmembrane (i.e. lipophilic) domain, so that the protein, polypeptide, or peptide is devoid of any membrane anchoring function.

The p75 and/or p75ECD described herein can be from any suitable species. In an embodiment, the p75 and/or p75ECD is derived from a human. However, in an embodiment, the p75 and/or p75ECD could alternatively be derived from an animal of commercial, scientific, medical or personal significance, such as non-human primates, rat and/or mouse, and/or other mammals such as livestock, exotic animals, and companion animals (including race horses, sheep, cows, goats, pigs, lions, tigers, elephants, dogs, cats, rabbits, rats and mice, etc). In an embodiment, the p75 and/or p75ECD may be derived from a primate, for example, a rhesus macaque, a chimpanzee, an orangutan, a chimpanzee, a gorilla, etc.

The human full length p75 nucleotide sequence is provided at Genbank Accession No. NM_002507 at nucleotides 126-1409 and in SEQ ID NO: 1.

The human full length p75 amino acid sequence is provided in SEQ ID NO: 2.

Human p75ECD consists of amino acids 29 to 250 of SEQ ID NO: 2, and includes 28 amino acids as a single peptide which is followed by four cysteine rich domains each of which contain 40 amino acid residues and each of them contains an N-glycosylated site (Schor, 2005). The human p75ECD nucleotide sequence is provided in SEQ ID NO: 3.

The human p75ECD amino acid sequence is provided in SEQ ID NO: 4.

In an embodiment, the p75FL and/or p75ECD can be a genetic or peptide variant. A "variant" of p75 and/or p75ECD, as referred to herein, is to be understood to represent an isoform of p75FL encoded by, for example, an allelic variant. Variants are detailed further elsewhere herein.

As used herein, the term "test subject" refers to the individual being assessed for diagnosis, detection or prognosis of Alzheimer's disease. In an embodiment, the test subject may be human. However, it is envisioned that the subject could alternatively be an animal of commercial, scientific, medical or personal significance, such as non-human primates and other mammals such as livestock, exotic animals, and companion animals (including race horses, sheep, cows, goats, pigs, lions, tigers, elephants, dogs, cats, rabbits, rats and mice, etc).

As used herein, the term "non-demented control subject or group of non-demented control subjects" refers to an individual or group of individuals that are considered to be normal and well, whom, in particular, do not suffer from dementia-related neurological condition(s). In an embodiment, the non-demented control subject or group of subjects do not develop a dementia-related neurological condition within 10 years of providing the sample. In an embodiment, the non-demented control subject or group of subjects do not develop a neurological condition within 5 years of providing the sample. IN an embodiment, the non-demented control subject is the same species as the test subject. In an embodiment, the non-demented control subject(s) are age-matched, wherein the non-demented control subject(s) are within 10 years of the age of the test subject. In an embodiment, the non-demented control subject(s) are within 5 years of the age of the test subject. In an embodiment, the concentration of the p75ECD and/or p75FL (or the ratio thereof as described herein) of the test subject is compared to a reference value that is known to be a representative value for p75ECD and/or P75FL (or ratio thereof) in a non-demented control subject or group of non-demented control subjects. Such reference values may be adjusted for factors that may affect the p75ECD and/or p75FL concentration (or ratio thereof) such as age.

The term "concentration" as used herein is intended to refer to the amount or level of the p75ECD and/or p75FL molecules in the biological sample, and is intended to encompass both an absolute amount (eg the amount of the p75ECD and/or p75FL molecule in a sample as measured in mg/ml, ng/ml, pg/ml, ng/g etc) as well as a relative amount (for example, as measured by densitometric analysis of staining of a specific band on a Western blot, wherein the result for the test subject can optionally be normalised against that for the non-demented control subject(s)). In accordance with the first aspect of the disclosure, where the concentration measured is an absolute amount, the absolute concentration of the p75ECD and/or p75FL molecule in the test subject is compared to the absolute concentration of the p75ECD and/or p75FL in the non-demented control subject or group of non-demented control to determine whether there has been an alteration (ie increase or decrease) in concentration. Alternatively, when the concentration measured is a relative amount (eg as measured by densitometric analysis of Western blot analysis), the intensity of the staining (or other relative measurement) of the p75ECD or p75FL molecule concentration in the test subject is compared to the intensity of the staining (or said other relative measure) of the p75ECD and/or p75FL concentration in the non-demented control subject or group of non-demented control to determine whether there has been an alteration (ie increase or decrease) in concentration.

It will be apparent to those skilled in the art that the ratio of p75ECD:p75FL may readily be calculated by dividing the absolute or relative concentration of p75ECD by the absolute or relative (respectively) concentration of p75FL.

The biological sample may be any suitable body sample type that can be sampled for p75FL and/or p75ECD concentration. For example, the biological sample may be selected from the group consisting of brain tissue, cerebrospinal fluid (CSF), serum, plasma, whole blood and peripheral blood mononuclear cells (PBMC) and lymphocytes. However, those skilled in the art will appreciate that other tissue types of bodily fluids may be suitable for sampling p75FL and p75ECD levels. In an embodiment, the biological sample is cerebrospinal fluid. In an embodiment, the biological sample is brain tissue. In an embodiment, the biological sample is selected from lymphocytes, plasma, serum and/or whole blood.

In an embodiment where the biological sample is brain tissue, the brain tissue sample may be obtained after the death of the subject, or alternatively, as a tissue biopsy using standard biopsy techniques well known to those skilled in the art. The brain tissue can optionally be treated by methods known to those skilled in the art, such as be homogenisation and/or sonication. The person skilled in the art will appreciate that other tissue types can be similar treated as required. In an embodiment, where the biological sample is CSF, the CSF may be obtained using standard CSF collection techniques known to those skilled in the art, for example, by lumbar puncture.

The term "comparative biological sample" as measured in the non-demented control subject(s) as referred to herein refers to the same or similar type of biological sample as that measured for the test subject, or where the concentration of the p75FL, p75ECD and/or p75ECD:p75FL ratio in one body sample can accurately predict the concentration of the p75FL, p75ECD and/or p75ECD:p75FL ratio (respectively) in another body sample. For example, those skilled in the art will understand that the concentration of an analyte in a serum sample is substantially equivalent to the concentration of the same analyte in a plasma sample since the difference between plasma and serum is merely that serum does not contain fibrinogen and other clotting factors. Accordingly, in an embodiment, plasma and serum are comparative biological samples. Moreover, those skilled in the art will understand that the concentration of analyte in a serum or plasma sample corresponds to approximately twice the concentration of the analyte in a whole blood sample, since whole blood comprises approximately half serum or plasma. Accordingly, the concentration of an analyte in whole blood can be compared to plasma or serum as the comparable concentrations can be converted by a simple calculation.

As disclosed herein, it has surprisingly been realised that the concentration of p75ECD is decreased in AD patients and AD mice compared to their non-demented counterparts, and further, that the concentration of p75FL is increased in AD patients and AD mice compared to their non-demented counterparts. Moreover, as disclosed herein, it has been noted that the ratio of p75ECD:p75FL in the AD patients and AD mice is decreased compared to their non-demented counterparts.

Accordingly, in an embodiment, a method of diagnosing and/or prognosing Alzheimer's Disease (AD) in a test subject comprising
(a) obtaining a biological sample from the test subject,
(b) measuring concentration of p75 extracellular domain (p75ECD) in the biological sample of the test subject, and
(c) comparing the concentration of p75ECD in the biological sample of the test subject to the concentration of p75ECD in a comparable biological sample obtained from a non-demented control subject or group of non-demented control subjects,
wherein Alzheimer's disease is diagnosed and/or prognosed when the concentration of p75ECD in the test subject is decreased compared to the non-demented control subject or group of non-demented control subjects.

The concentration of p75ECD in the test subject that may be regarded as being "decreased compared to the non-demented control subject or group of non-demented control subjects" such that the determination of whether Alzheimer's disease is diagnosed or prognosed may vary according to the species of the subject, the particular body sample type used and the age of the subject. In an embodiment, the p75ECD concentration is decreased in the test subjects compared to non-demented controls by approximately 25% to 99%. In an embodiment, p75ECD concentration is decreased in the test subjects compared to non-demented controls by approximately 25% to 90%. In an embodiment, p75ECD concentration is decreased in the test subjects compared to non-demented controls by approximately 30% to 80%. In an embodiment, p75ECD concentration is decreased in human AD patients compared to non-demented human controls by approximately 50%. In an embodiment, the decrease is approximately 50% in cerebrospinal fluid (CSF). In an embodiment, the decrease is approximately 75% in brain tissue. In an embodiment, p75ECD levels are decreased in human AD patients compared to non-demented human controls by at least 75% in human brain tissue. In an embodiment, the concentration of the p75ECD in CSF of the test subject that diagnoses or prognoses AD is less than 500 pg/ml. Similarly, in an embodiment, p75ECD concentration is decreased in AD mice compared to wild-type (wt) litter mates by approximately 50% in mouse CSF, or, in an alternative or additional embodiment, the decrease is approximately 50% in mouse brain tissue.

As disclosed herein, it has been realised that the normal human concentration range of p75ECD in CSF ranges from about 500 pg/ml to about 1300 pg/ml in non-demented controls. In an embodiment, the decreased concentration of p75ECD in CSF of a human test subject such that AD is diagnosed or prognosed is less than 500 pg/ml, preferably less than 400 pg/ml. In an embodiment, the decreased concentration of p75ECD in CSF of a test subject such that AD is diagnosed or prognosed is less than 300 pg/ml.

In another embodiment, the present disclosure provides a method of diagnosing and/or prognosing Alzheimer's Disease (AD) in a test subject comprising
(a) obtaining a biological sample from the test subject,
(b) measuring concentration of p75ECD and full length p75 (p75FL) in the biological sample of the test subject, and
(c) comparing the concentration of p75ECD and p75FL in the biological sample of the test subject to the concentration of p75ECD and p75FL in a comparable biological sample obtained from a non-demented control subject or group of non-demented control subjects,
wherein Alzheimer's disease is diagnosed and/or prognosed when the ratio of p75ECD:p75FL in the test subject is decreased compared to the non-demented control subject or group of non-demented control subjects.

In an embodiment, the ratio of p75ECD:p75FL in the test subject is decreased compared to the non-demented control subject or group of non-demented control subjects by at least 30%. In an embodiment, the ratio is decreased by at least 50%. In an embodiment, the ratio is decreased by at least 75%. In an embodiment, the ratio is decreased by at least 90%. In an embodiment, the ratio is decreased by at least 99%.

In yet another embodiment, the present disclosure provides a method of diagnosing and/or prognosing Alzheimer's Disease (AD) in a test subject comprising
(a) obtaining a biological sample from the test subject,
(b) measuring concentration of p75FL in the biological sample of the test subject, and
(c) comparing the concentration of p75FL in the biological sample of the test subject to the concentration of p75FL in a comparable biological sample obtained from a non-demented control subject or group of non-demented control subjects,
wherein Alzheimer's disease is diagnosed and/or prognosed the concentration of p75FL in the test subject is increased compared to the non-demented control subject or group of non-demented control subjects.

In an embodiment, the concentration of p75FL in the test subject is increased compared to the non-demented control subject or group of non-demented control subjects by 10% to 500% (that is, 1.1- to 5-fold). In an embodiment, the concentration of p75FL is increased by 20% to 300% (that is, 1.2- to 3-fold). In an embodiment, the concentration of p75FL is increased by 30% to 200% (that is, 1.3- to 2-fold). In a particular embodiment, the concentration of p75FL is increased in human brain tissue by at least 200% (two-fold), or preferably, 300% (three-fold).

However, the amount of p75FL and/or p75ECD that may be regarded as an increased concentration, decreased concentration or provide a decreased ratio in the test subject compared to the non-demented control subject or group of non-demented control subjects for the purposes of the method of the first aspect of the present disclosure, may vary according to which factor (eg p75FL, p75ECD or the ratio of p75ECD:p75FL) is being compared, the particular body sample type used and the age of the subject.

In an embodiment, the p75FL and/or p75ECD measured in the first aspect of the disclosure are peptides.

Quantifying or measuring the concentration of the p75FL and/or p75ECD peptides can be performed using suitable techniques known to those skilled in the art, such as by comparing staining to known protein standards to measure an absolute concentration of a molecule, or otherwise, by comparing relative staining intensity between a test subject and a normal non-demented control(s) using densitometric analysis to measure relative concentration, including using methods as described herein. The concentration of p75FL and/or p75ECD peptides can be determined using techniques well known to those skilled in the art, such as by quantifying results obtained from Western blot analysis, immunoassays such as enzyme-linked immunosorbant assay (ELISA), radioimmunoassay (RIA) and immunohistochemistry (eg with sectionalised samples of a tissue biopsy, including immunofluorescence staining) using anti-p75FL and/or p75ECD antibodies or fragments thereof. However, it is also possible to detect and quantify the levels of p75FL and/or p75ECD using other methods well known to those skilled in the art such as, for example, methods involving the detection of binding of p75FL and/or p75ECD to any other ligands that may bind p75FL and/or p75ECD (eg Aβ). Particularly suitable methods for determining the amount of p75FL and/or p75ECD present in a test body sample(s) are immunoassays utilising labelled molecules in various sandwich, competition, or other assay formats. Such immunoassays will develop a signal which is indicative for the presence or absence of p75FL and/or p75ECD. Further, the strength of the signal generated by such immunoassays may be correlated directly or indirectly (for example, reversely proportional) to the amount of p75FL and/or p75ECD present in a sample(s). Other suitable methods for determining the amount of p75FL and/or p75ECD present in a test body sample(s) are methods comprising the measurement of a physical or chemical property specific for p75FL and/or p75ECD such as a precise molecular mass or nuclear magnetic resonance (NMR) spectrum. Such methods may, therefore, be conducted using biosensors, optical devices coupled to immunoassays, biochips, analytical devices such as mass-spectrometers, NMR-analysers and chromatography devices. Other suitable methods may involve precipitation (eg immunoprecipitation), electrochemiluminescence (ie electro-generated chemiluminescence), electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry and nephelometry. Further, methods that are well known to those skilled in the art, such as gel electrophoresis, Western Blotting and mass spectrometry, may also be used alone or in combination with other suitable methods as described above. Those skilled in the art will appreciate that other methods may be suitable for detecting the concentration of p75 or p75ECD peptides in accordance with the methods described herein.

The full length p75FL peptide and the p75ECD peptide can be distinguished using specific antibodies that recognise different regions of the p75FL peptide as would be understood to those skilled in the art. For example, a first antibody may specifically recognise and bind to the extracellular domain of p75 (p75ECD) but not to the intracellular or transmembrane region, such as anti-p75ECD antibody (rabbit polyclonal, 9650) as used herein; and a second antibody may specifically recognise and bind to the intracellular or transmembrane region of p75 (p75ICD) but not to the extracellular domain, such as anti-p75NTR antibody (rabbit polyclonal, AB1554, Millipore, US) or anti-NGF receptor p75 (Cat.No. AB1554, Millipore, US), as used herein. Those skilled in the art will appreciate that other suitable antibodies that either specifically recognise and bind to the extracellular domain of p75 but not to the intracellular or transmembrane region, or that specifically recognise and bind to the intracellular or transmembrane region of p75 but not to the extracellular domain, can readily be used in the methods of the disclosure.

However, in an embodiment, at least some of the p75ECD may be present in the context of full length p75 which may be associated with a cellular component. That is, in an embodiment, full length p75 is associated with the cellular membrane component of a cellular preparation as a transmembrane protein, whereas soluble ("shed") p75ECD will be associated with the soluble component of cellular, tissue and/or body fluid preparations. In an embodiment, soluble (ie "shed") p75ECD can be distinguished from p75ECD that is present in the context of full length p75 by Western blotting on the basis of size (ie molecular weight) as will be appreciated by those skilled in the art. Alternatively, in an embodiment, soluble or "shed" p75ECD can be distinguished from full length p75ECD by omitting detergent or similar substances from the cell preparation method such that the cellular membranes (and accordingly, membrane-bound full length p75) can be separated from the soluble component of the preparation (and accordingly, soluble p75ECD) by centrifugation as would be understood by those skilled in the art. It may otherwise be possible to determine the amount of p75ECD, or the ratio of p75ECD:p75FL, by quantifying the intensity of an anti-p75ECD antibody binding to the sample, and the intensity of the binding of an anti-p75ICD antibody using appropriate controls, and calculate the either the absolute amount or the ratio using simple calculations.

The method of the first aspect enables the change in the amount of p75FL and/or p75ECD or ratio thereof to be used as a diagnostic marker of the presence of Alzheimer's disease. However, the sensitivity and specificity of such a method may depend on more than just the analytical "quality" of the method; it may also depend on the definition of what constitutes an abnormal result. That is, typically, for any particular marker, the distribution of marker levels for subjects with and without a disease overlaps such that a diagnostic/prognostic test based on that marker will not absolutely distinguish a normal (ie non-demented) subject from a diseased subject with complete accuracy. Thus, in some embodiments, the method may further comprise calculating receiver operating characteristic (ROC) curves by, for example, plotting the value of the p75FL and/or p75ECD change in amount versus the relative frequency of that value in "normal" and "disease" subject(s). The area under an ROC curve calculated in this manner can then be used as a measure of the probability that the determined change in amount of p75FL and/or p75ECD in the test body sample(s) will allow a correct diagnosis or prognosis. In addition, a ROC curve can even be used where the determined change in amount of p75FL and/or p75ECD may be considered as being inaccurate, because as long as it is possible to rank results, a ROC curve can still be calculated. For example, the determined p75FL and/or p75ECD amounts from test body sample(s) from subjects may be ranked according to degree (say 1=low, 2=normal, and 3=high). This ranking can then be correlated to results from normal subject(s) and an ROC curve created according to methods well known to those skilled in the art (eg Hanley and McNeil, 1982).

As such, the determination of the amount of p75FL and/or p75ECD in the test body sample(s) may comprise the steps of (i) contacting p75FL and/or p75ECD with a specific ligand, (ii) optionally removing non-bound ligand, and (iii) measuring the amount of bound ligand. The bound ligand (which may be bound by covalent and/or non-covalent binding) will generate an intensity signal. As indicated above, the ligand may be selected from anti-p75FL and/or p75ECD antibodies or fragments thereof but might otherwise be selected from any other ligands that may bind p75FL and/or p75ECD such as, for example, any compound (including peptides, polypeptides, nucleic acids, aptamers (eg nucleic acid or peptide aptamers), glycoproteins such as fetuin, and small molecules) that bind to p75FL and/or p75ECD. However, preferably, the ligand is selected from anti-p75FL and/or p75ECD antibodies or fragments thereof (including polyclonal and monoclonal antibodies, as well as fragments thereof, such as Fv, Fab and F(ab)$_2$ fragments that are capable of binding p75FL and/or p75ECD, and recombinant antibodies such as single chain antibodies (eg scFV antibodies)). Methods of preparing such ligands are well known to those skilled in the art.

In an embodiment, the ligand binds specifically to p75FL and/or p75ECD. As used herein, the term "specific binding" means that the ligand should not bind substantially to (that is, substantially "cross-react" with) another peptide, polypeptide or substance present in the test body sample. Preferably, the specifically bound p75FL and/or p75ECD will be bound with at least 3 times higher, more preferably at least 10 times higher, and most preferably at least 50 times higher affinity than any other relevant peptide, polypeptide or substance. Non-specific binding may be tolerable, if it can still be distinguished and measured unequivocally, for example, according to its size on a Western Blot, or by the relatively higher abundance of p75FL and/or p75ECD in the sample, or if it can be controlled for using a negative control sample or a normal subject(s) control sample. The ligand may be coupled covalently or non-covalently to a label allowing detection and measurement of the ligand. Suitable labelling may be performed by any of the direct or indirect methods well known to those skilled in the art.

As disclosed herein, it has been realised that p75FL and p75ECD concentration can readily be determined from tissues and body fluids including CSF and brain tissue. p75 and p75ECD peptide levels can also readily be detected in serum and in lymphocytes using standard methods known to those skilled in the art such as ELISA and Western blotting (see, for example, Zhou et al., 2013). It follows that p75FL and/or p75ECD can also optionally be detected in other tissue and body fluid types using similar techniques. In an embodiment, the p75FL is a transmembrane molecule, and can be detected in cells. For example, p75 could be detected in a variety of cell types such as lymphocytes, macrophages, skin cells, Schwann cells, and many neuronal cells. p75 levels can readily be detected in lymphocytes derived from peripheral blood using techniques known to those skilled in the art such as ELISA and Western blot (see, for example, Zhou et al, 2013).

However, those skilled in the art will appreciate that p75FL level can be indirectly quantified by measuring the amount of messenger RNA (mRNA) molecules encoding p75FL within a cell. For example, p75 mRNA could be detected in a variety of cell types such as lymphocytes, macrophages, skin cells, Schwann cells, and many neuronal cells. Indeed, p75 mRNA levels can readily be detected in lymphocytes derived from peripheral blood using techniques known to those skilled in the art such as real time reverse transcriptase PCR (real time RT-PCR) (see, for example, Zhou et al., 2013) and RT-PCR.

In an embodiment, the method of the first aspect may be used to prognose AD, wherein the concentration of the p75ECD and/or P75FL and/or a ratio of p75ECD:p75FL in the test subject is altered compared to the concentration of p75ECD and/or P75FL and/or a ratio of p75ECD:p75FL in the non-demented control subject or group of non-demented control subjects, even though no or mild signs of symptoms of AD are present in the test subject.

As disclosed herein, it has also been realised that p75ECD is a neurotropic molecule that can protect against amyloid beta toxicity and reduce tau phosphorylation associated with tauopathy. As disclosed herein, the signs and/or symptoms associated with neurological conditions such as Alzheimer's disease (AD), cerebral amyloid angiopathy (CAA) or a tauopathy can be reduced by administering p75 extracellular domain (p75ECD) in a mouse model that over expresses Aβ. Such administration may reduce signs and or symptoms of the neurological conditions by improving learning and memory, and protecting neurons from neurodegeneration induced by amyloid beta, and reduced tau protein phosphorylation.

Accordingly, in another aspect, the present disclosure provides a method of treating or preventing cerebral amyloid angiopathy (CAA) or a tauopathy, comprising administering to a subject in need thereof a therapeutically effective amount of p75 extracellular domain (p75ECD).

CAA is a distinct condition from AD, which can be characterised by progressive deposition of Aβ in the wall of small to medium-sized blood vessels in the cerebral cortex and leptomeninges causing vascular dementia. As disclosed herein, it has been found that administration of p75ECD reduces CAA lesions in an AD mouse model upon administration of p75ECD. Therefore, in an embodiment, the present disclosure provides a method of treating or preventing cerebral amyloid angiopathy (CAA), comprising administering to a subject in need thereof a therapeutically effective amount of p75 extracellular (p75ECD).

While not wanting to be bound by theory, it is believe that tauopathies are a class of neurodegenerative diseases associated with the pathological aggregation of defective, hyperphosphorylated tau protein in the brain that are referred to as neurofibrillary tangles (NFT). Tauopathies may include any neurodegenerative disease with hyperphosphorylation of the tau protein including AD, Parkinson's disease, motor neuron disease, frontotemperal degeneration, Huntington's Disease and Pick's Disease. As disclosed herein, it has been found that administration of p75ECD reduced tau phosphorylation at multiple sites for example at serine 396, 262, 199 and threonine 231. Accordingly, in an embodiment, the present disclosure provides a method of treating or preventing a tauopathy, comprising administering to a subject in need thereof a therapeutically effective amount of p75 extracellular domain (p75ECD).

The term "treating" as used herein is intended to mean that the administering of the p75ECD reduces or ameliorates at least some of the signs or symptoms of AD, CAA or tauopathy.

The term "preventing" as used herein is intended to mean that the administering of the p75ECD occurs prior to diagnosis of AD, CAA and/or tauopathy, and reduces, ameliorates or delays onset of at least some of the signs or symptoms of ADD, CAA and/or tauopathy; or otherwise means that the administering of the p75ECD prevents the signs or symptoms of ADD, CAA and/or tauopathy from worsening. The term "preventing" is therefore intended to include prophylactically treating.

The p75ECD administered can be from any species of interest (eg humans, mouse, rat, rabbit, cat, dog, goa, cow, horse, non-human primates, etc). However, in an embodiment, the p75ECD is human p75ECD. In an embodiment, the p75ECD can have the nucleotide sequence provided in SEQ ID NO: 3 or the amino acid sequence provided in SEQ ID NO: 4.

In an alternative embodiment, the p75ECD can be a functional fragment, variant, analogue or derivative of this sequence. For example, variants, analogues or derivatives of the p75ECD (or a functional fragment thereof) consist of a molecule that differs from the p75ECD (or functional fragment thereof) but retains similarity in biological activity to p75ECD, in particular the ability to bind to proneurotrophins and the Aβ peptide. A variant, analogue or derivative of the p75ECD (or a functional fragment thereof) may have substantial overall structural similarity with the p75ECD (or functional fragment thereof) or only structural similarity with one or more regions of the p75ECD (or functional fragment thereof) responsible for the biological activity. Typically, a variant, analogue or derivative will be provided by, or be the result of, the modification of one or more amino acids from the relevant amino acid sequence. For example, a variant, analogue or derivative of a functional fragment comprising the sequence provided in SEQ ID NO: 4, will be provided by, or be the result of, the addition of one or more amino acids to that amino acid sequence, the deletion of one or more amino acids from that amino acid sequence, and/or substitution of one or more amino acids from that amino acid sequence. Inversion of amino acids and other mutational changes that result in the alteration of the amino acid sequence are also encompassed. Such an analogue or derivative may be prepared by introducing a nucleotide change(s) into a polynucleotide molecule such that the desired amino acid change(s) are achieved upon expression of the mutagenised polynucleotide molecule, or by otherwise synthesising an amino acid sequence incorporating the desired amino acid change(s). The substitution of an amino acid may involve a conservative or non-conservative amino acid substitution. By conservative amino acid substitution, it is meant that an amino acid residue is replaced with another amino acid having similar characteristics and which does not substantially alter the biological activity of the peptide or polypeptide. Exemplary conservative amino acid substitutions are provided in Table 1 below. Particular conservative amino acids envisaged are: G, A, V, I, L, M; D, E; N, Q; S, T; K, R, H; F, Y, W, H; and P, Na-alkylamino acids may have minor variation(s) in the sequence which do not result in any substantial decrease or variation in biological activity. These variations may include conservative amino acid substitutions such as: Gly, Ala, Val, Ile, Leu, Met; Asp, Glu, Asn, Gln; Ser, Thr; Lys, Arg, His; Phe, Tyr, Trp, His; and Pro, Na-alkylamino acids; and non-conservative amino acid substitutions.

TABLE 1

Exemplary conservative amino acid substitutions

Conservative Substitutions

| | |
|---|---|
| Ala | Val*, Leu, Ile |
| Arg | Lys*, Gln, Asn |
| Asn | Gln*, His, Lys, Arg, Asp |
| Asp | Glu*, Asn |
| Cys | Ser |
| Gln | Asn*, His, Lys, |
| Glu | Asp*, γ-carboxyglutamic acid (Gla) |
| Gly | Pro |
| His | Asn, Gln, Lys, Arg* |
| Ile | Leu*, Val, Met, Ala, Phe, norleucine (Nle) |
| Leu | Nle, Ile*, Val, Met, Ala, Phe |
| Lys | Arg*, Gln, Asn, ornithine (Orn) |
| Met | Leu*, Ile, Phe, Nle |
| Phe | Leu*, Val, Ile, Ala |
| Pro | Gly*, hydroxyproline (Hyp), Ser, Thr |
| Ser | Thr |
| Thr | Ser |
| Trp | Tyr |
| Tyr | Trp, Phe*, Thr, Ser |
| Val | Ile, Leu*, Met, Phe, Ala, Nle |

*indicates preferred conservative substitutions

Where an analogue or derivative is prepared by synthesis, the analogue or derivative may include an amino acid or amino acids not encoded by the genetic code, such as carboxyglutamic acid and hydroxyprolin, or D-amino acids instead of L-amino acids may be included. As such the analogue or derivative may be a mimetic of the p75ECD (or functional fragment thereof) such as a peptido-mimetic. However, it is not necessary that an analogue or derivative of the p75ECD (or functional fragment thereof) have amino acid sequence identity and/or similarity and, indeed, an analogue or derivative may not be proteinaceous at all.

It is to be understood that peptides encoded by amino acids sequences that have minor variations from the amino acid sequences provided in SEQ ID NO: 4 and SEQ ID NO: 6 may still fall within the scope of the invention, provided said peptides are capable of binding to p75 and preventing signalling through the p75. In particular, natural variants (or isoforms) of p75ECD, or p75ECD peptides derived from non human species are to be considered to fall within the scope of the p75ECD or p75ECD-Fc fusion peptides of the disclosed methods.

In an embodiment, the p75ECD comprises a p75ECD fusion wherein the p75ECD is fused to a fusion partner. The fusion partner may be any suitable fusion partner known to those skilled in the art such as the Fc region of an immunoglobulin, human serum albumin (HSA), and bovine serum albumin (BSA), etc, provided that the p75ECD retains at least some of its biological activity. The fusion product may be produced by expressing the product from a suitable construct encoding the fusion product or by otherwise by chemically linking the p75ECD to the fusion partner. The fusion partner should improve the stability and serum half-life of the p75ECD in vivo. In an embodiment, the p75ECD is fused to a Fc domain of an immunoglobulin, to form a p75ECD-Fc fusion. The Fc domain can be any suitable Fc domain from any suitable immunoglobulin. However, in a preferred embodiment, the Fc domain is from human IgG.

In an embodiment, the Fc region is capable of dimerising to produce a dimeric form of the p75ECD. However, other fusion partners may be capable of forming other types of oligomers, such as trimers, quadrimers, pentamers, etc. Accordingly, the p75ECD may be an oligomer, such as a dimer, trimer, quadrimer, pentamer, etc. In an embodiment, the p75ECD may be a dimer. In an embodiment, the p75ECD-Fc fusion may be a p75ECD-Fc dimer.

In an embodiment, the p75ECD-Fc fusion comprises a human p75ECD molecule linked to a Fc portion of a human IgG1. Those skilled in the art will appreciate that such a fusion could have a number of different nucleotide and amino acid sequences, for example, depending upon the linker used. However, in an embodiment, the nucleotide sequence of a human p75ECD-human IgG1 Fc domain fusion (human p75ECD-Fc) is provided in SEQ ID NO: 5.

Similarly, in an embodiment, the amino acid sequence of a human p75ECD-Fc fusion is provided in SEQ ID NO: 6. In an embodiment, SEQ ID NO: 6 comprises a p75ECD peptide at amino acid residues 1-169 of SEQ ID NO: 6, followed by a linker "DKTHTCPPCP" at residues 170 to 179, followed by an Fc domain at residues 180 to 396. However, it will be appreciated that the p75ECD-Fc fusion may be a functional fragment, variant, analogue or derivative of the sequence provided by SEQ ID NO: 6. Functional fragments, variants, analogues or derivatives are described elsewhere herein.

In an embodiment, the p75ECD or p75ECD fusion is administered to the subject as a nucleotide molecule. Such a polynucleotide molecule may consist in, for example, an expression vector or expression cassette. Amongst preferred expression vectors are viral vectors capable of effecting transduction of a desired host cell type(s), for example retroviral vectors, adenovirus vectors and vectors derived from adeno-associated viruses (AAV), such as those well known to those skilled in the art. Viral vectors comprising a nucleotide sequence encoding p75ECD or p75ECD fusion of the present disclosure, may be used to provide an in vivo source of the p75ECD or p75ECD fusion at a desired site for the treatment or prevention of a neurological disorder.

In a preferred embodiment, the p75ECD or p75ECD fusion is administered by a virus vector that is known to provide a means for delivering a nucleotide into a cell in a manner that is suitable for gene therapy. Adeno-associated virus (AAV) vector, lentiviral vectors, or Herpes Simplex viral vectors could be used as a viral vector as would be understood by those skilled in the art, as they are all capable of delivering a nucleotide to a cell for the purpose of gene therapy. The delivery of p75ECD or p75ECD fusion via a viral vector may mediate long term expression of the agent in the CNS (e.g. the brain), and the on-going secretion of p75ECD or p75ECD fusion is desirable given the chronic nature of many neurological disorders. The use of an AAV vector in an embodiment is advantageous inasmuch as the vector may be administered as a single injection (e.g. an intracranial or interventricular injection), may provide long term secretion of the agent, and additionally, is also considered as being very safe with no pathological events ever having been reported in animals or humans. AAV vectors are known as a means for gene therapy delivery. Accordingly, in an embodiment, the virus vector may be a AAV vector. The AAV vector may be any suitable adeno-associated virus vector known to those skilled in the art, for example, AAV1, AAV2, AAV4, AAV5, AAV6, AAV7, AAV8, AAV9, AAV10, AAV11, AAV12, etc. In an embodiment, the AAV vector is AAV8.

The "therapeutically effective amount" will be any amount that will elicit a beneficial or therapeutic effect in the subject. In an embodiment, the dosage for an AAV vector for any suitable subject is between $1\times10^6$ and $6\times10^{13}$ viral genomes/kg body weight of the subject. In an embodiment, the dosage for an AAV vector for any suitable subject is between $1\times10^{11}$ and $6\times10^{12}$ viral genomes/kg body weight of the subject.

The dosage of an adeno-associated virus vector administered can vary as would be well appreciated by those skilled in the art. For example, for human subjects, a "safe" dosage used in patients in clinical trials on a service of the U.S. National Institutes of Health is $6\times10^{12}$ viral genomes (vg)/kg body weight. However, the dosage of the adenovirus vector administered to a human subject for the method described herein may range from $1\times10^6$ to $6\times10^{13}$ vg/kg body weight. In an embodiment, the dosage of the adenovirus vector administered to a human subject is between $1\times10^{10}$ to $6\times10^{12}$ viral genomes/kg body weight. In an embodiment, the dosage of the adenovirus vector administered to a human subject is between $1\times10^{11}$ and $3\times10^{12}$ viral genomes/kg body weight. In an embodiment, the dosage of the adenovirus may be higher, for example, $1\times10^{14}$, $1\times10^{15}$, $1\times10^{16}$, $1\times10^{17}$, $1\times10^{18}$, $1\times10^{18}$, $1\times10^{19}$, $1\times10^{20}$, etc, providing that these dosages are considered safe.

The dosages of AAV vectors used in human subjects can be converted to an appropriate dosage for other animals using US Food and Drug Administration (FDA) criteria for converting drug equivalent dosages across species, based on body surface area [human equivalent dose in mg/kg=animal dose in mg/kg×(animal weight in kg/human weight in kg) 0.33] (Food and Drug Administration, 2003). Accordingly, a "safe" dose in a mouse may be $8\times10^{10}$ viral genomes. However, those skilled in the art would appreciate that the dosage of the adeno-associated virus vector administered to a mouse subject may range from $1\times10^5$ to $1\times10^{13}$ viral genomes. In an embodiment, the dosage of the adeno-associated virus vector administered to a mouse subject may range from $1\times10^8$ to $1\times10^{12}$ viral genomes. In an embodiment, the dosage of the adeno-associated virus vector administered to a mouse subject may range from $1\times10^9$ to $1\times10^{11}$ viral genomes.

In an embodiment of this aspect of the disclosure, the p75ECD or p75ECD-Fc fusion is a recombinant peptide. The recombinant p75ECD or p75ECD-Fc fusion peptide can be produced using any suitable techniques known to those skilled in the art, for example, by expression in a cultured bacterial system (eg in *Escherichia coli*), yeast expression system, insect expression system, viral expression system, or in eukaryotic cell expression system, or the peptide could be artificially synthesised, etc, all of which would be known to the person skilled in the art.

In an embodiment, the dosage of recombinant p75ECD or p75ECD-Fc fusion peptide administered may be any suitable amount that will elicit a beneficial or therapeutic effect in the subject, and may vary according to administration route. In an embodiment, the dosage will be about 0.01 to about 500 mg/kg of the subject body weight per day which can be administered in single or multiple doses. Preferably, the dosage will be about 0.1 to about 250 mg/kg per day; more preferably, about 0.5 to about 20 mg/kg per day.

In an embodiment, the p75ECD, p75ECD fusion, p75ECD-Fc or AAV-p75ECD-Fc of this aspect of the disclosure is provided in combination with a pharmaceutically-acceptable carrier, excipient and/or diluent. Suitable pharmaceutically-acceptable carriers, excipients and/or diluents are well known to the person skilled in the art.

The p75ECD, p75ECD fusion, p75ECD-Fc or AAV-p75ECD-Fc of this aspect of the disclosure may be administered to the subject by any suitable route, for example, orally, intravenously, intramuscularly, intraperitoneally, intranasally, intracranially, intrathecally or intraventricularly. However, preferably, the p75ECD or p75ECD-Fc is administered intraperitoneally, intramuscularly, intrathecally or intraventricularly.

In another aspect, there is provided a method of protecting neurons against apoptosis and/or neurodegeneration by blocking signalling through p75 comprising administering to a subject in need thereof a therapeutically effective amount of a p75ECD or analogue thereof. In an embodiment, the p75ECD or analogue thereof prevents binding of neurotoxic molecules selected from the group consisting of Aβ, proNGF, proBDNF, and proNT3 to p75. The method of this aspect uses the embodiments described above.

In a further aspect, there is provided a method of treating and/or preventing a neurodegenerative disorder or tauopathy comprising administering to a subject in need thereof a therapeutically effective amount of a p75 extracellular domain (p75ECD) or analogue thereof, wherein the neurodegenerative disorder or tauopathy selected from Alzheimer's Disease, CAA, amyotrophic lateral sclerosis (ALS), Down Syndrome, Huntington's Disease, Parkinson's Disease, motor neuron disease, multiple sclerosis, amyotrophic lateral sclerosis (ALS), Pick's Disease, progressive supranuclear palsy, corticobasal degeneration, argyrophilic grain disease, tangle-only dementia, white matter tauopathy with globular lial inclusions, frontotemporal dementia and parkinsonism linked to chromosome 17. The method of this aspect uses the embodiments described above.

EXAMPLES

Example 1 Diagnosing and Treating Neurological Disease

Materials and Methods
Reagents and Antibodies

Vectors of AAV8-CBA-p75NTR-ECD-Fc (AAV-ECD-Fc) and AAV8-CBA-GFP (AAV-GFP) were produced and purified by Virovek (Hayward, Calif., USA). pcDNA3-human full length p75NTR was from Dr. Rainer Niedenthal, Institute for Physiological Chemistry/Biochemistry, Hannover Medical School, Hannover, Germany. Synthetic Aβ42 (Cat.No. 62080) and scrambled Aβ42 (Cat.No. 62046) were purchased from American Peptide (Sunnyvale, Calif., USA).

Human p75ECD-Fc and Fc recombinant proteins were prepared as follows. Human p75ECD and Fc nucleotide constructs were individually produced using primers (Table 2) and PCR under standard conditions and using human cDNA as a source of DNA, and then, for the fusion protein of p75ECD-Fc, the fragments were fused together by overlapping PCR using standard conditions.

TABLE 2

PCR primer pair sequences used for human p75ECD-Fc and Fc cloning

| Gene | Primers | Sequences | SEQ ID NO: |
|---|---|---|---|
| p75ECD | Forward | 5'-GCGCTCTAGACCACCATG GGGGCAGGTGCCACCGG-3' | 7 |
| p75ECD | Reverse | 5'-CTCTGTCGACTTATCATT TACCCGGAGACAGGG-3' | 8 |
| Fc | Forward | 5'-AACCATGGGCGACAAAAC TCACACATG-3' | 9 |

TABLE 2-continued

PCR primer pair sequences used for human p75ECD-Fc and Fc cloning

| Gene | Primers | Sequences | SEQ ID NO: |
|---|---|---|---|
| Fc | Reverse | 5'-AAGAATTCTCATTTACCC GGAGACAG-3' | 10 |

Once p75ECD-Fc and Fc constructs were generated, they were cloned into pET-28a(+) vector (Merck Millipore) using Nco-I and EcoR-I restriction enzymes and then transformed into DH10B E. coli competent cells and subsequently transformed into BL21 E. coli competent cells. In order to express p75ECD-Fc and Fc recombinant peptides, BL21 E. coli stock of p75ECD-Fc and Fc was inoculated in a large volume of Luria Broth (LB) culture medium and incubated at 37° C. until OD value reached to 0.4-0.6 and then 1 mM IPTG was used to induce expression of p75ECD and Fc in E. coli for 3 hours at 37° C. E. coli was spun down at 5,000 RPM at 4° C. for 15 min and then pellet was re-suspended in hypotonic lysis buffer (10 mM tris, 2 mM EDTA, 25 mM NaCl, 0.1% Triton X-100, 1-2 mg/ml Lysozyme, pH=8.0) and after sonication supernatant was extracted by high speed centrifuging (15,000 RPM) for 30 min at 4° C. In order to harvest p75ECD-Fc and Fc, the supernatant was passed through protein-G sepharose column and then p75ECD-Fc and Fc were eluted from protein-G sepharose by applying 100 mM glycine pH 2.5. Subsequently, the proteins in glycine solution were dialyzed in PBS at 4° C. and purity of the peptides was confirmed by Coomassie blue staining. P75EC-Fc can also be produced in yeast, mammalian cells and insect cells with routine method of production of any recombinant proteins.

Antibodies used in present study are: anti-p75NTR antibody (rabbit polyclonal, AB1554, Millipore, US), anti-p75ECD antibody (rabbit polyclonal, 9650, a generous gift from Prof. Moses Chao, Department of Cell Biology, Skirball Institute, New York, USA), anti-TACE (ADAM-17) antibody (Rabbit polyclonal, ab2051, Abcom, US, for detection of tumor necrosis factor-alpha converting enzyme), anti-human IgG Fc antibody (mouse monoclonal, MAB1302, Millipore, US, for detection of the p75ECD-Fc), anti-beta amyloid antibody (mouse monoclonal, 6E10, Covance, US), anti-sAPPβ antibody (rabbit polyclonal, SIG-39138, Covance, US), anti-amyloid precursor protein C-terminal antibody (751-770aa) (rabbit polyclonal, 171610, Calbiochem, US, for detection of APP full length and CTFs cleavage products), anti-APP C-terminal (678-695aa) (rabbit polyclonal, 6687, was kindly provided by Prof C. Haass, Ludwig-Maximilians University Munich, Munich, Germany 1), anti-BACE C-Terminal antibody (mouse monoclonal, clone 61-3E7, Millipore, US, for detection of beta-site APP cleaving enzyme), anti-BACE1 extracellular domain antibody (mouse monoclonal, MAB931, R&D, US, for detection of cell BACE1 levels in in vitro study), anti-Neprilysin antibody (rabbit polyclonal, AB5458, Millipore, US), anti-RAGE antibody (rabbit polyclonal, clone DD/A11, Millipore, US, for detection of receptor for advanced glycation end products), anti-LRP (mouse monoclonal, 5A6, Calbiochem, US, for detection of low density lipoprotein receptor-related protein), anti-IDE, N-terminal (97-273) antibody (rabbit polyclonal, PC730, Millipore, US, for detection of insulin degrading enzyme), anti-NeuN antibody (mouse monoclonal, MAB377, Millipore, US, for detection of Neuronal Nuclei), anti-ChAT antibody (rabbit polyclonal, ab137349, Abcam, US, for detection of choline acetyltransferase), anti-MAP2 (mouse monoclonal, 05-346, Millipore, US, for detection of microtubule-associated protein 2), anti-glial fibrillary acidic protein (GFAP) antibody (rabbit monoclonal, 04-1062, Millipore, US, for detection of active astrocytes), anti-active Caspase-3 antibody (rabbit polyclonal, ab13847, Abcam, US, for detection of apoptosis), anti-CD45 antibody (rat monoclonal, ab25386, Abcam, US, for detection of active microglia), anti-SNAP25 antibody (rabbit polyclonal, AB1762, Millipore, US, for detection of synaptosomal-associated protein-25), anti-PSD95 antibody (mouse monoclonal, MAB1596, Millipore, US, for detection of post synaptic density protein 95), anti-SYP antibody (mouse monoclonal, MAB332, Millipore, US, for detection of Synaptophysin), anti-Synapsin I (rabbit polyclonal, 574778, Millipore, US), anti-VAMP1 antibody (rabbit monoclonal, ab151712, Abcam, US, for detection of vesicle-associated membrane protein 1), anti-pS396 antibody (rabbit polyclonal, 11102, Signalway Antibody, US, for detection of tau phosphorylated at serine 396), anti-pT231 antibody (rabbit polyclonal, 11110, Signalway Antibody, US, for detection of tau phosphorylated at threonine 231), anti-pS262 antibody (rabbit monoclonal, ab92627, Abcam, US, for detection of tau phosphorylated at serine 262), anti-pS199 antibody (rabbit monoclonal, ab81268, Abcam, US, for detection of tau phosphorylated at serine 199), anti-total tau antibody (rabbit polyclonal, ab39524, Abcam, US), anti-GSK3 (alpha+beta) (phospho Y279+Y216) antibody (rabbit polyclonal, ab52188, Abcam, US), anti-GSK3β antibody (rabbit monoclonal, ab18893, Abcam, US, for detection of glycogen synthase kinase-3β), anti-GSK3β (phospho S9) antibody (rabbit monoclonal, ab75814, Abcam, US, for detection of glycogen synthase kinase-3β phosphorylated at serine 9), anti-Glyceraldehyde 3-phosphate dehydrogenase (GAPDH) antibody (sheep polyclonal, OSG00034W, Osenses, Australia) and anti-β-Actin antibody (rabbit polyclonal, ab8227, Abcam, US).

Human CSF and Brain Tissue Samples Preparation

The studies on human cerebral spinal fluid (CSF) samples were approved by the Ethics Committee of Daping Hospital of the Third Military Medical University. For CSF sampling, a total of 56 research participants (n=29 for AD, n=27 for ND) were enrolled. Written informed consents to lumbar puncture and CSF sampling were obtained from all participants or their representatives. Diagnosis of AD was made according to the National Institute of Neurological and Communicative Disorders and Stroke (NINCDS-ADRDA) criteria (Raffi, 2013; McKhann et al. 1984), including the Mini-Mental State Examination (MMSE). CSF specimens were collected in sterile glass tube at 8:00 AM after overnight fasting and immediately stored at −80° C. for future biochemical analysis. The studies on human brain samples were approved by the Ethics Committee of University of South Florida (Pro00011605). Post-mortem human brain samples from histologically confirmed cases of Alzheimer's disease and age-matched non-demented individuals were obtained from Banner Sun Health Research Institute (Sun City, Ariz., USA).

Animals

APPswe/PS1DE9 transgenic mice (which are used as a model of AD, and referred to as "AD mice" herein) over express the Swedish mutation of APP and also have PS1 deleted in exon 9, which results in an increase in parenchymal Aβ load with Aβ plaques appearing from the age of four months, glial activation, and deficits in cognitive functions at the age of 6 months demonstrated by radial arm water maze and 12-13 months seen with Morris Water Maze test.

For some experiments, AD/p75−/− and AD/p75+/+ mice were used to investigate the effect of p75 on amyloid precursor protein (APP) processing. Transgenic (Tg) mouse lines expressing APPswe/PS1DE9 (AD) on C57BL/6 background (Castellani and Perry, 2012) and p75−/− (p75NTR/ExonIII−/−) mice on 129sv background were obtained from Jackson Laboratory (number 005864) and bred in the Third Military Medical University Animal House and University of South Australia. In order to obtain AD/p75−/− and AD/p75+/+ mice to investigate the effect of p75 on amyloid precursor protein (APP) processing, the p75−/− mice were crossed with AD mice and after PCR genotyping according to supplier's instructions, the animals subjected to study.

All animals were maintained under standard conditions at 22° C. and a 12 h light/dark cycle with ad libitum food and water. All mice husbandry procedures performed were approved by the Third Military Medical University Animal Welfare Committee and Animal Ethics Committee of South Australian Pathology (16b/12) in accordance with NHMRC guidelines. AD mice were randomly grouped in experiments in vivo.

Measuring the Level of p75ECD in Human Cerebrospinal Fluid (CSF) and Brain and Mouse Brain The level of p75ECD in human CSF (n=29 for AD, n=27 for ND) and human brain tissue samples (n=12 for AD, n=12 for ND) was quantified by ELISA and western blots. ELISA quantification of human p75ECD in CSF was performed using NGF R/TNFRSF16 kit (Cat.No. DY367, R&D Systems, US) according to the manufacturer's instructions. p75ECD of human brain homogenate samples was detected by western blot using anti-NGF receptor p75 (Cat.No. AB1554, Millipore, US). Detection of p75ECD in Tris buffered saline (TBS) fraction of brain homogenates of 12-month old AD mice (Tg) and wild-type littermates (Wt) (n=13 for Tg, n=14 for Wt) were performed using the same protocol.

Measuring TACE Activity in Human and Mouse Brain

Tumor necrosis factor-alpha converting enzyme (TACE) is the main enzyme cleaving p75 and releases p75ECD. TACE activities in human CSF (n=29 for AD, n=27 for ND) were measured with SensoLyte® 520 TACE Activity Assay Kit (Cat.No. 72085, ANASPEC, US). According to manufacturer's instruction, the enzyme activities were monitored at excitation/emission=490 nm/520 nm. TACE expression levels in AD mice brain were also detected with western blot using TACE antibody (Cat.No. ab2051, Abcom, US).

Preparation of Oligomer Form of Aβ42

In the present study, oligomer form of Aβ42 was used. Synthetic Aβ42 and scrambled Aβ42 were prepared following the protocols described previously. In brief, the Aβ42 peptide was dissolved in 1,1,1,3,3,3-hexafluoro-2-propanol (HFIP, Cat.No. 105228, Sigma, US) at 1 mg/ml concentration, and was aliquoted in eppendorf tubes (100 μg/tube). The HFIP was allowed to evaporate in the fume hood and the resulting clear peptide film was dried under vacuum overnight and then pellets were stored at −20° C. until use. For oligomerisation of Aβ42, dried pellets were re-suspended in Dulbecco's Modified Eagle Medium (DMEM) to a final concentration of 100 μM and following incubated at 4° C. for 24 hours. The oligomer form of Aβ42 was checked by western blot before use (Saadipour, K. et al., 2013).

SH-SY5Y Cell Culture and Assays

Human neuroblastoma SH-SY5Y was purchased from Cell Resource Center (CRC) of Peking Union Medical College, and cultured in growth medium consisting in a 1:1 mixture of DMEM/Ham's F-12 supplemented with 10% fetal bovine serum, 2 mM L-glutamine, 1 mM sodium pyruvate, 1% antibiotic-antimycotic mixture in 5% CO2 humidified incubator at 37° C. All in vitro assays were performed at least three times.

To assess the role of p75ECD against Aβ toxicity in vitro, cell viability assay using 3-(4,5-methylthiazol-2-yl)-2,5-diphenyl-tetrazolium bromide (MTT) was performed. After 24 hours grown in 96-well culture plates (50,000 cells/well), SH-SY5Y cells were treated with either 0.3-10 uM Aβ42, or 10 ug/ml recombinant p75ECD-Fc in conjunction with 0.3-10 uM Aβ42 for 24 hour, followed by incubation with 0.5 mg/ml MTT (Cat.No. M5655, Sigma, US) at 37° C. for 4 h. Then, insoluble purple formazan crystals, produced by mitochondrial dehydrogenases in viable cells, were dissolved for 15 min at 37° C. in 100 μl of 10% (w/v) SDS solution in HCl (0.01 M), and the optical density at 563 nm was measured by a microplate reader (Synergy H4, Bio Tek).

To assess the protective effect of p75ECD against neurites collapse, a neurites outgrowth assay was performed. After 24 hours incubation in DMEM/F-12, SH-SY5Y cells were cultured for 7 days in a medium with 1% FBS and 10 μM all-trans-retinoic acid (Cat.No. R2625, Sigma, US) diluted in DMSO, followed by treatment with 5 μM Aβ in the presence or absence of 10 μg/ml recombinant ECD-Fc for 24 hours, and then fixed with 4% paraformaldehyde for 10 min. The total images of 50 neurons from different groups were taken by microscopy and the length of neurites was measured by using ImageJ and data is expressed as mean±s.e.m. and significance was achieved when p<0.05. Variables among groups were determined by one-way ANOVA and Tukey's post-hoc.

To examine the effect of p75ECD on tau-phosphorylation in vitro, SH-SY5Y cells were differentiated in 10 mM all-trans-retinoic acid for 3 days, followed by incubated with different concentrations 0.1 to 10 uM of Aβ42 oligomers in the presence or absence of 10 μg/ml recombinant p75ECD-Fc or rabbit anti-p75ECD antibodies (9650, Professor Moses Chao of New York University) for 24 hours. Cell lysates were subjected to Western blot with pS262 antibody (Cat.No. ab92627, Abcam, US), total-tau antibody (Cat.No. ab39524, Abcam, US), GSK3 (α+β) antibody (Cat.No. ab52188, Abcam, US), pSer9 GSK3β antibody (ab75814, Abcam, US) and GAPDH antibody (Cat.No. OSG00034W, Osenses, Australia) as a loading control.

Primary Cortical Neuron Cultures and Assays

Cortical neurons were isolated from a day old 129sv mice brain and cultured on poly-D-lysine (Cat.No. P7280, Sigma, US) precoated coverslips. Twenty four hours after seeding, the neurons were treated with 5 μM Aβ42 oligomers in the presence of absence of recombinant p75ECD-Fc (10 μg/ml) for 24 hour and then neurons fixed with 4% paraformaldehyde for 10 min and followed with DAPI (Cat.No. D9542, Sigma, US) and MAP-2 (Cat.No. 05-346, Millipore, US) staining. The neurites images were collected and analysed in the way described above.

In order to investigate the effects of Aβ on TACE expression, cortical neurons from a day old 129sv mice were isolated and cultured in 6 well plates and 72 hours after seeding, the neurons were incubated with 0.3, 1, 3 and 10 μM concentrations of Aβ42 oligomer for 24 hours and then the cell lysate harvested in RIPA buffer containing protease inhibitors cocktail. The cells lysates were sonicated and then centrifuged at 14,000 rpm for 10 min at 4° C. and total protein concentration of supernatants were determined using BCA protein assay Kit (Thermo Scientific, Rockford, USA) and 30 μg of total protein subjected to western blot with TACE antibody (Cat.No. ab2051, Abcom, US,) in order to quantify the expression level of TACE protein.

In order to elucidate whether Aβ mediates the amyloidogenic processing of APP via p75, cortical neurons from a day old AD/p75−/− and AD/p75+/+ mice which carry an overexpressed APPswe/PS1DE9 with/without p75 genes, were isolated and cultured into 6 well plates and 72 hours after seeding, the neurons were treated with 0.1 and 0.3 μM Aβ42 oligomer for 24 hours and then the cell lysate harvested in RIPA buffer and subjected to western blot to quantify endogenous APP with APP antibody (Cat.No. 171610, Calbiochem, US), sAPPβ antibody (Cat.No. SIG-39138, Covance, US) and BACE1 antibody (Cat.No. MAB931, R&D, US).

AAV-ECD-Fc Vector Production and Purification

Recombinant baculoviruses were generated using the Bac-to-bac system according to the manufacturer's protocol (Invitrogen). First, pFastBac shuttle plasmids containing target gene were used to transform DH10Bac competent bacteria respectively and two recombinant Bacmid clones (white colonies) from each construct were selected and DNA "minipreps" were prepared using standard techniques. Then the DNA minipreps were used to transfect Sf9 cells to generate recombinant baculoviruses. The recombinant baculoviruses were amplified once and used for AAV production. Specifically, Sf9 cells were cultured to about $1\times10^7$ cells/ml and diluted to about $5\times10^6$ cells/ml. The diluted Sf9 culture at 200 ml volume was double-infected with a helper recombinant baculovirus containing the AAV Rep and Cap genes and second recombinant baculovirus containing the target gene for AAV vector production. Three days post infection, the Sf9 cells were harvested and lysed in SF9 lysis buffer (50 mM Tris-HCl, pH7.8, 50 mM NaCl, 2 mM $MgCl_2$, 1% Sarkosyl, 1% Triton X-100, and 140 units/ml Benzonase). Genomic DNA was digested by incubation at 37 C for one hour. Cell debris was removed by centrifugation at 8,000 rpm for 30 min. The cleared lysates were loaded onto CsCl step-gradient and subjected to ultracentrifugation at 28,000 rpm for 20 hours. The viral band was drawn through a syringe with an 18-gauge needle and loaded onto a second CsCl and subjected to linear-ultracentrifugation at 65,000 rpm for 20 hours. Then the viral band was drawn and passed through two PD-10 desalting columns (GE HealthCare) to remove the CsCl and detergents and at the same time exchanged to PBS buffer containing 0.001% pluronic F-68. Quantitative real-time PCR (qPCR) was performed to determine the AAV vector genome copy numbers using QPCR primers corresponding to the target gene.

A plasmid containing the full length p75 (NM_002507) purchased from American Type Culture Collection (ATCC) and a plasmid containing p75-ECD-Fc were provided to Virovek, and p75ECD-Fc was inserted into a AAV8 vector (provided by Virovek), which contained an AAV8 capsid sequence with an AAV2 phospholipase domain to enhance the potency of AAV8. The sequence of the AAV8 capsid sequence with the AAV2 phospholipase domain is provided in SEQ ID NO: 13, wherein the AAV2 phospholipase domain sequence comprises nucleotides 26 to 431. The AAV-ECD-Fc vector was generated, produced and purified by Virovek. Briefly, the target gene was cloned into Virovek's AAV production shuttle plasmid. Recombinant baculo-virus was generated and used to infect Sf9 cells to produce AAV vectors with Virovek's proprietary BAC-TO-AAV technology. The AAV vectors were purified by double CsCl ultracentrifugations and buffer-exchanged with PD-10 desalting columns. AAV titres were determined with quantitative real-time PCR method and the purity was verified by SDS-PAGE following SimplyBlue Safestain assay (FIG. 1). The p75-ECD fragment was PCR amplified using the p75 plasmid as template and the primers provide in SEQ ID NO: 7 and SEQ ID NO: 8. The Fc fragment was PCR amplified using p75-ECD-Fc as template and the primers provided by SEQ ID NO: 11 and 12. The PCRs were conducted under standard conditions.

Intraventricular Injection

APP/PS1 transgenic mice were injected with AAV-ECD-Fc or AAV-GFP into the left lateral ventricle once at 3 months of age for "prevention" or at 9 months of age for "treatment" of AD. The injection coordinate point was taken from bregma following the Stereotaxic Coordinates: anteroposterior, −0.6 mm; lateral, 1.2 mm; and ventral, 2.2 mm. The AAV dosage of injection was $8 \times 10^{10}$ viral genomes, converted from the safe dosage used in patients on a service of the U.S. National Institutes of Health (ClinicalTrials.gov), according to the US Food and Drug Administration (FDA) criteria for converting drug equivalent dosages across species, based on body surface area [human equivalent dose in mg/kg=animal dose in mg/kg×(animal weight in kg/human weight in kg) 0.33] (Food and Drug Administration, 2003).

Behavioural Phenotyping

The operators and investigators were fully blinded to group and intervention information. All animals were subjected to behavioural tasks at 12 months of age, including Morris water maze, Y-maze and open field. Morris water maze test was conducted following the protocol reported previously with minor modification (Wang Y. J. et al., 2010; Yau J. L. et al., 2007; Markowska, A. L et al., 1993). Briefly, it consisted of four platform trials per day for 4 consecutive days, followed by a probe trial. Performance was video-recorded and analysed by an image analysing software (ANY-maze, Stoelting). In platform trials, distances of path and latency were measured; and in probe trials, quadrant time and annulus crossings were measured (Markowska, A. L et al., 1993). Spontaneous alternation test and novel arm exploration were performed in Y-maze. For spontaneous alternation test, mice were allowed to move freely through the maze during a 5 min session. Alternation was defined as successive entries into the three arms on overlapping triplet sets (Sarter, M. et al., 1988). The percentage alternation was calculated as the ratio of actual (total alternations) to possible alternations (defined as the number of arm entries minus two), multiplied by 100. For the novel arm exploration, mice were placed at the end of a chosen start arm (home arm) and allowed to explore the maze for 5 min with one of the arms blocked (novel arm) (Jung, W. R et al., 2008). After 2 hours interval, mice were allowed to explore freely all three arms. The novel arm entries and time spent in the novel arm was calculated as a percentage of the total time in all three arms during the 3 min retrieval trial. For open-field test, each mouse was placed in the center of the open field apparatus (Dellu, F. et al., 1992; Conrad, C. D et al., 1999). Paths were tracked using a computer tracking system (Limelight, ActiMetrics) for 3 min. Moreover, rearing, grooming, defecation and urination were recorded.

Tissue Sampling

Animals were humanely killed by overdosing with 6% chloral hydrate (6 ml/kg). Blood was sampled from the right atrium of the heart, followed by intracardial perfusion with 100 ml of 0.1% $NaNO_2$ in normal saline. Brains were isolated and weighed on a digital electronic balance with a readability of 1 mg (BX-420H, Shimadzu Scientific Instruments). Right brain hemisphere for histological analysis was fixed in 4% paraformaldehyde (pH 7.4), for 24 h and incubated for 24 h in 30% sucrose for subsequent cryoprotection. Coronal sections of the brain were cut at 35 μm thicknesses with a cryosectioning microtome and stored at 4° C. in PBS containing 0.1% sodium azide until use. Left brain hemisphere was snap frozen in liquid nitrogen and stored at −80° C. for future biochemical analysis.

Analysis of p75ECD-Fc Expression

The expression of p75ECD-Fc in AD mice brain after intraventricular injection of AAV-ECD-Fc was examined by ELISA, western blot and immunohistochemistry. For ELISA, fresh brain was weight and homogenized in TBS. Homogenates were centrifuged at 10,000×g for 10 minutes at 4° C., and the resultant supernatant was collected. p75ECD-Fc in TBS was detected as above. For Western blot, 10 μl TBS fractions of brain extracts mixed with an equal volume of 2× loading sample buffer were loaded and electrophoresed on 10% SDS-PAGE gels. Gels were transferred to nitrocellulose membranes and then incubated with anti-human IgG Fc (Millipore) or anti-NGF receptor p75 (Millipore) followed by IRDye 800CW secondary antibodies (LI-COR) and scanned by using the Odyssey fluorescent scanner. For immunohistochemistry, tissue sections were stained using anti-human IgG Fc (Cat.No. MAB1302, Millipore, US) following the free-floating immunohistochemistry protocol as described previously (Wang Y. J. et al., 2009b). Immunofluorescence was performed to examine the colocalization between ECD-Fc and neuron, or astrocyte, or microglia, using human IgG Fc antibody (Cat.No. MAB1302, Millipore, US) for p75ECD-Fc, NeuN antibody (Cat.No. MAB377, Millipore, US) for neuron, GFAP antibody (Cat.No. 04-1062, Millipore, US) for astrocyte, CD45 antibody (ab25386, Abcam, US) for microglia. Sections were observed with confocal fluorescence microscope (Radiance 2000MP, Bio-Rad).

Pathology and Quantitative Image Analysis

For the compact Aβ plaque staining, a series of sections was mounted and stained with Congo red (Cat.No. C6277, Sigma, US). In brief, a series of five equally spaced tissue sections (~1.3 mm apart) spanning the entire brain were treated with working sodium chloride solution (containing sodium chloride saturated in 80% alcohol and 0.01% sodium hydroxide) at room temperature for 20 minutes, then placed directly into working Congo red solution (containing saturated Congo red in working sodium chloride solution) for 45 minutes, and dehydrated rapidly in absolute alcohol. Images were collected at 4× magnification using constant bulb temperature and exposure, with all images acquired in the same session. The staining for total Aβ, microgliosis, astrogliosis, and microhemorrhage was processed as described previously (Wang, Y. J. et al., 2009b). Briefly, the sections were randomly selected and stained using free-floating immunohistochemistry for total Aβ (Cat.No. 6E10, Covance, US), microglia (Cat.No. ab25386, Abcam, US), astrocyte (Cat.No. 04-1062, Millipore, US), and tau phosphorylation (pS396 antibody, Cat.No. 11102, Signalway Antibody, US), respectively. Sections were incubated overnight with primary antibodies at 4° C. and further developed with biotinylated secondary antibodies and the ABC kit (Cat.No. PK6200, Vector Laboratories, US) using diaminobenzidine and glucose oxidase as substrates. The area of neocortex and hippocampus was selected for automatic quantification by Image J of Aβ, microglia, astrocyte immunostaining, and Congo red-positive Aβ plaque, yielding the area fraction of the total positive staining against the area of tissue analysed. The average of the individual measurements was used to calculate group means and s.e.m.

For the cerebral amyloid angiopathy (CAA) staining, a series of five consecutive sections were stained by using the Congo Red method. Microhemorrhage staining and quantification were performed following the method described before (Wang, Y. J. et al., 2009a). In brief, a series of five sections were mounted on the slides and stained for hemosiderin using 2% potassium ferrocyanide (Cat.No. 455989, Aldrich, US) in 2% hydrochloric acid for 15 min, followed by a counterstain in a 1% Neutral Red (Cat.No. N4638, Sigma, US) solution for 10 min at room temperature. Microhemorrhage profiles were counted on all sections of each brain under microscopy, and the average number of hemosiderin deposits was calculated per each section. All image analyses were processed in a blind manner.

Colocalization of Aβ Plaque with ECD-Fc

A series of three equally spaced tissue sections covering the hippocampus per animal of eight mice were stained by immunohistochemistry or immunofluorescence. For immunohistochemistry, sections were stained using Congo Red followed by incubation with anti-human IgG Fc. For immunofluorescence, sections were stained using thioflavin S (Cat.No. T3516, Sigma, US) and anti-human IgG Fc and observed with confocal fluorescence microscope (Radiance 2000MP, Bio-Rad).

ELISA Quantification for Aβ

ELISA analysis of the brain Aβ was processed as described previously (Wang Y. J. et al., 2009b). Briefly, frozen brain was homogenized and sonicated in TBS containing protease inhibitors. Homogenates were centrifuged at 100,000 g for 1 h at 4° C., and the resultant supernatant was collected, representing the TBS-soluble fraction. The resultant pellet was suspended and sonicated in water containing 2% SDS and protease inhibitors. The SDS solubilized homogenates were centrifuged at 100,000×g for 1 h at 4° C., and the resultant supernatant was collected, representing the SDS-soluble fraction. The resultant pellet was then extracted in 70% formic acid (FA) and centrifuged, and the resultant supernatant was collected, representing the FA-insoluble fraction. Before ELISA assay, formic acid extracts were neutralized by 1:20 dilution into 1 M Tris phosphate buffer (pH 11) and then diluted in sample buffer. Concentrations of Aβ40 and of Aβ42 in brain extract and serum were quantitatively measured by ELISA according to the manufacturer's instructions (SIG-38954 for Aβ40 and SIG-38956 for Aβ42, Covance, US). Using the wet weight of brain tissue in the original homogenate, the final values of brain Aβ were expressed as Pico moles per gram wet weight of brain.

β-Secretase Activity Analysis

β-secretase activity was measured according to the manufacturer's protocols (Cat.No. K360-100, Bio Vision, US). Briefly, the fresh brain tissues were pulverized in liquid nitrogen, and aliquoted for secretase assays. Secretases were extracted in the extraction buffer provided in the product kits, and their activities were measured by adding a secretase-specific peptide conjugated to the reporter molecules EDANS and DABCYL. Cleavage of the peptide by the secretase physically separates the EDANS and DABCYL, allowing for the release of a fluorescent signal, which is proportional to the level of secretase enzymatic activity. The fluorescent signal was read at an excitation wavelength of 355 nm and emission at 510 nm with a 495 nm cutoff.

Analysis of Neuronal Apoptosis

To assay apoptotic cells, TUNEL staining and immunofluorescence with anti-activated caspase-3 were used. Five sections per animal were used for the TUNEL or activated caspase-3 staining. For TUNEL staining, apoptotic cells in 35 μm formalin-fixed coronal brain sections were labelled using the in situ Death Detection Kit, POD (Cat.No. 11684817910, Roche) according to the manufacturer's instructions. Sections were mounted on slide and dry in fume hood, and then incubated with blocking solution for ten mins at room temperature, and washed twice with PBS. After 2 min incubation in permeabilisation solution on ice, sections were rinsed twice with PBS, dry area around sections. TUNEL reaction mixture was added to sections and incubated in a humidified chamber at 37° C. for 60 min in a humidified in the dark. The slides were rinsed three times with PBS and Converter-POD was added to the sections. After 30 min incubation at 37° C., DAB (3,3'-diaminobenzidine) substrate or alternative POD substrates were added to the sections and incubated for 10 min at room temperature. For immunofluorescence staining, briefly, sections were rinsed in PBS-Tween 20 for 3×2 min and incubated with 3% BSA in PBS for 30 min at room temperature, and incubated with the primary antibody against active caspase-3 (Cat.No. ab13847, Abcam, US) overnight at 4° C., the rinsed twice with PBS and incubated with Alexa Fluor® secondary antibody in PBS for 60 min at room temperature. Sections on slides were protected from light with a black box, rinsed in PBS for 3×5 min and coverslipped with anti-fade mounting medium. Sections were observed with confocal fluorescence microscope (Radiance 2000MP, Bio-Rad).

Quantification of Dendritic Spines by Golgi Stain

Animals were anesthetized by 6% chloral hydrate (6 ml/kg) and perfused intracardially with 0.9% sodium chloride containing 0.5% sodium nitrite followed by 4% formaldehyde. The mouse brains were further perfused with the Golgi dye solution containing 5% potassium dichromate, 5% chloral hydrate, and 4% formaldehyde. After perfusion, the brains were dissected into 0.1 cm×0.1 cm sections and transferred to a 50 ml opaque vial containing Golgi dye solution for three days at room temperature, followed by immersion in 1% silver nitrate solution for another three days in the opaque vial. The brains were serially sectioned in 35 μm thick sections using a vibrate microtome (Leica, VT1000 S, Germany). The number of dendritic spines was estimated at high magnification (1000×) by a researcher who was blind to the injection conditions.

Protein Blotting

The levels of full length p75 (p75FL), p75ECD, the molecules involving Aβ production and degradation, tau phosphorylation and synaptic proteins (SNAP25, synapsin 1, VAMP1 and PSD95) related to synaptic plasticity were analysed using Western blotting. Proteins in the animal brain homogenate were extracted with RIPA buffer including 50 mM Tris (pH 7.4), 150 mM NaCl, 1% Triton X-100, 1% sodium deoxycholate, 0.1% SDS, 2 mM sodium pyrophosphate, 1 mM EDTA, 25 mM β-glycerophosphate, 1 mM Na3VO4, 0.5 μg/ml leupeptin 1-2 mM PMSF, based on the ratio of adding 9 μl RIPA buffer per microgram brain tissue. Samples were subjected to SDS-PAGE (8-15% acrylamide) gels. Separated proteins were transferred to nitrocellulose membranes. The blots were probed with the following antibodies: anti-APP C-Terminal (171610, Calbiochem, US) which recognizes APPfl, CTFβ and CTFα, anti-BACE1 (clone 61-3E7, Millipore, US), anti-Neprilysin (Cat.No. AB5458, Millipore, US), anti-RAGE (clone DD/A11, Millipore, US), anti-LRP (5A6, Calbiochem, US), anti-IDE (PC730, Millipore, US), anti-phospho-tau including pS396 (Cat.No. 11102, Signalway Antibody, US), pT231 (Cat.No. 11110, Signalway Antibody, US), pS199 (Cat.No. ab81268, Abcam, US), pS262 (Cat.No. ab92627, Abcam, US), anti-SNAP25 (Cat.No. AB1762, Millipore, US), anti-Synaptophysin synaptophysin (Cat.No. MAB332, Millipore, US), anti-Synapsin synapsin I (Cat.No. 574778, Millipore, US), anti-VAMP1 (ab151712, Abcam, US); anti-PSD95 (MAB1596, Millipore, US), anti-β-actin (ab8227, Abcam, US). The band density was normalized to that of β-actin. The membranes were incubated with IRDye 800CW secondary antibodies (LI-COR) and scanned using the Odyssey fluorescent scanner.

ELISA Quantification of L-6, IL-1β, INF-γ and TNF-α Concentration

The levels of IL-6, IL-1β, INF-γ, TNF-α in TBS fraction of brain extracts and serum were quantitatively measured using BMS603, BMS6002, BMS606, BMS607 ELISA according to the manufacturer's instructions (eBioscience), respectively. Using the wet weight of brain tissue in the original homogenate, the final values of brain IL-6, IL-1β, INF-γ, TNF-α were expressed as Pico moles per gram wet weight of brain.

Statistical Analysis

No data were excluded from the statistical analysis. For data collection, all samples were coded and analysing researchers were blinded for the identity of the samples.

Unless otherwise stated, the data in the text and figures are expressed as mean±s.e.m. Statistical comparisons between groups were assayed using Tukey's test, Students t-test, one-way ANOVA, or two-way repeated-measures ANOVA for testing the significance of values. Spearman's rank correlation coefficient was used to evaluate the correlation of p75ECD level with Aβ burden, inflammation and behavioural performance. P values<0.05 were considered significant. All these analyses were performed using SPSS for Windows version 13.0.

Results

Figure 2:
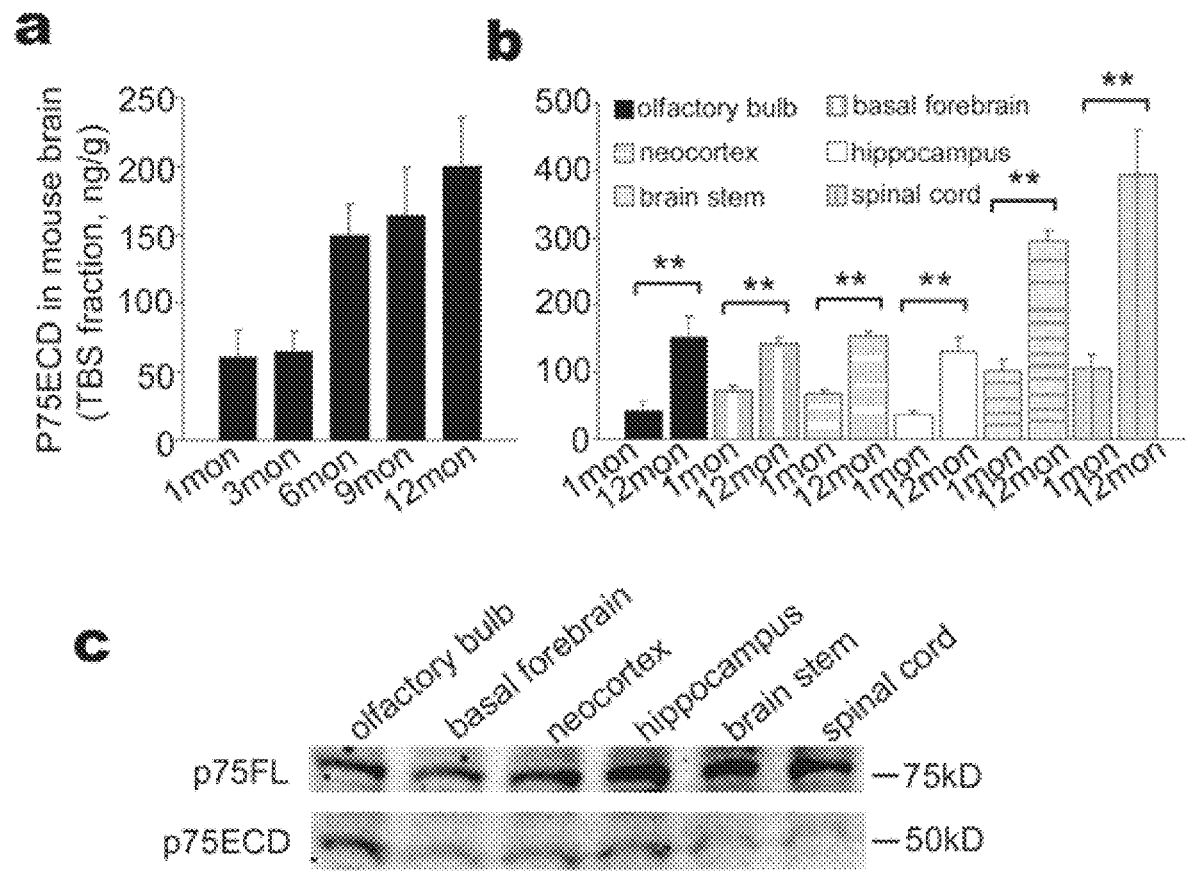
FIG. 2 provides evidence of physiological levels of p75ECD in the central nervous system, specifically (a) graphical representation of ELISA analysis of p75ECD in the TBS fraction of whole brain homogenate of Wt mice of different ages, (mon=months; n=7), (b) p75ECD levels in different brain regions of 1-month old and 12-month old Wt mice (n=5, mean±s.e.m., Student's t-test, **$P<0.01$), (c) Western blot analysis of p75FL and p75ECD in different brain regions of 12-month old Wt mice.

Shedding of p75ECD is Down-Regulated in the Brains of AD Subjects and APPswe/PS1dE9 Mice The levels of p75ECD in the whole brain or different regions increased with age in Wt mice (FIG. 2a, b). Soluble p75ECD was present in many different regions of the brain (FIG. 2b, c), peripheral ganglia and organs (data not shown) of wild-type (Wt) mice. The data indicate that shedding of the p75 ECD is a physiological process and is associated with aging in normal, non-demented control individuals.

The p75ECD level was measured in the cerebrospinal fluid (CSF) from AD patients and ND controls by ELISA. The sensitivity of p75ECD ELISA reached 150 pg/ml and it is specific as verified by Western blots on the same samples (r=0.8198, p<0.0001) (data not shown). The p75ECD level in the cerebrospinal fluid (CSF) of AD patients (n=29) was significantly lower than that in the CSF of ND controls (n=27, P<0.01) (FIG. 3a). The mean±s.e.m p75ECD concentration in CSF for non-demented controls was 864±30 pg/ml, and the range was from 549 to 1233 pg/ml. The mean±s.e.m p75ECD concentration for AD patients in CSF was 343±33 pg/ml, and the range was from 94 to 848 pg/ml. Accordingly, the mean p75ECD concentration in CSF was 2.22 times lower in AD patients compared to ND controls.

The presence of p75ECD was confirmed in the brain of AD subjects (FIG. 3 b, c, d) and in the brains of APPswe/PS1dE9 (AD) mice (FIG. 3 e, f, g) by Western blot. The p75ECD level in the brain (parietal cortex) was significantly reduced in human AD patients compared to the age and gender-matched non-demented controls (ND, n=12; P<0.05, FIG. 3c). The mean±s.e.m relative intensity of p75ECD concentration in AD patients, normalised to non-demented controls was 22±3%, meaning that the intensity of p75ECD in AD was decreased by more than 4 times compared to non-demented controls.

In comparison, the full-length (FL) p75 (p75FL) was significantly increased in human AD patients compared to the ND controls (P<0.01, n=12; FIG. 3c). The mean±s.e.m relative intensity of p75FL concentration in AD patients, normalised to non-demented controls as 315±20%, meaning that the intensity of p75FL in AD was increased by more than 3 times compared to non-demented controls.

Notably, the ratio of p75ECD to p75FL (p75ECD:p75FL) was significantly reduced in AD patients compared to ND controls (FIG. 3d). The mean±s.e.m of the ratio for AD patients (normalised to the mean±s.e.m non-demented controls) was 0.11±0.02%. Accordingly, the ratio was 9 times lower in AD patients compared to the non-demented controls. These results indicate that the processing of p75 to remove the ECD in AD was significantly reduced in AD patients compared to normal, non-demented controls.

TABLE 3

Raw data values of p75ECD in pg/ml obtained from Alzheimer's Disease (AD) Patients and Non-Demented (ND) controls in CSF

| | Raw data AD | Raw data ND |
|---|---|---|
| | 268.935 | 829.991 |
| | 93.605 | 865.057 |
| | 339.067 | 900.123 |
| | 181.27 | 917.656 |
| | 461.798 | 1005.321 |
| | 514.397 | 549.463 |
| | 304.001 | 865.057 |
| | 233.869 | 917.656 |
| | 374.133 | 865.057 |
| | 181.27 | 707.26 |
| | 286.468 | 777.392 |
| | 268.935 | 987.788 |
| | 479.331 | 1233.25 |
| | 584.529 | 829.991 |
| | 216.336 | 777.392 |
| | 426.732 | 812.458 |
| | 163.737 | 952.722 |
| | 198.803 | 637.128 |
| | 619.595 | 987.788 |
| | 233.869 | 865.057 |
| | 496.864 | 829.991 |
| | 374.133 | 1110.519 |
| | 268.935 | 549.463 |
| | 268.935 | 1092.986 |
| | 163.737 | 829.991 |
| | 304.001 | 724.793 |
| | 847.524 | 900.123 |
| | 198.803 | |
| | 584.529 | |
| mean | 342.6945 | 863.7583 |
| Std. Deviation | 172.25857 | 155.90695 |
| Std. Error Mean | 31.98761 | 30.00431 |

Figure 3:
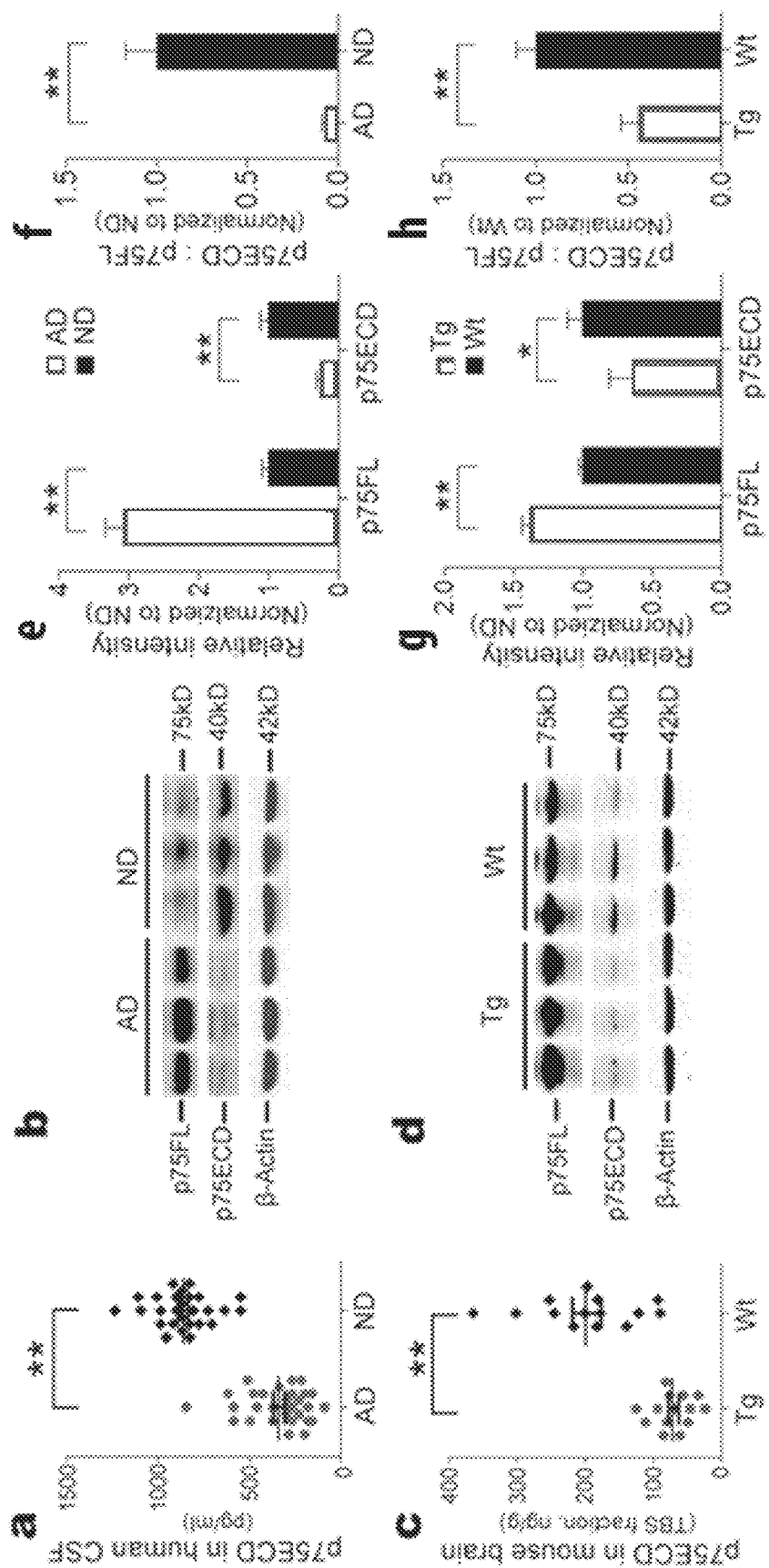
FIG. 3 provides (a) graphical representation of levels of p75ECD in human cerebrospinal fluid (CSF) in Alzheimer's disease (AD) patients and age-matched non-demented controls (ND) by ELISA (n=29 for AD, n=27 for ND, mean±s.e.m., Student's t-test, **$P<0.01$), (b) Western blot analysis of full length p75 (p75FL) and p75ECD in human AD and ND brain tissues, (c) quantitative analysis of p75FL and p75ECD Western blot band density shown in (b) and (d) ratio of p75ECD/p75FL Western blot band density shown in (b) (n=12 for AD, n=12 for ND, mean±s.e.m., Student's t-test, *$P<0.05$, $P<0.01$); (e) graphical representation of levels of p75ECD in Tris buffered saline (TBS) fraction of brain homogenates of 12-month old AD mice (Tg) and wild-type littermates (Wt) by ELISA (n=13 for Tg, n=14 for Wt, mean±s.e.m., Student's t-test, $P<0.01$), (f) Western blot analysis of full length p75 (p75FL) in brain tissues from 12-month old Tg and Wt mice, (g) quantitative analysis of p75FL and p75ECD Western blot band density shown in (f) and (h) ratio of p75ECD/p75FL Western blot band density shown in (f) (n=13 for Tg, n=14 for Wt, mean±s.e.m., Student's t-test, *P<0.05, **P<0.01)

The abnormal expression of p75ECD and p75FL was remarkably similar in the brains of 12-month old AD mice when compared with their Wt littermates (FIG. 3 e, f, g, h). Specifically, the mean±s.e.m p75ECD levels in the mouse brain by ELISA 75±5 ng/ml; whereas the p75ECD concentration in wt littermates was 201±10 ng/ml (FIG. 3e). Accordingly p75ECD was 2.7 times lower in AD mice than in the wt mice.

p75FL was expressed at significantly higher levels in the brains of AD mice compared to the wt litter mates (FIG. 3 f, g); and p75ECD was expressed at significantly lower levels in AD mice compared to wt littermates (FIG. 3 f, g). Specifically, the mean±s.e.m. relative intensity of p75ECD in AD mice compared to the wt littermates was 65±4% (FIG.

3g). Accordingly, the p75ECD concentration was approximately 0.35 times lower in AD mice compared to the wt controls.

The ratio of p75ECD to p75FL was significantly reduced in AD mice compared to wt equivalents (FIG. 3h). Specifically, the mean±s.e.m. p75ECD:p75FL ratio in AD mice normalised to wt mice was 48±4%, meaning that the ratio was 2.1 times lower in AD mice compared to the wt littermates (FIG. 3h).

In AD animals, brain p75ECD levels are negatively correlated with cognitive impairment, brain Aβ burden and inflammation (Table 3, 4 and 5).

TABLE 4

Correlation of brain p75ECD level with brain inflammation

| Variable | Coefficients | Std. Error | t value | P value | 95.0% Confidence Interval |
|---|---|---|---|---|---|
| Microgliosis | −0.005 | 0.001 | −3.623 | 0.002 | −0.008-0.002 |
| Astrocytosis | −0.012 | 0.005 | −2.560 | 0.020 | −0.023--0.002 |
| IL-6 level | −6.232 | 2.248 | −2.773 | 0.013 | −10.954--1.508 |
| TNF-α level | −0.177 | 0.055 | −3.220 | 0.005 | −0.293--0.061 |

TABLE 5

Correlation of brain p75ECD level with Aβ burden in brain

| Variable | Coefficients | Std. Error | t value | P value | 95.0% Confidence Interval |
|---|---|---|---|---|---|
| Aβ burden (ELISA) | −199.514 | 66.620 | −2.995 | 0.008 | −339.477--59.551 |
| Aβ burden (Congo red staining) | −0.001 | 0.000 | −2.522 | 0.021 | −0.001-0.000 |
| Aβ burden (6E10 IHC) | −0.004 | 0.001 | −3.562 | 0.002 | −0.007--0.002 |

TABLE 6

Correlation of brain p75ECD level with behavioural performance

| Variable | Coefficients | Std. Error | t value | P value | 95.0% Confidence Interval |
|---|---|---|---|---|---|
| Latency in MWM | −0.127 | 0.039 | −3.229 | 0.005 | −0.210--0.044 |
| Alteration in Y-maze | 0.159 | 0.040 | 4.002 | 0.001 | −0.076-0.243 |
| Rearing in open field | 0.064 | 0.016 | 4.078 | 0.001 | −0.031--0.096 |

MWM, Morris water maze

While not wanting to be bound by theory, these results indicate that the processing of p75 to remove the ECD was significantly reduced in AD compared to normal wildtype littermates.

Tumor necrosis factor alpha convertase enzyme (TACE) is reported to be the main enzyme cleaving the ECD of p75 (Weskamp, G. et al., 2004). As disclosed herein, it has been found that TACE activity was significantly reduced in the brain of AD mice (data not shown) and in CSF of AD patients (data not shown) compared to their ND or wt equivalents. TACE expression in AD mice was also reduced compared with the age-matched Wt controls (data not shown). In contrast to nerve growth factor (NGF) which increases TACE-dependent cleavage of p75 (Urra, S. et al., 2007; Kommaddi, R. P. et al., 2011), Aβ treatment of mouse cortical neurons significantly reduced TACE expression in a dose-dependent manner (data not shown). While not wanting to be bound by theory, these results indicate that the reduction in soluble p75ECD in AD is a down-stream toxic action of Ab.

Restoration of Brain p75ECD Levels of AD Mice by Delivery of the Recombinant Human ECD-Fc Gene Given that recombinant ECD-Fc can disrupt Aβ-p75 interaction and inhibit Aβ aggregation (Wang, Y. J. et al., 2011), and that p75ECD level was reduced in the AD brain as described above, and it was considered that the restoration of the p75ECD level in AD brains may protect neurons against the pathology of Aβ. An adeno-associated virus 8 (AAV8) was used to deliver a fusion gene of human p75ECD and human IgG Fc fragment (AAV-ECD-Fc) into the lateral ventricle of AD mice at three months of age (prior to the development of amyloid plaques in the brain) to examine whether ECD delivery can be used to prevent Aβ-related disease, and also at nine months of age (when amyloid plagues are well developed) to examine whether ECD delivery could be used as a treatment to reduce symptoms of Aβ-related disease. The dose of AAV used was equivalent to that used in human clinical trials of AAV. AAV expressing green fluorescent protein (GFP) gene was used as a control. Expression of the ECD-Fc transgene was detected at one week after delivery, and remained stable in neurons of neocortex, hippocampus and thalamus up to 12 months of age when animals were culled as detected with an anti-human Fc antibody which only detects the ECD-Fc expressed from the transgene but not endogenous p75ECD (data not shown).

Figure 4:
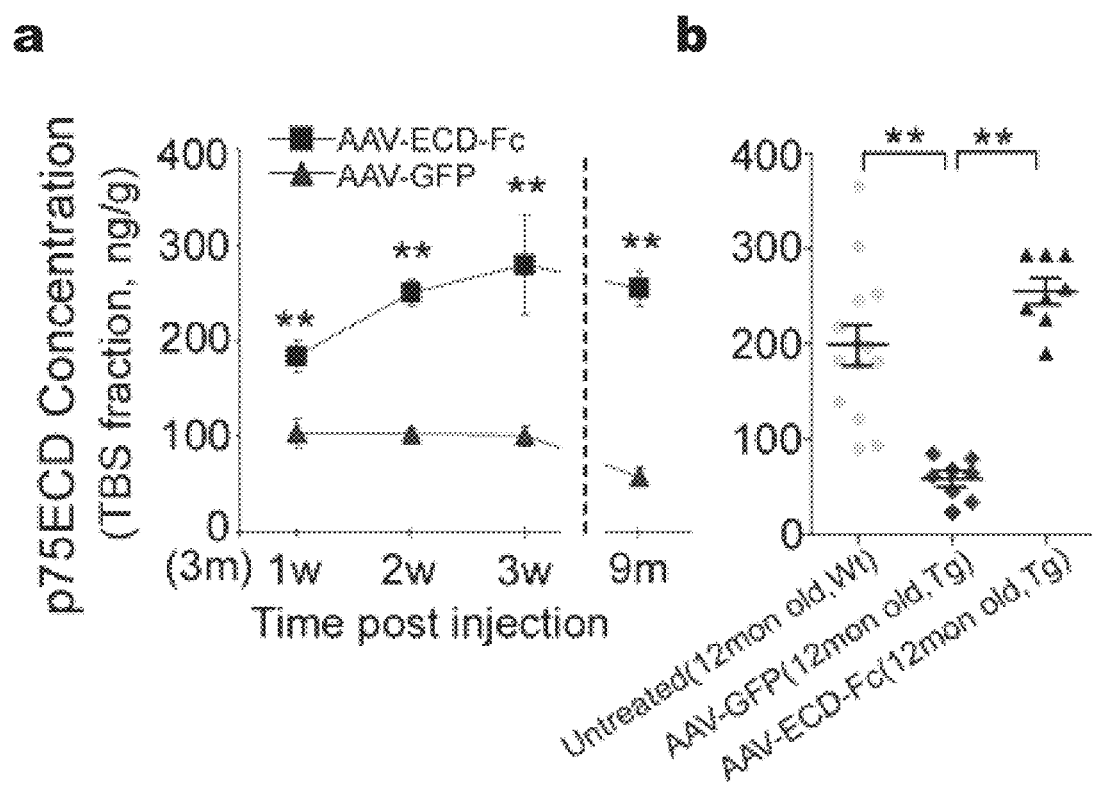
FIG. 4 provides graphical representation of (a) expression levels of ECD-FC after intraventricular injection of AAV-ECD-Fc or AAV-GFP in the left lateral ventricle of AD mice at 3 months of age as analysed by ELISA analysis for p75ECD in TBS fraction of AD mouse brain homogenates at 1 week (1 w), 2 weeks (2 w), 3 weeks (3 w), and 9 months (9 m) after injection, (n=5 per group for 1 w, 2 w and 3 w, and n=8 for 9 m group), and (b) expression levels of p75ECD in TBS fraction of 12 month old AD mice following intraventricular injection of AAV-ECD-Fc or AAV-GFP in the left lateral ventricle at 3 months of age compared to 12-month old Wt mice as analysed by ELISA analysis for p75ECD (n=8 for 12-month old Tg mice injected with AAV-GFP or AAV-ECD-Fc, and n=13 for wt mice); mean±s.e.m., ANOVA, Tukey test, **P<0.01)

When AAV-ECD-Fc was injected in left lateral ventricle at 3 months of age, immunofluorescence of p75ECD-Fc was detected with anti-human IgG Fc antibody (α-IgG-Fc) in brain sections of animal injected with AAV, with expression of ECD-Fc in cortex, hippocampus and thalamus (data not shown). p75ECD-Fc was expressed in neurons but not in microglia or astrocytes (data not shown). ELISA analysis of p75ECD in TBS fraction of AD mouse brain homogenates at 1 week (1 w), 2 weeks (2 w), 3 weeks (3 w), and 9 months (9 m) after injection of AAV-ECD-Fc showed stable expression (FIG. 4a). At 12 months of age, the levels of ECD-Fc in the brain of AD mice after the transfection were similar to ECD levels of age-matched Wt mice (FIG. 4b).

Restoration of Brain p75ECD Level Prevents Cognitive Decline in AD Mice

Figure 5:
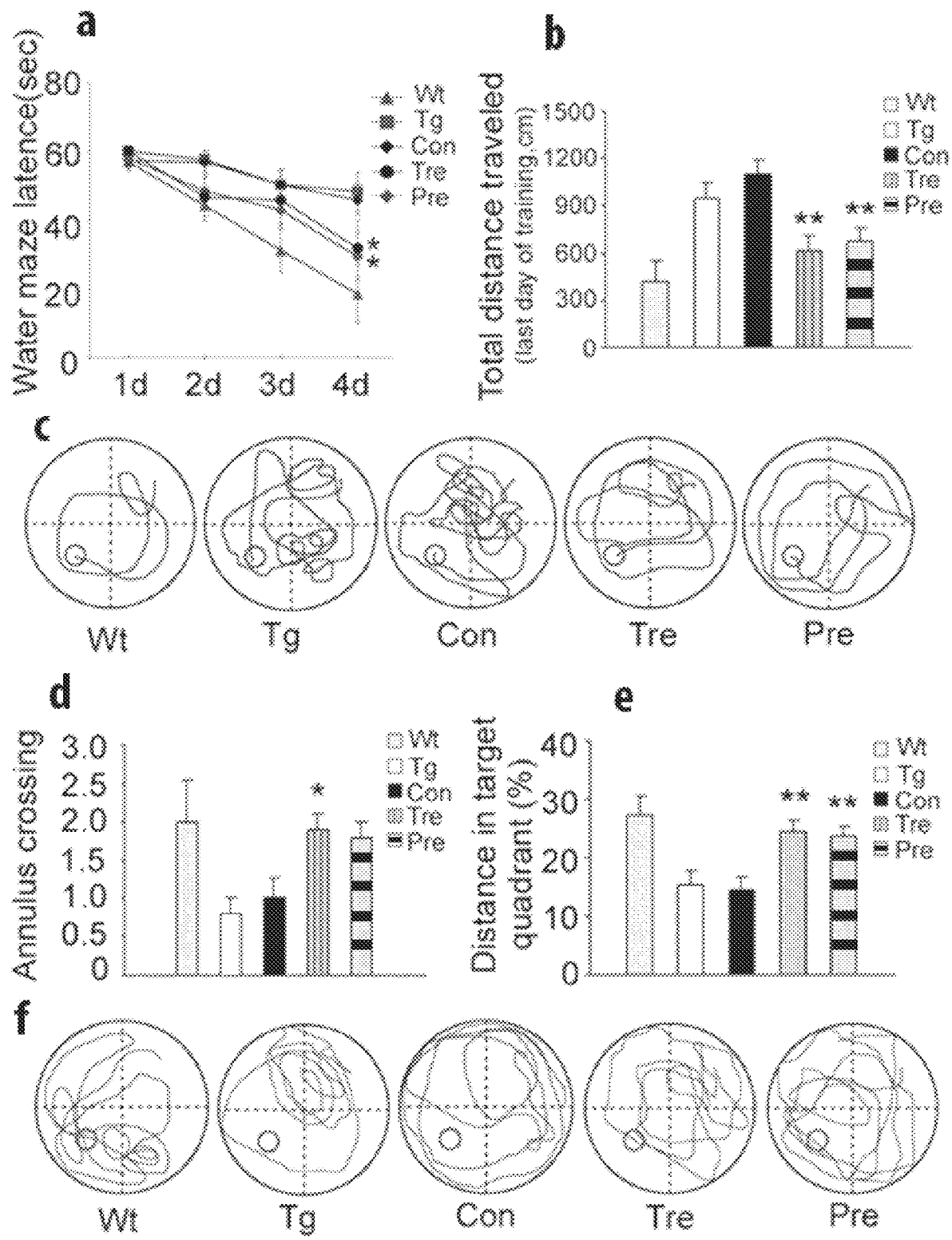
FIG. 5 provides graphical representation of behavioural analysis of twelve-month-old mice including Wt littermates (Wt, n=16), untreated AD mice (Tg, n=15), AD mice injected at 3 months or 9 months with AAV-GFP as control (Con, n=14), AD mice injected with AAV-ECD-Fc at 9 months of age for Treatment (Tre, n=12) and AD mice injected with AAV-ECD-Fc at 3 months of age for Prevention (Pre, n=11) in a Morris water-maze analysis showing (a) latency (seconds) during platform trials, (b) distance traveled (centimetres) on the last day of training, (mean±s.e.m., ANOVA, Tukey's test, *P<0.05, **P<0.01, vs Con), and (c) representative locomotor activity tracing graphs; probe trial at day 5 showing (d) numbers of crossing over the annulus of the platform which was removed and (e) distance traveled in the quadrant where the platform was located (mean±s.e.m.; one-way ANOVA, Tukey's test, *P<0.05, **P<0.01 vs Con), and (f) representative locomotor activity tracing graphs; Y-maze analysis showing (g) alternation of arms and (h) numbers of entries in the spontaneous alternation test, and (i) number and (j) time of entries in the novel arm test (mean±s.e.m.; one-way ANOVA, Tukey's test, *P<0.05, **P<0.01, vs Con; #P<0.05, ##P<0.01, vs Wt); open-field analysis showing (k) number of rearings, (l) distance traveled (centimetres), and (m) representative locomotor activity training graphs (mean±s.e.m.; one-way ANOVA, Tukey's test, *P<0.05, vs Con)
Figure 5:
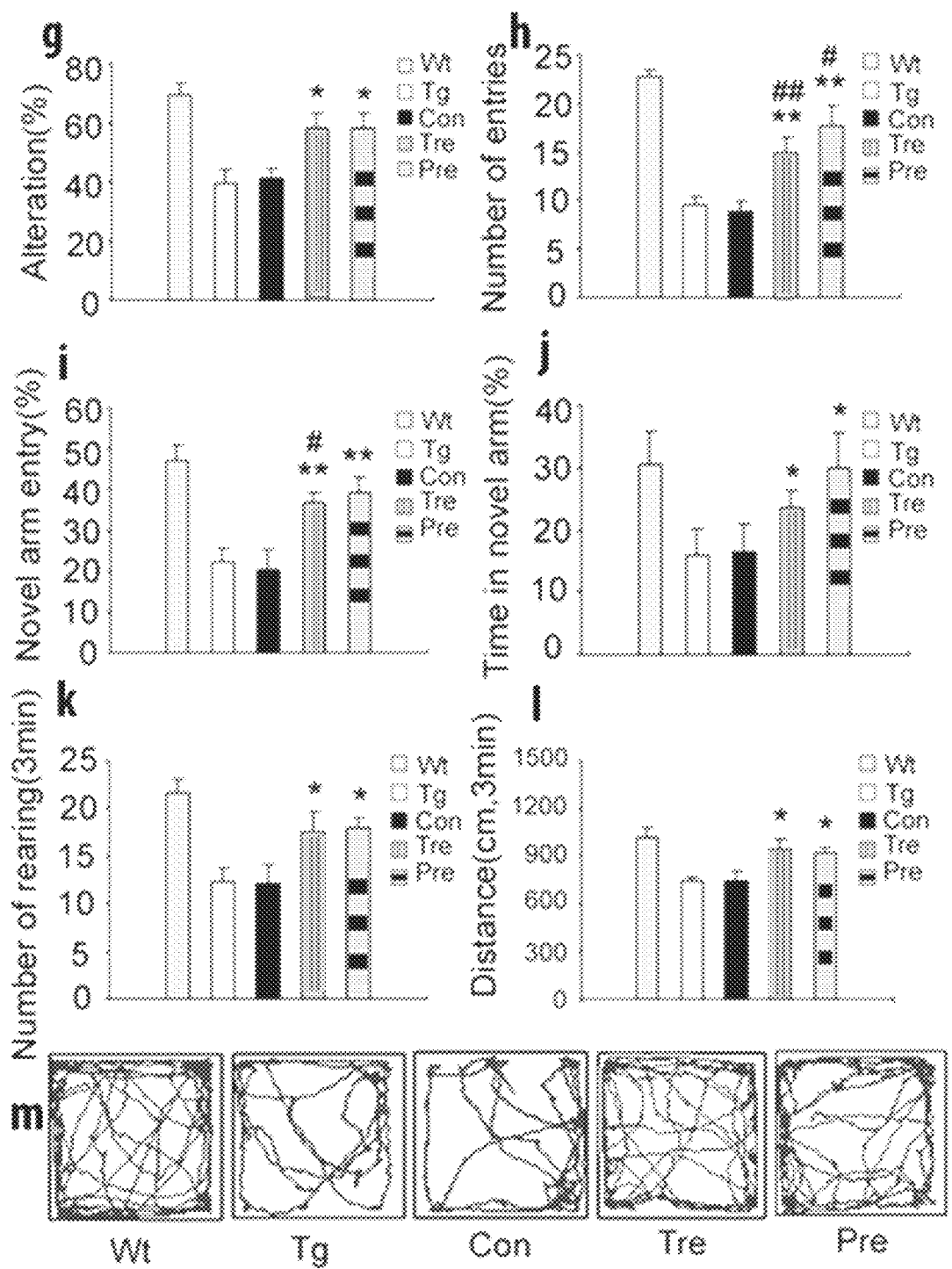

AD mice treated with AAV-ECD-Fc at 3 or 9 months of age (as prevention (Pre) or treatment (Tre), respectively) performed better in the Morris Water Maze test compared to AAV-GFP-treated control mice (con). This was reflected by a significant reduction in the escape latency time and travel distance taken to escape onto the platform with progressive platform learning trials (FIG. 5a, b, c), and greater numbers of platform area crossing and more time spent in the platform quadrants in the probe trials without the platform (FIG. 5d, e, f). These data indicate that p75ECD-Fc, whether administered at 3 months as a prevention, or at 9 months as a treatment, significantly improved spatial learning and memory in AD mice. The mice in both prevention and treatment groups also performed better in Y-maze and Open-field tests than the GFP-administered control, as reflected by more entries into the novel arm and higher spontaneous alternation in the Y-maze test (FIG. 5g, h, i, j). This indicates that the working memory of the p75ECD-Fc administered mice was better than that of the GFP-administered control mice. There were also a higher number of rearings, a longer distance traveled and reduced time spent in the central zone in the ECD-Fc-administered mice than the GFP-administered control mice in the open-field test (FIG. 5 k, l), being comparable to Wt mice. The data indicate that the p75ECD-Fc administered mice have better general locomotor activity than the GFP-administered control AD mice. Accordingly, ECD administration provides protective effects in AD mice on memory and behaviour.

Figure 6:
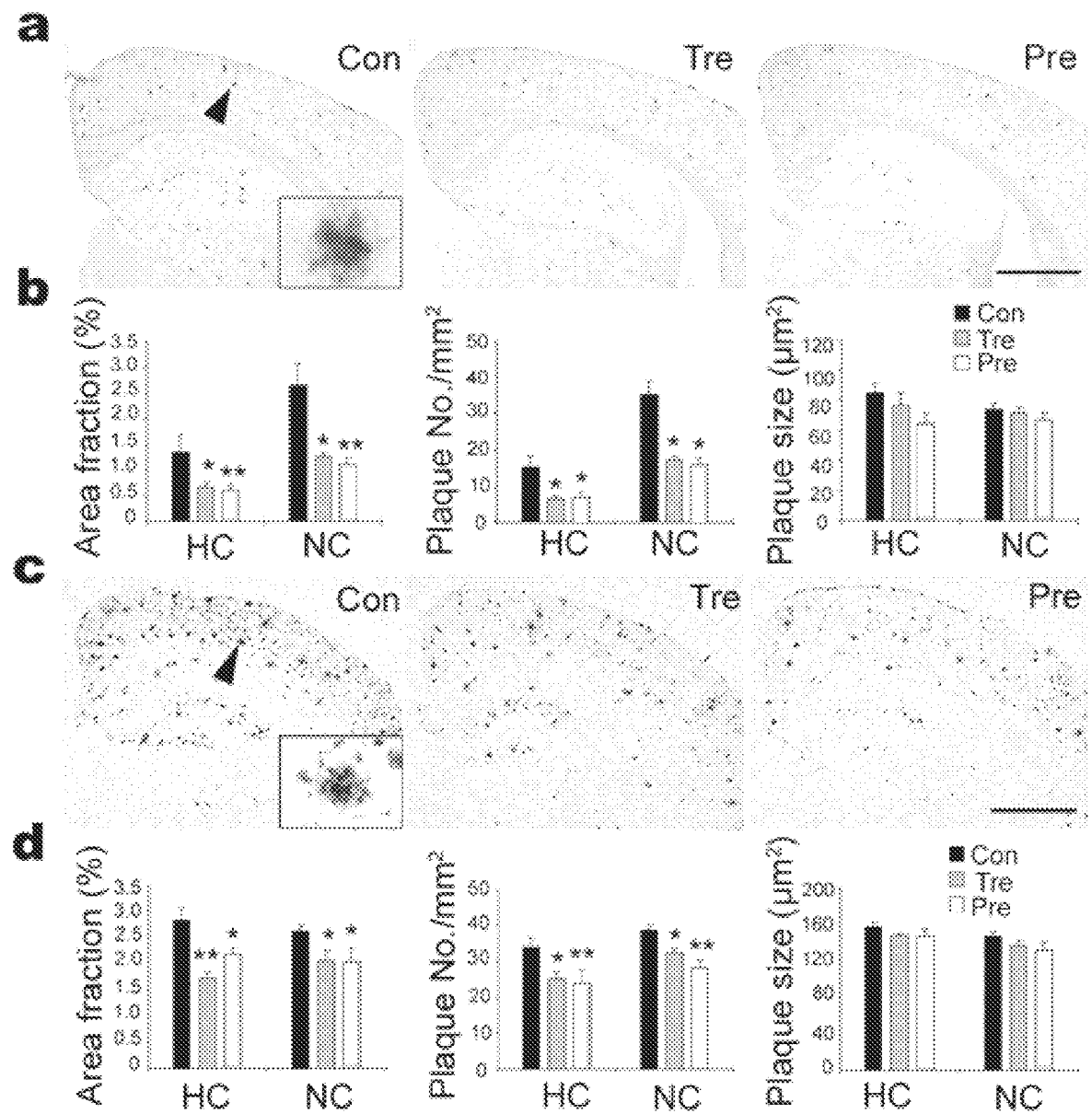
FIG. 6 provides analysis of the fractional area, density and size of Aβ plaques in the hippocampus (HC) and neocortex (NC) in five equally spaced sections across the whole brain per animal quantified by ImageJ software in 12-month old AD mice injected at 3 or 9 months old with AAV-GFP as controls (Con, n=7-9), AD mice injected with AAV-ECD-Fc at 9 months of age for Treatment (Tre, n=8-9) and AD mice injected with AAV-ECD-Fc at 3 months of age for Prevention (Pre), showing (a) Aβ plaque deposition visualized using Congo red staining (scale bar=1 mm); comparison of (b, left panel) fractional area, (b, middle panel) plaque density and (b, right panel) size of Congo red stained plaques among groups; (c) Aβ plaques stained with antibody 6E10 immunohistochemistry (scale bar=1 mm); comparison of (d, left panel) fractional area, (d, middle panel) plaque density and (d, right panel) size of 6E10 stained plaques among groups (for (a)-(d), n=11 for Con, n=9 for Tre, n=8 for Pre, mean±s.e.m., one-way ANOVA, Tukey's test, *P<0.05, **P<0.01, vs Con); ELISA analysis of Aβ40, A042 and total Aβ in TBS, SDS and formic acid (FA) fractions of (e-i) brain homogenates and (e-ii) serum (for brain homogenates, n=11 for Con, n=9 for Tre, n=8 for Pre; for serum, n=14 for Con, n=12 for Tre, n=11 for Pre, mean±s.e.m., one-way ANOVA, Tukey's test, *P<0.05, P<0.01, vs Con); (f) micrographs showing cerebral amyloid angiopathy (CAA) visualized by Congo red straining (scale bar=1 mm), (g) comparison of CAA profiles among the Con, Tre and Pre groups (n=8, mean±s.e.m., one-way ANOVA, Tukey's test, P<0.01, vs Con); (h) comparison of number of cerebral microbleeds among the Con, Tre and Pre groups (n=8, mean±s.e.m., one-way ANOVA, Tukey's test, **P<0.01, vs Con); (i) micrographs showing colocalization of Aβ plaque and ECD-Fc in APP/PS1 transgenic AD mice (scale bar: 200 µm (black), 40 µm (white), * indicates colocalization of ECD-Fc with amyloid-β plaques, # indicates ECD-Fc expression in neurons.
Figure 6:
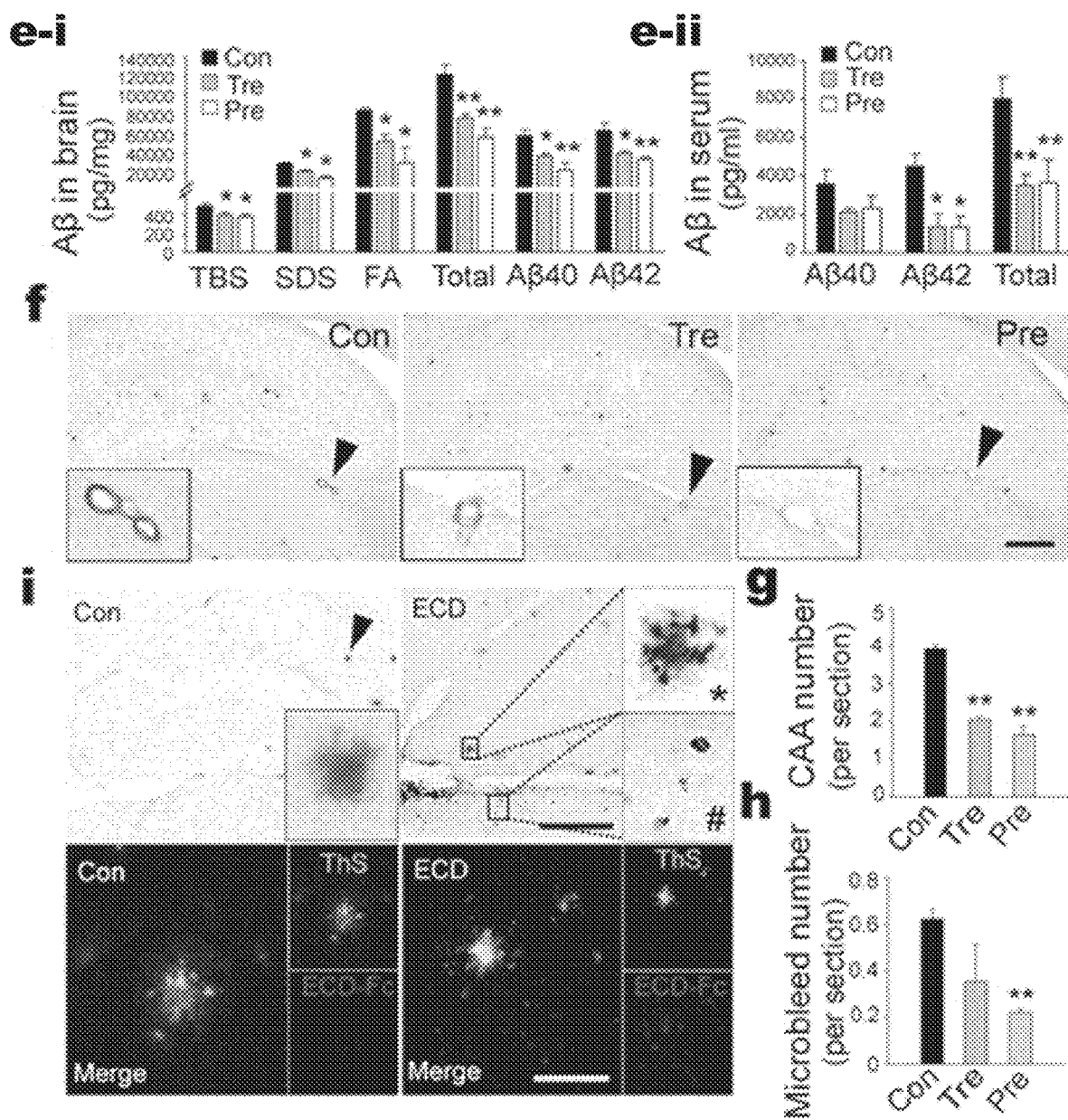

Restoration of Brain p75ECD Level Reduces Aβ Levels in the Brain and Blood of AD Mice In AD mice administered with p75ECD-Fc at 3 months of age (prevention) or 9 months of age (treatment), the fraction areas and density of Congo red staining plaques in hippocampus (HC) and neocortex (NC) were reduced by approximately 50% compared with the GFP administered controls (FIG. 6 a, b, c, d), meaning that amyloid plaques are reduced by 50% after p75ECD treatment. The amyloid plaque load in the hippocampus and cortex identified by immunohistochemistry with antibody 6E10 was also reduced in AD mice administered p75ECD-Fc in the prevention and treatment groups, compared with the controls (FIG. 6 e).

Congo red staining was also used to examine mice for Cerebral Amyloid Angiopathy (CAA). As shown in FIG. 6 (f), p75ECD-Fc reduces the severity of CAA as demonstrated by Congo red staining in blood vessels. As is apparent from FIG. 6 (g), p75ECD-Fc reduces the number of CAA lesions by approximately 50% with the mean±s.e.m. number of CAA lesions identified for the control group being 3.95±0.12; while the prevention group had 2.05±0.13; and the treatment group had 1.75±0.20. The mean±s.e.m. microhaemorrhage number was also reduced by approximately 50% in both prevention and treatment groups (FIG. 6 h), a the control group had a mean±s.e.m microhaemorrahge number of 0.63±0.03; while the prevention group had a mean±s.e.m microhaemorrahge number of 0.375±0.13; and the treatment group had a mean±s.e.m microhaemorrahge number of 0.22±0.02. This indicates that administration of p75ECD-Fc as a treatment or a prevention in subjects with an increased Aβ load reduces CAA pathology.

Interestingly, p75ECD-Fc was localized around and within Congo red or Thioflavine S positive plaques as detected by immunohistochemistry (FIG. 6 i), suggesting that expressed human p75ECD-Fc binds and interacts with Aβ plaques. Consistent with the histological results, ELISA tests also showed a significant reduction in total Aβ and Aβ40 or Aβ42 levels in TBS, SDS and formic acid fractions of brain homogenates and serum in both the prevention and treatment groups (FIG. 6 i, j). This result accordingly indicates that p75ECD-Fc administration reduces Aβ levels in brain and blood.

Restoration of Brain p75ECD Level Reduces Amyloidogenic Processing of APP by Inhibiting BACE1 Expression in AD Mice In sporadic AD, Aβ upregulates β-site APP-cleaving enzyme (BACE1) expression and drives the vicious cycle leading to AD pathogenesis. However, it is not known which receptor mediates the Aβ-JNK-BACE1 vicious cycle. While not wanting to be bound by theory, it has been suggested that p75 may upregulate Aβ production (Wang Y. J. et al., 2011), forming a positive feedback. It was investigated whether the disruption of the Aβ-p75 interaction with p75ECD-Fc can affect APP processing and Aβ production. The p75ECD-Fc treatment significantly reduced BACE1 expression and activity, the β-cleavage product (CTFβ) of APP and Aβ production in both prevention and treatment groups (data not shown). However, the Aβ degrading enzymes neprilysin (NEP) and insulin degrading enzyme (IDE), and Aβ blood-brain barrier (BBB)-transporting molecules low density lipoprotein receptor-related protein (LRP) and receptor for advanced glycation end products (RAGE) did not change (data not shown).

To determine the mechanism by which p75ECD suppresses amyloidogenesis in vivo, the expression of BACE1, APP and APP fragments in primary neurons was examined. They realised that BACE1 expression and the sAPPβ level in the cultured primary neurons was dose-dependently increased in response to Aβ42β or Aβ25-35 (data not shown). This increase was abolished by the presence of recombinant ECD-Fc or in p75 KO neurons (data not shown). Aβ also dose-dependently increased the expression of APP in AD/p75+/+ neurons ($p<0.05$) but not in AD/p75−/− neurons (data not shown). The level of full length APP was increased ($p<0.001$) but the level of sAPPβ decreased ($p<0.001$) in AD/p75−/− neurons in the absence or presence of Aβ in comparison with that in ADp75+/+ neurons (data not shown), suggesting that p75 is required for amyloidogenic APP processing promoted by Aβ. Accordingly, the results indicate that p75 is a key receptor mediating Aβ-induced BACE1 upregulation and plays a critical role in the Aβ-BACE1 vicious cycle driving the pathogenesis of AD. As disclosed herein, it was realised that p75ECD-Fc treatment could break this vicious cycle as the data indicates that p75ECD-Fc reduces Aβ production via inhibition of BACE1 expression.

Figure 7:
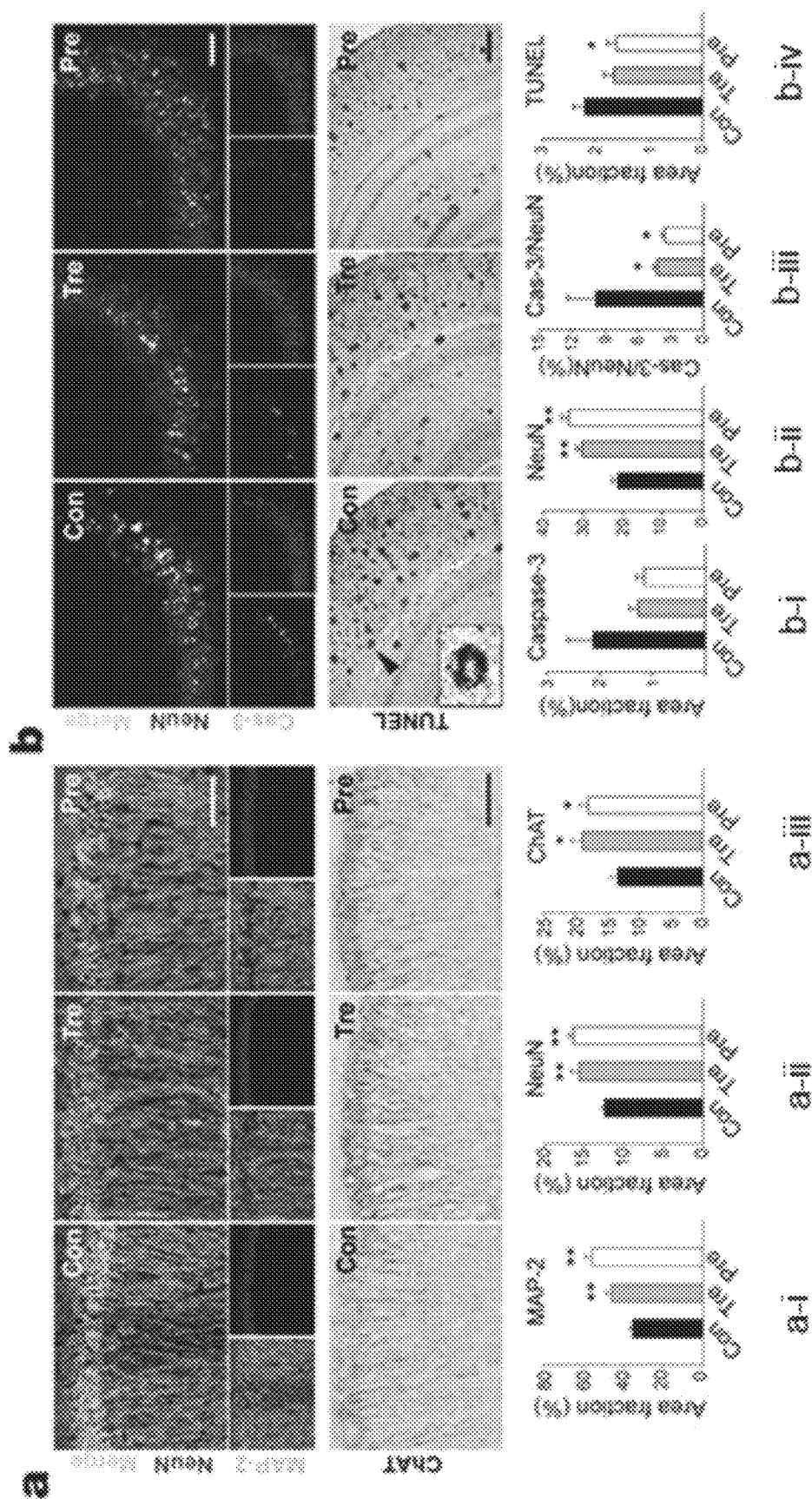
FIG. 7 provides results from AD mice injected 9 months with AAV-GFP as controls (Con), AD mice injected with AAV-ECD-Fc at 9 months of age for Treatment (Tre) and AD mice injected with AAV-ECD-Fc at 3 months of age for Prevention (Pre) with (a) micrographs showing the overall preserved structure of neurons and dendrites using (top panel) anti-MAP-2 and anti-NeuN immunofluorescence, or (bottom panel) anti-choline acetyltransferase (ChAT) immunohistochemistry (n=11 for Con, n=9 for Tre, n=8 for Pre, mean±s.e.m., one-way ANOVA, Tukey's test, *P<0.05, **P<0.01, vs Con, Scale bar=100 µm), which was quantified (a-i, a-ii, a-iii, a-iv); (b) micrographs showing neuronal apoptosis using activated caspase-3 (cas-3) by immunofluorescence (scale bar=50 µm, top panel) or using TUNEL staining (scale bar=250 µm, bottom panel), which was quantified (b-i, b-ii, b-iii, b-iv) (n=11 for Con, n=9 for Tre, n=8 for Pre, mean±s.e.m., one-way ANOVA, Tukey's test, *P<0.05, **P<0.01, vs Con); (c-i) micrographs showing Golgi stain analysis of spine with a representative Golgi stained image of a CA1 pyramidal neuron (left) and different dendritic spines (right, bar=10 µm, n=3, mean±s.e.m., one-way ANOVA, Tukey's test, *P<0.05, vs Con), (c-ii) quantitative analysis of spines per µm; (c-iii) Western blot of synapse-associated proteins including SNAP25 and PSD95, and (c-iv) quantitative analysis of data in (c-iii), (c-v) Western blot of Synapsin I (Syn I), VAMP1, synaptophysin (SYP), and (c-vi) respective quantification of data in (g) (n=8, mean±s.e.m., one-way ANOVA, Tukey's test, *P<0.05, **P<0.01, vs Con); (d-i) micrographs of Tau phosphorylation using pSer396 immunostaining (Scale bar=200 µm), (d-ii) Western blot analysis (n=8, mean±s.e.m., one-way ANOVA, Tukey's test, *P<0.05, P<0.01, vs Con) of Tau phosphorylation using anti-pS396, pT231, pS262 and pS199 antibodies, the result of which are (d-iii) quantified, and the relative intensity of binding of each of (d-iv) anti-ps396, (d-v) anti-pT231, (d-vi) antipS262, (d-viii) anti-ps199 in each of the groups; (e) micrographs of analysis of neurite outgrowth of cultured primary mouse cortical neurons stained with anti-MAP-2 and DAPI immunofluorescence (n=35, mean±s.e.m., ANOVA, Tukey's test, P<0.01, vs Aβ42 scr., #P<0.05, vs Aβ42, Scale bar=50 µm), which is (f) quantified; (g) a flow diagram depicting roles of p75FL and p75ECD in AD pathogenesis.
Figure 7:
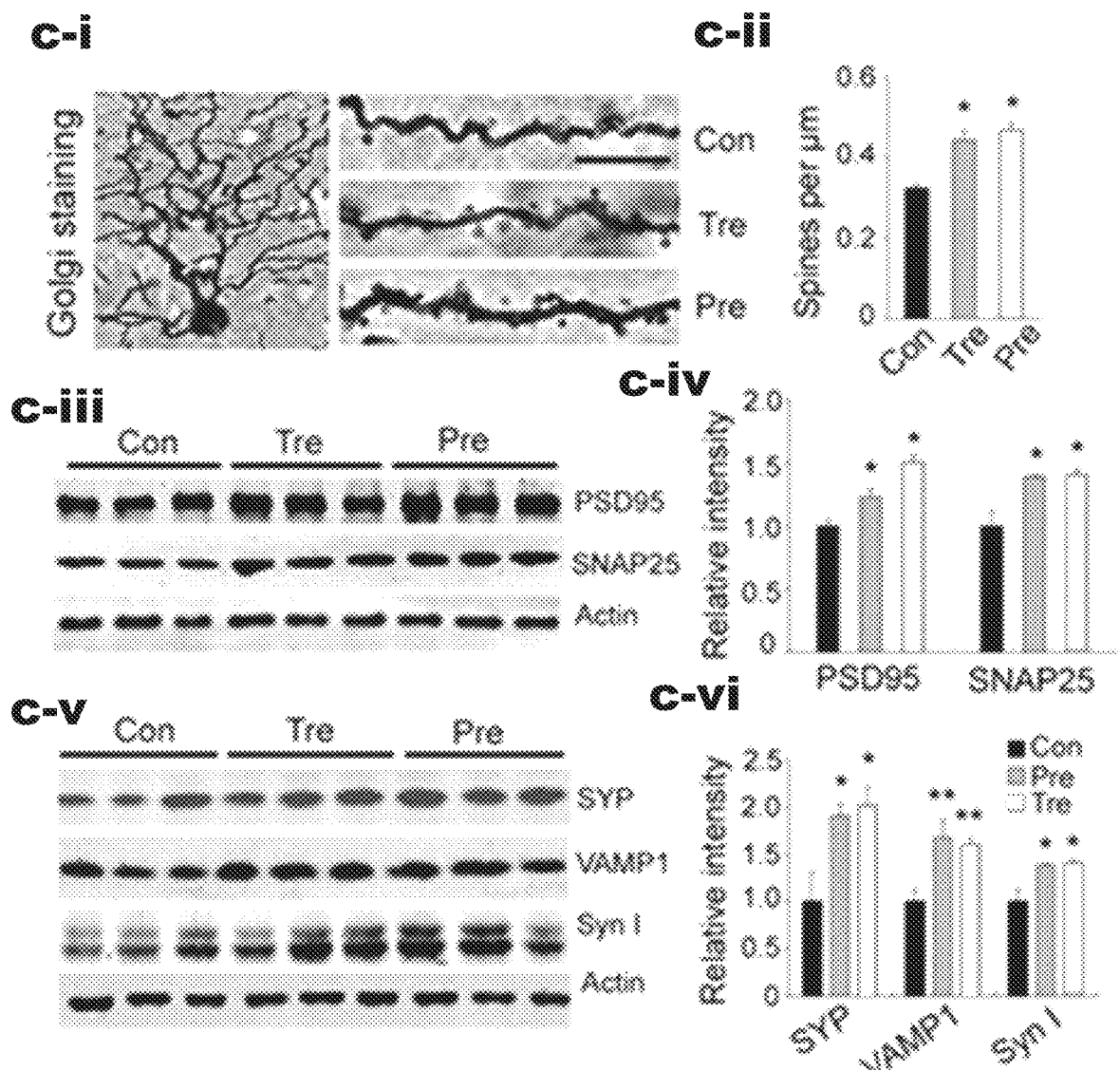
Figure 7:
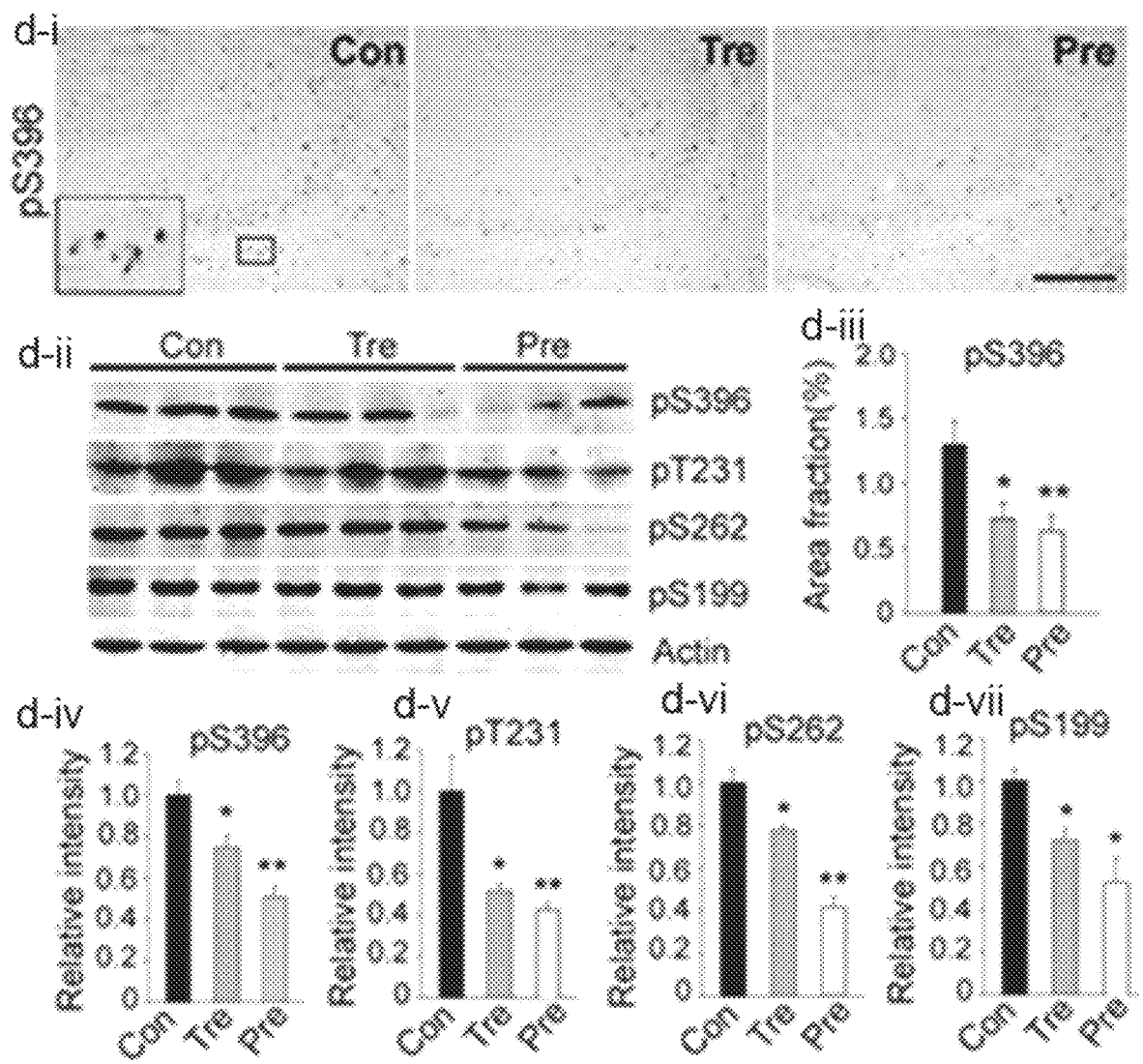
Figure 7:
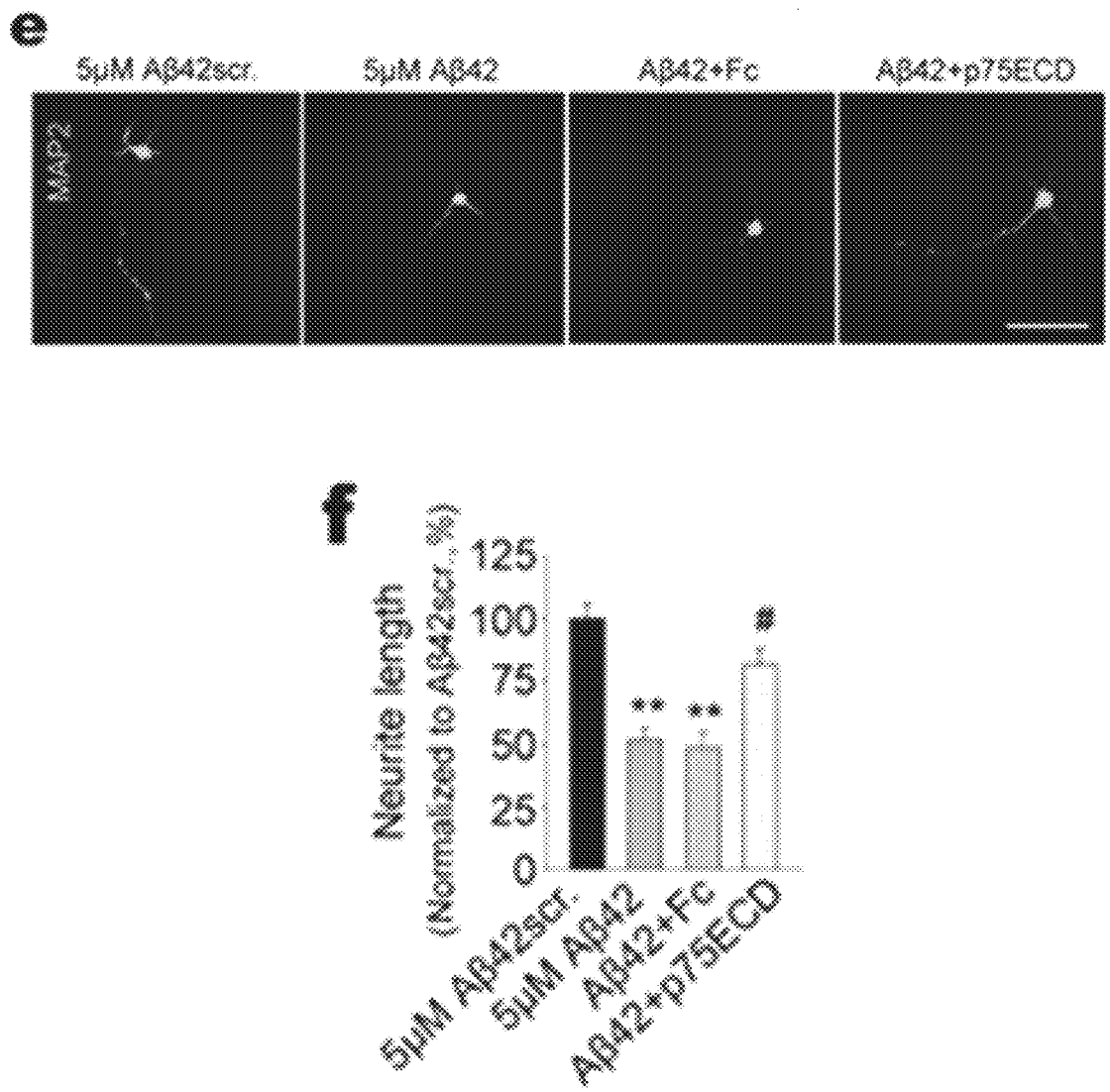

Restoration of Brain p75ECD Level Attenuates Neurite Degeneration, Neuronal Death and Tau Phosphorylation in AD Mice Compared with GFP administered control AD mice, the fractional areas stained for NeuN (neurons) and MAP-2 dendrites and ChAT positive axons in the hippocampus were increased in both prevention and treatment groups (FIG. 7a), indicating the p75ECD-Fc treatment can preserve neuronal structure in the hippocampus of AD mice. The number of dendritic spines detected by the Golgi staining method in the hippocampus was significantly increased in both prevention and treatment groups (FIG. 7b), indicating that that p75ECD-Fc can protect cholinergic neurons and hippocampal neurons from Aβ-induced toxicity. The levels of synaptic proteins, including the major synaptic vesicle protein p38 synaptophysin, the vesicle-associated membrane protein (VAMP) 1, synaptosomal-associated protein 25 (SNAP25), postsynaptic density protein 95 (PSD95) and synapsin I (Syn I) were increased significantly in the brain of both prevention and treatment groups (FIG. 7b), indicating that p75ECD-Fc can protect neuronal synapses and connectivity of the central nervous system from the toxicity of Aβ. The fractional area of activated caspase-3 and TUNEL staining, which identified apoptotic cells, in the hippocampus in the prevention and treatment groups was significantly lower than that of the control (FIG. 7c). Accordingly, consistent with the in vivo data, the recombinant p75ECD-Fc protected primary cortical neurons from the neurite collapse triggered by Aβ (FIG. 7e).

The fractional area of Tau-phospho-Ser396 positive neurons in the hippocampus of both prevention and treatment groups was lower than that of the control (FIG. 7d, top and middle panels). The levels of Tau-phosphorylation at multiple sites including serine 396, 262, 199 and threonine 231 were consistently and significantly diminished in the brain of both prevention and treatment groups (FIG. 7d, middle and bottom panels), indicating that the administration of p75ECD-Fc reduces tau phosphorylation associated with tauopathy. While not wanting to be bound by theory, it is considered that the effect of p75ECD on Tau phosphorylation is via blocking Aβ that activates upstream GSK3β

Figure 8:
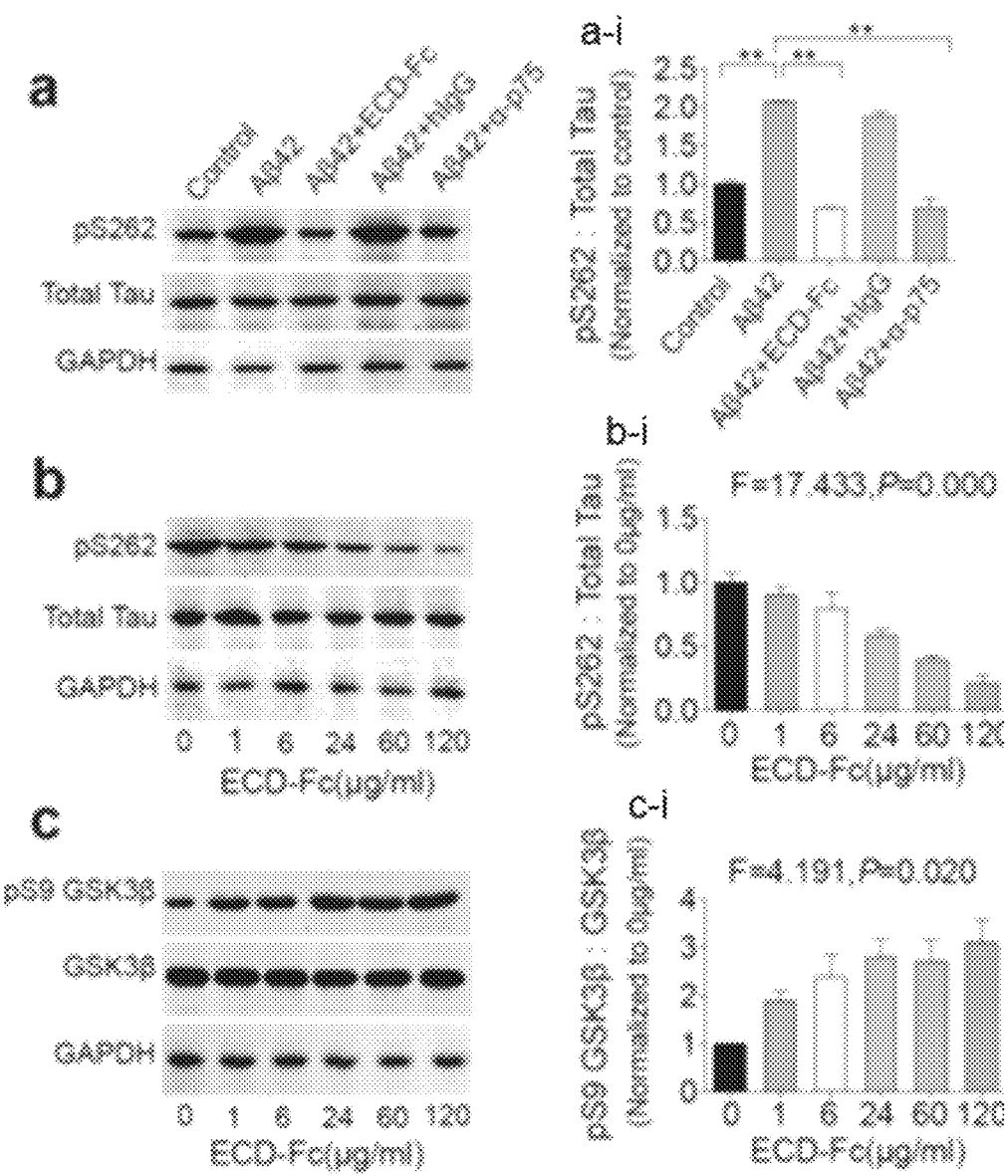
FIG. 8 provides (a) (left) Western blot results and from SHSY5Y cells following differentiation in retinoic acid for three days and then treatment with 5 uM Aβ and indicated reagents, and (right) quantification of the pTau262:total Tau ratio, showing that ECD-Fc reversed Tau hyperphosphorylation induced by Aβ (n=3, mean±s.e.m., one-way ANOVA, Tukey's test, **P<0.01, vs Control; ##P<0.01, vs Aβ42), (b) (left) Western blot analysis and (right) quantification of concentration-dependent inhibitory effect of recombinant p75ECD-Fc on Tau hyperphosphorylation induced by Aβ (n=5, mean±s.e.m.), and (c) (left) Western blot analysis and showing that GSK3β phosphorylation at serine 9 and (right) quantification of the ratio of GSK3β phosphorylation at Ser9/GSK3β with increasing concentrations of p75ECD-Fc (n=5, mean±s.e.m.)

(Chakravarthy, B. et al., 2012). Indeed, it was found that both recombinant p75ECD-Fc peptide and p75 receptor neutralizing antibodies could block the increased phosphorylation of Ser262 of Tau in response to Aβ in the human SH-SY5Y cell line (FIG. 8a). Moreover, recombinant p75ECD-Fc dose-dependently suppressed the phosphorylation of S262 and increased p-Ser9-GSK3β triggered by Aβ42 (FIGS. 8b, c). These data indicate that p75ECD-Fc reduces Aβ induced Tau hyperphosphorylation via inhibition of GSK3β activity in SH-SY5Y cells. Accordingly, the elevation of p75ECD levels can protect against Aβ-induced axon and neurite degeneration, neuronal death and Tau hyperphosphorylation associated with Tauopathy.

Restoration of Brain p75ECD Level Attenuates Microgliosis, Astrocytosis and Inflammation in the Brain of AD Mice Brain inflammation including microgliosis and astrocytosis is a secondary hallmark of AD. The fractional area of CD45 (microgliosis) and GFAP (astrocytosis) staining in the cortex and hippocampus in both prevention and treatment groups were significantly reduced compares to the control group (data not shown). The levels of inflammatory cytokines TNF-α, IFN-γ, IL-1β and IL-6 in the TBS fraction and serum in both prevention and treatment groups were also lower than those in the control group (data not shown). The better performance in learning and memory tasks and reduced neuroinflammation are a probable outcome secondary to the reduction in amyloid burden, Tau-phosphorylation and neurodegeneration after the ECD-Fc treatment.

Delivery of the ECD-Fc Gene by AAV8 is Well Tolerated

During the period of the animal study, no animal death occurred and no obvious abnormal behaviour was observed. The gene delivery did not significantly influence animal body weight or liver enzymes (data not shown). No discernible pathological morphology was observed in major organs including brain, muscle, heart, liver, lung, kidney and intestine (data not shown). These data suggest that long-term expression of the ECD-Fc fusion gene in the brain is well tolerated by AD mice, indicating the safety of AAV-ECD-Fc treatment.

Discussion

As disclosed herein, it has been realised that soluble p75ECD (ie following shedding from p75) is a potentially useful therapeutic and biomarker for AD. Soluble p75ECD is physiologically distributed in both central and peripheral nervous systems and is developmentally regulated by ageing. The p75ECD level was realised to be significantly reduced in the brain of AD subjects and mice, potentially due to the Aβ-induced reduction in the expression and activity of TACE. Additionally, it was found that p75ECD protects neurons from Aβ-induced neurotoxicity and suppresses BACE1 expression and Tau-phosphorylation. Moreover, the restoration of p75ECD levels by administration of p75ECD-Fc in the brain of AD mice protects the brain from neurodegeneration.

The function of soluble p75ECD after shedding has previously been unknown. As disclosed herein, it has been realised that p75ECD is a neurotrophic molecule protecting neurons against neurodegeneration in the AD brain. Surprisingly the p75ECD level is significantly reduced in AD, suggesting the cleavage process in AD is impaired by Aβ. As TACE is a physiological sheddase regulating the production of p75ECD (Westkamp et al. 2004), the reduced level of p75ECD in the AD brain is a likely result of the impaired p75 cleavage due to the reduction in the expression and activity of TACE triggered by Aβ.

As disclosed herein, it has been found that p75 mediates Aβ-induced BACE1 upregulation, as both p75ECD-Fc and p75 knockout mice can block Aβ-induced BACE1 upregulation and inhibit amyloidogenic APP processing. The data described herein suggest that p75FL is a central player driving the Aβ-BACE cycle. The reduction of p75ECD levels in the AD brain may contribute to the over-production of Aβ, exacerbating the vicious cycle; and the restoration of the p75ECD level in vivo can suppress BACE1 expression and the associated amyloidogenic pathway. p75ECD can break the Aβ-BACE1 vicious cycle which contributes to Aβ over-production in AD.

p75ECD protects neurons at multiple levels of the Aβ cascade leading to the pathogenesis of AD, including the suppression of Aβ aggregation and deposition (Wang, Y. J. et al., 2011), Aβ over-production and neurotoxicity, and Aβ-induced Tau-phosphorylations. The treatment with p75ECD-Fc and p75 antibodies in vitro and in vivo can block the Tau phosphorylation, suggesting Aβ-induced Tau-phosphorylation is likely mediated by p75. Taken together, p75ECD is a novel neurotrophic molecule, which is reduced in AD, which protects the brain from Aβ toxicity. Restoration of the p75ECD level in AD brain could be a desirable therapeutic approach for AD.

Example 2 Specificity of Effect of p75ECD

To investigate the specificity of p75ECD-Fc on amyloid burden, additional experiments were performed by injection of recombinant p75ECD-Fc or one of two control proteins (human IgG or recombinant human fibroblast growth factor receptor 4 ECD fused with human IgG Fc (FGFR4-Fc)) in the hippocampus of 8-month old AD mice. A single injection of the recombinant p75ECD-Fc, but not human IgG or FGFR4-Fc, also significantly reduced the area fraction of amyloid plaques on the injected site one week after injection (data not shown). To investigate potential mechanism of how p75ECD-Fc affects the amyloid burden in the brain, the effect of p75ECD-Fc on Aβ fibrillation and disaggregation with ThT tests and transmission electronic microscopy (TEM) visualization was examined. The data showed that p75ECD-Fc, but not the control proteins human IgG or FGFR4-Fc, suppressed the Aβ fluorescence in fibrillation and the fluorescence of preformed Aβ fibres (data not shown). TEM visualization established that p75ECD-Fc, but not human IgG or FGFR4-Fc, prevented the formation of Aβ fibres and disaggregated the preformed Aβ fibres (data not shown). The data indicates that the effect of p75ECD-Fc on amyloid burden in vivo is a specific event not, and is not due to non-specific protein-Aβ interaction.

Additionally, consistent with the in vivo data, recombinant p75ECD-Fc, but not human IgG and recombinant FGFR4-Fc, suppressed the cell death of SH-SY5Y cells and protected cortical neurons from the neurite collapse triggered by Aβ in vitro (data not shown).

These experiments indicate that the effect of p75ECD-Fc on amyloid burden is specifically due to the effect of p75ECD.

Example 3 Intramuscular Delivery of p75ECD-Fc in AD Mice Reduces AD Pathologies and Improves Cognitive Function AD mice (APP/PS1 transgenic mice) or wild type were intramuscularly injected with AAV-ECD-Fc as follows: Female APP/PS1 transgenic mice were injected with $2 \times 10^9$ vector genomes of AAV-ECD-Fc or AAV-GFP in 5 μl intramuscularly at the tibial muscle at 3 months of age. At 12 months of age, all mice were sacrificed and brains were sampled. The control group received AAV-GFP, but were otherwise treated identically. Following treatment, the mice were tested using the Morris Water maze test. In some experiments, mice were intraperitoneally injected with recombinant p75ECD-Fc peptide once at 50 µg/50 µl per mouse. Other experiments were performed as described above.

Intramuscular Delivery of p75ECD Improves Cognitive Decline in AD Mice

Figure 9:
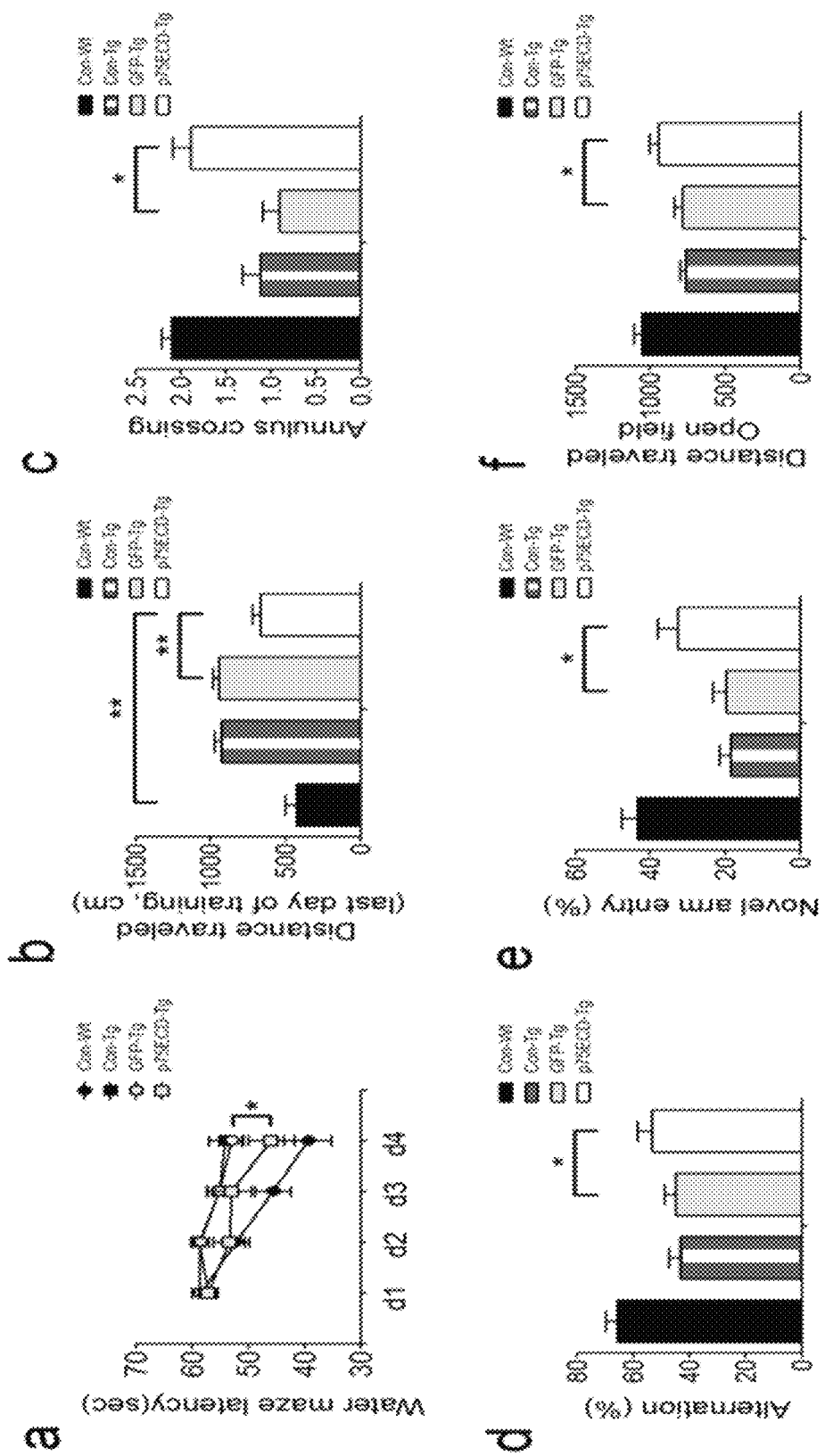
FIG. 9 provides results from peripheral injection of p75ECD or GFP in AD (APP/PS1 transgenic) or wild type mice, with (a) showing escape latency (seconds) during platform trials in Morris water maze, (b) showing the distance traveled to escape onto the platform during platform trials, (c) showing the number of annulus crossing in probe test, (d) showing the percentage of alternation and (e) novel arm entry in Y-maze test, and (f) showing the distance traveled in open filed test; wherein p75ECD-Tg denotes AAV-p75ECD-Fc intramuscularly injected APP/PS1 mice, GFP-Tg denotes AAV-GFP intramuscularly injected APP/PS1 mice, Con-Tg denotes APP/PS1 mice that received no injection, and Con-Wt demotes wild type mice that received no injection; animal number=8 for each group, mean±s.e.m., Tukey test; *P<0.05, **P<0.01, vs GFP.

Compared with AAV-GFP-treated mice, the mice treated with AAV-ECD-Fc performed better in the Morris Water Maze test. This was reflected by a significant reduction in the escape latency time and the distance traveled to escape onto the platform with progressive platform learning trials, greater number of platform area crossings (FIGS. 9a, b,c). The data indicates that the AAV-ECD-Fc treatment significantly improves spatial learning and memory in AD mice. Moreover, the AAV-ECD-Fc treated mice also performed better in Y-maze and open-field tests than the AAV-GFP-treated controls. This was reflected by more entries into the novel arm and higher spontaneous alternation in the Y-maze test (FIGS. 9 d and e). It indicates that the working memory of the AAV-ECD-Fc treated mice was better than that of the control mice. In the open-field test, a longer travelling distance was observed in the AAV-ECD-Fc treated mice, compared with AAV-GFP-treated controls (FIG. 9 f), indicating that the ECD-Fc-treated mice have better exploration activity than the control AD mice. However, the swimming speed is not significantly different among groups, indicating that the mice have comparable locomotion activity. This data therefore shows that intramuscular p75ECD delivery improve cognitive decline in AD mice.

Figure 10:
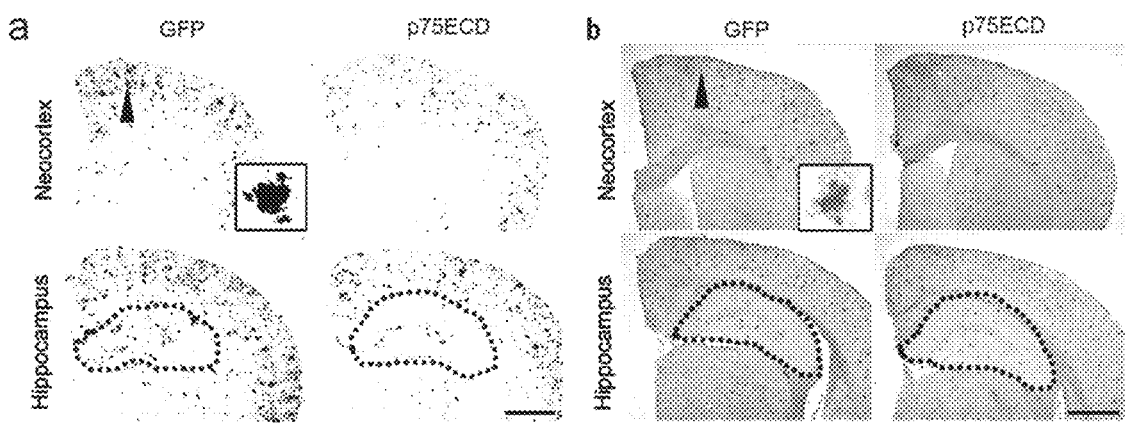
FIG. 10 provides results from peripheral injection of p75ECD or GFP in AD mice, with (a) showing Aβ deposition stained using 6E10 immunochemistry, scale bar=1 mm, (b) quantification of area fractions of Aβ deposition as stained by 6E10 immunochemistry, (c) Aβ deposition stained using Congo red staining, Scale bar=1 mm, (d) quantification of area fractions of Aβ deposition as stained by Congo red staining, (e) ELISA quantification of Aβ levels in TBS, SDS fractions, FA extracts and serum, where NC indicates neocortex and HC indicates hippocampus, (f) serum Aβ40 and Aβ42 levels were significantly increased 24 hours after peritoneal injection of p75ECD peptide (50 μg/50 μl i.p.), pre-bleed indicates before blood sampling, animal number=8, mean±s.e.m., T test; *P<0.05, **P<0.01.
Figure 10:
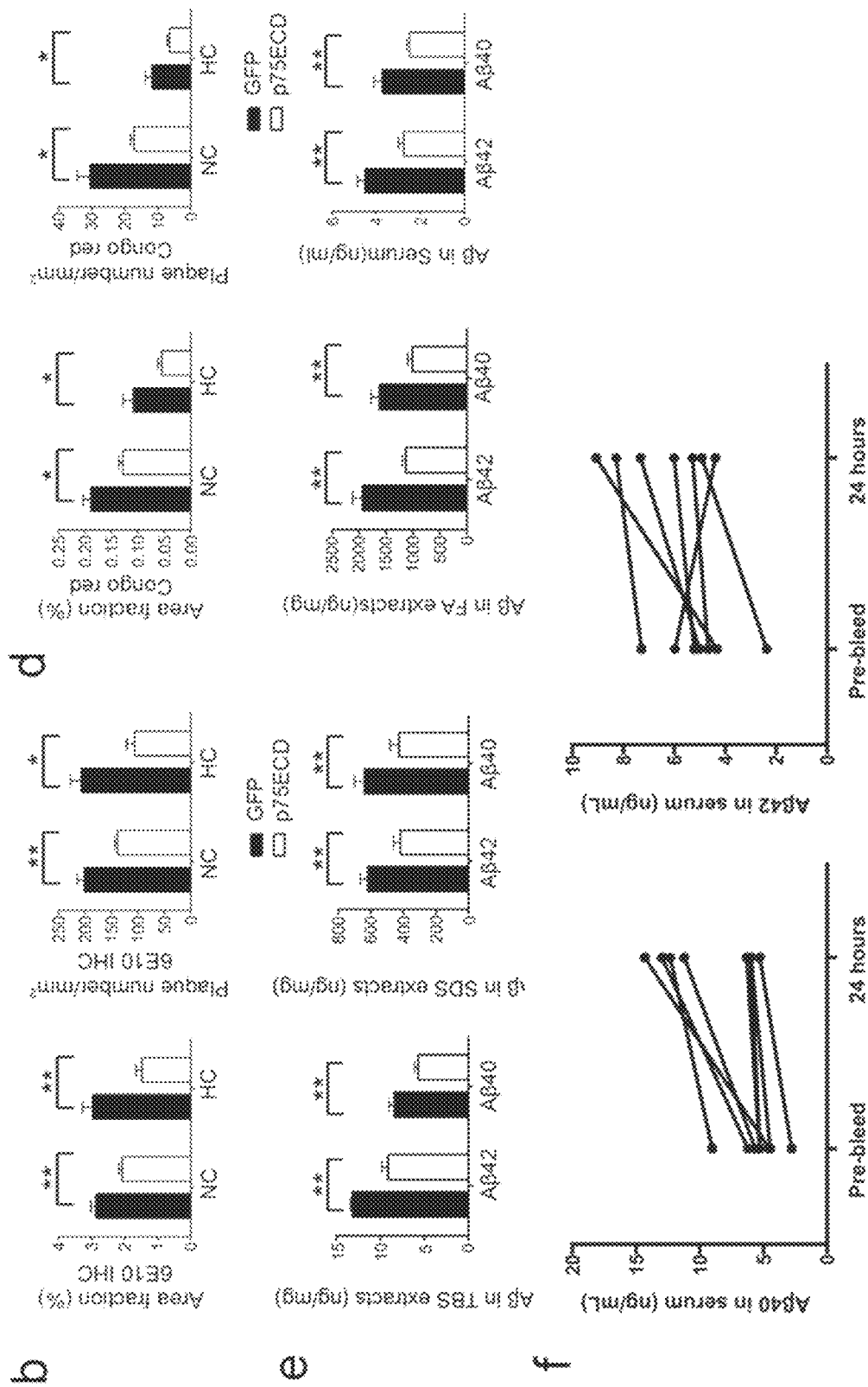

Intramuscular Delivery of p75ECD Reduces Aβ Burden in the Brain and Blood of AD Mice The amyloid plaque loads in the hippocampus and neocortex, identified by Congo red staining or immunohistochemistry, were reduced in AAV-ECD-Fc treated AD mice compared to the AAV-GFP treated controls (FIGS. 10 a to d). Consistent with the histological results, ELISA assay tests also showed a significant reduction in Aβ40 and Aβ42 in Tris-buffered saline, SDS and formic acid fractions of brain homogenates and serum in AAV-ECD-Fc treated AD mice (FIG. 10e). However, in an acute test in AD transgenic mice to which p75ECD-Fc was injected introperitoneally, serum Aβ40 and Aβ42 levels were significantly increased at 24 hours after peritoneal injection of p75ECD peptide once at 50 ug/50 ul each mouse (FIG. 10f), indicating that p75ECD could promote Aβ efflux from the brain into the periphery.

Figure 11:
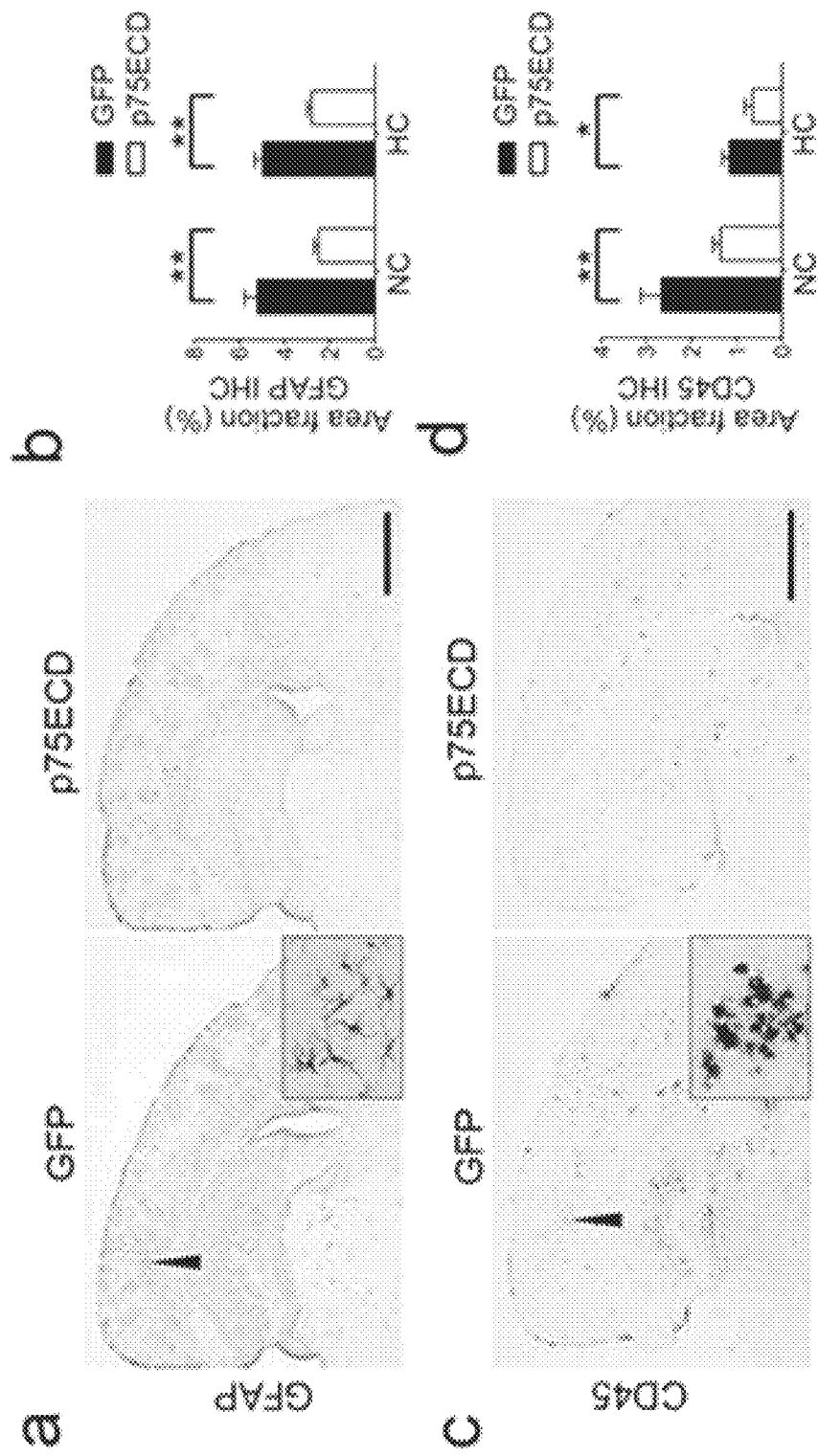
FIG. 11 provides results from peripheral injection of p75ECD or GFP in AD mice, with (a) showing astrocytes in the neocortex of AD mice stained with immunohistochemistry using anti-GFAP antibody, (b) quantification of the positive area fractions of GFAP staining, scale bar=1 mm, (c) microglia in the neocortex of AD mice were stained with immunohistochemistry using anti-CD45 antibody, (d) quantification of the positive area fractions of CD45 staining, where NC indicates neocortex and HC indicates hippocampus, animal number=8, mean±s.e.m., T test, *P<0.05, **P<0.01.

Intramuscular Delivery of p75ECD-Fc Attenuates Microgliosis, Astrocytosis and Inflammation in the Brain of AD Mice Brain inflammation including microgliosis and astrocytosis are the secondary hallmarks of AD pathology subsequent to Aβ. The fraction area of CD45 (microgliosis) and GFAP (astrocytosis) staining in the neocortex and hippocampus were significantly reduced in AAV-ECD-Fc treated AD mice compared to the AAV-GFP treated AD mice (FIG. 11), as reflected by reduced fractions of GFAP and CD45 positive staining areas. Accordingly, improved performance in learning and memory tasks and reduced neuroinflammation are likely outcomes of ECD-Fc treatment, in addition to the reduction in amyloid burden.

Figure 12:
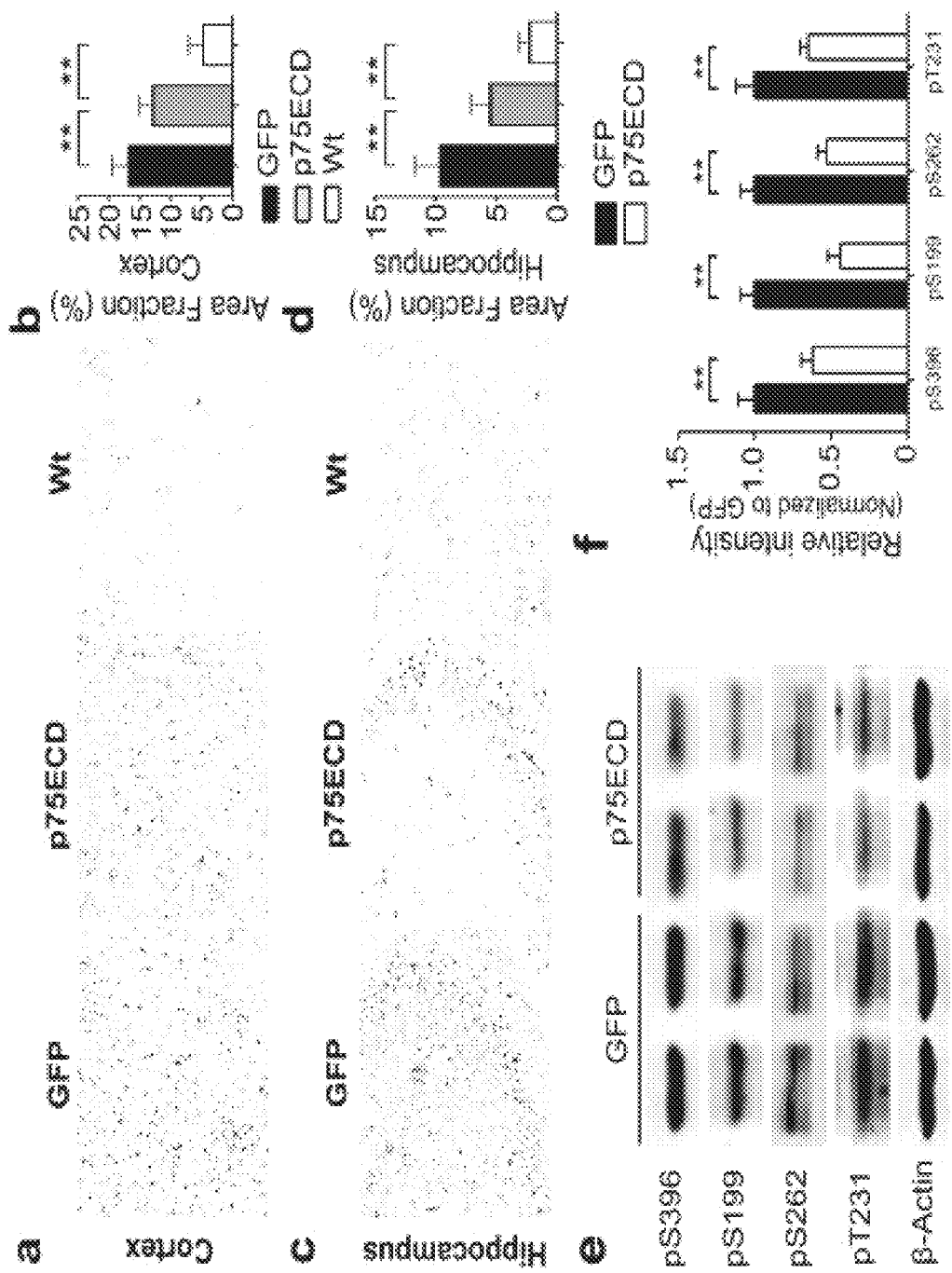
FIG. 12 provides results from peripheral injection of p75ECD or GFP in AD mice, with (a) showing immunohistological staining of pS396 in the cortex, bar=100 μm, (b) quantification of pS396 positive area fraction in the cortex, (c) immunohistological staining of pS396 in the hippocampus, bar=100 μm, (d) quantification of pS396 positive area fraction in the hippocampus, the relative intensity was normalized to Wt in (a) and (c), (e) western blot analysis of pS396, pS199, pS262 and pT231, (f) quantification of relative intensity of the bands of pS396, pS199, pS262 and PT231, animal number=8, mean±s.e.m., T test. **P<0.01.

Example 4 Intramuscular Delivery of p75ECD-Fc Attenuates Tau Hyperphosphorylation in AD Mice To assess Tau pathology, phosphorylation of the Tau protein at pS396, pT231, pS199 and pS262 were examined in AAV-ECD-Fc treated AD mice compared to the AAV-GFP treated controls, as described above. Phosphorylation at these sites was investigated using the anti-pS396, pT231, pS262 and pS199 antibodies described above. These phosphorylation sites were chosen in the present study as they are common sites of Tau hyperphosphorylation in AD mice. The fraction area of Tau-phospho-Ser396 positive neurons in the cortex and hippocampus was significantly lower in the p75ECD treatment groups than that in the GFP group (FIGS. 12 a, b, c and d). The levels of Tau phosphorylation at multiple sites including serine 396, 262, 199 and threonine 231 were consistently and significantly diminished in the brain of treated group (FIGS. 12 e and f). These findings indicate that p75ECD protects against Tau hyperphosphorylation.

Example 5 Treatment of Tauopathy Mice with p75ECD-Fc

Aggregates of hyperphosphorylated tau are prominent in brains of patients with Alzheimer's disease or frontotemporal dementia (FTD). They have been reproduced in animal models following the identification of tau mutations in familial cases of FTD. This includes our previously generated transgenic model, pR5, which expresses FTD (P301L) mutant microtubule associated protein tau (MAPT) in neurons (Deters et al., 2008). The mice are characterized by tau aggregation including tangle (NFT) formation, memory impairment and mitochondrial dysfunction. In this experiment, pR5 mice at 3 months old were randomly divided to two different groups. During the first week of treatment, 10 mg/kg of p75ECD-Fc or 5 mg/kg of Fc recombinant proteins were administrated to mice twice/week via ip injection to provide a sufficient amount of the proteins in the mice plasma. The mice then received 5 mg/kg recombinant p75ECD-Fc or 2.5 mg/kg recombinant Fc proteins twice/week in 150-200 µl volume PBS via ip injection for the remaining period of a total treatment time of 3 months.

Effect of p75ECD-Fc on Cognitive Functions of Mice with Taupathy

Figure 13:
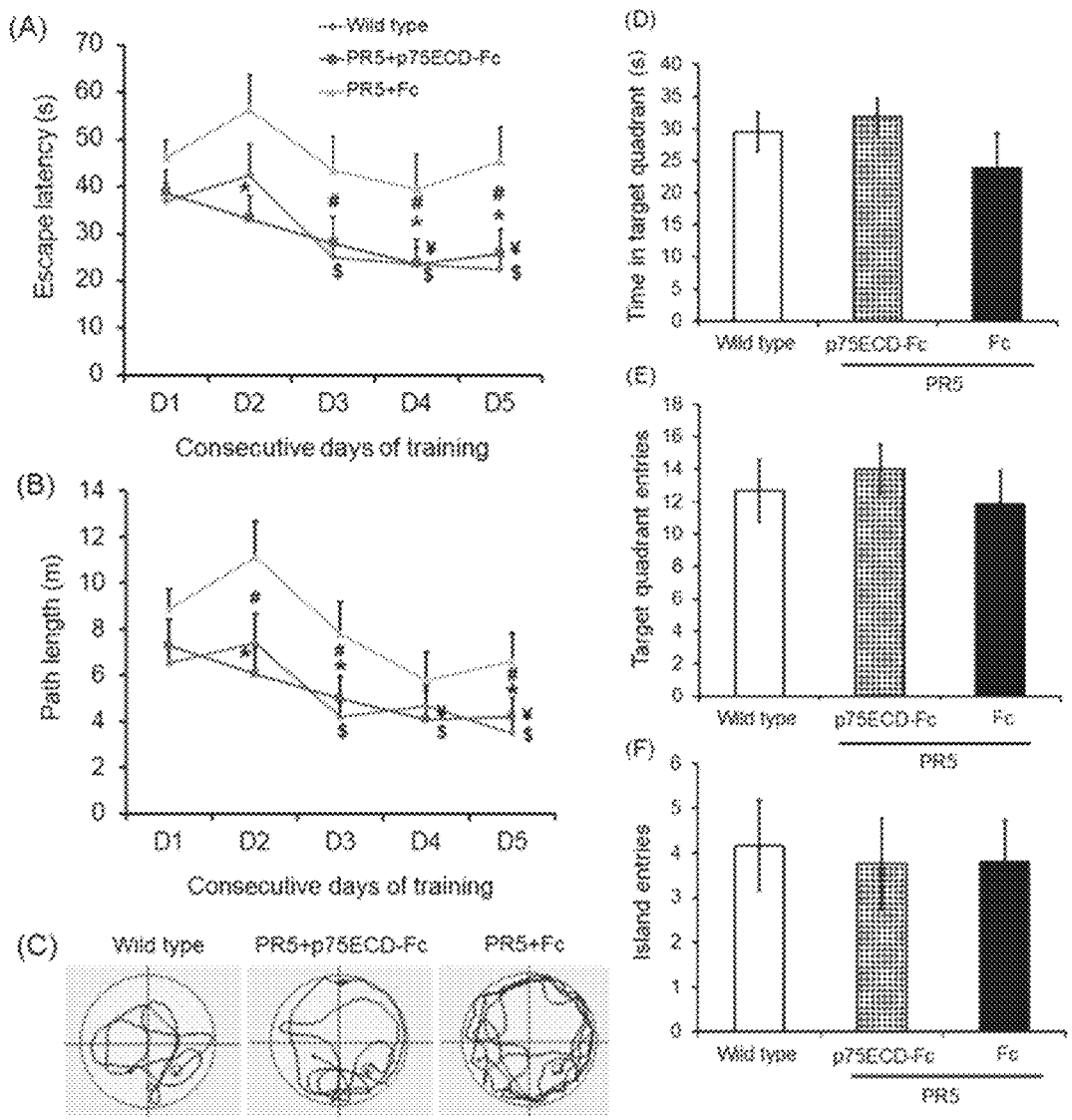
FIG. 13 provides results of pR5 (Tau) mice during a Morris Water Maze (MWM) test following treatment with recombinant p75ECD-Fc or Fc with (a) showing escape latency time (b,c) travel distance to find platform within progressive platform learning trials, (d) time spent and (e) the number of entries in the platform quadrants (f) the numbers of crossings of the hidden platform site in the probe trials between groups (*p<0.05 for p75ECD-Fc vs Fc group, #p<0.05 for wild type vs Fc group; $p<0.05 in wild type during learning process compared with 1st day of learning; ¥p<0.05 in p75ECD-Fc during learning process compared with 1st day of learning *p<0.05) (n=6 per group, mean±SEM, ANOVA, Tukey's post hoc test)
Figure 14:
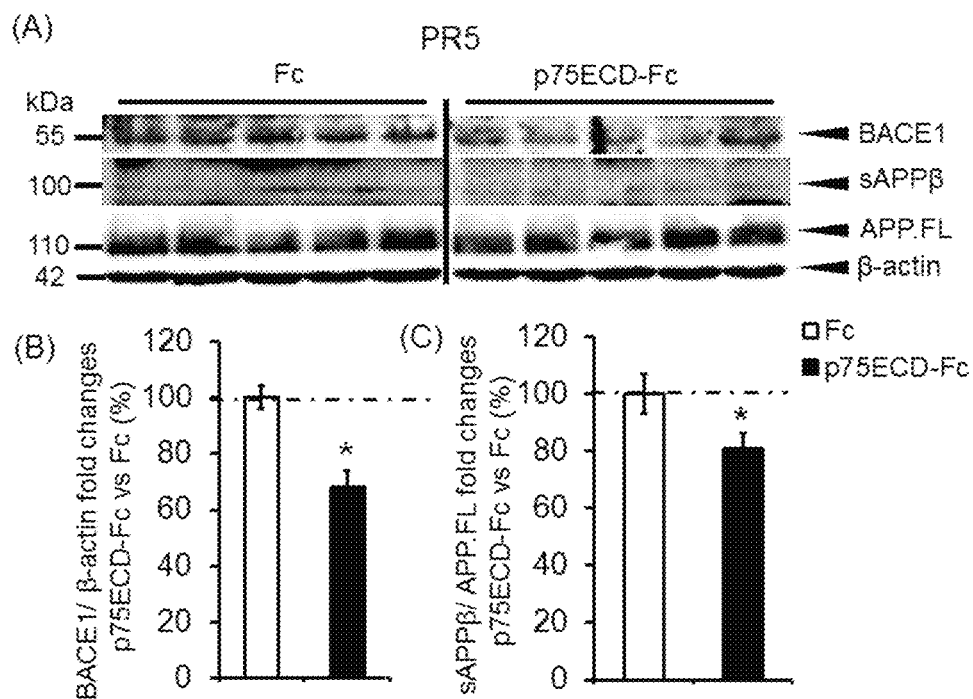
FIG. 14 provides results of A) Western blots showing the expression of BACE1, sAPPβ, full length of APP (APP.FL) and β-actin in p75ECD-Fc and Fc treatment groups in PR5 mouse brain, with (B) the expression ratio of BACE1/β-actin, and (C) sAPPβ/β-actin (n=5 per group, mean±SEM, Student's t-test; "Fc" was normalized to 100%)
Figure 15:
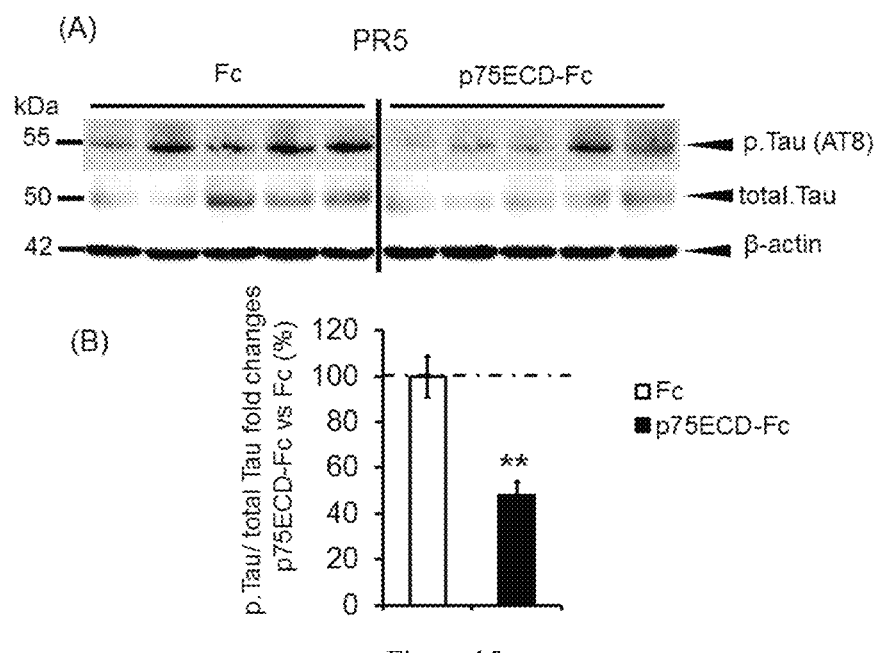
FIG. 15 provides results of A) Western blot image showing level of Tau phosphorylation at Ser202 and Thr205 (using a single "AT8" antibody) and total Tau in p75ECD-Fc and Fc treated PR5 mice brains, and (B) statistical analysis for phosphorylated Tau at Ser202 and Thr205 (**p<0.01 vs Fc) (n=5 per group, mean±SEM, Student's t-test; "Fc" was normalized to 100%).

In order to evaluate the effects of p75ECD-Fc on learning and memory functions in PR5 mice, twelve three-month-old mice were divided to two groups and received p75ECD-Fc or Fc recombinant proteins for 3 months. Wild type mice were tested in parallel. A group of age and sex matched wild type mice were used as control. Morris Water Maze (MWM) test for PR5 mice showed that p75ECD-Fc significantly reduced escape latency time (FIG. 13 A) during 2nd, 4th, and 5th day of learning trials and travel distance (FIGS. 13 B and C) during 2nd, 3rd, and 5th day of the learning trials in comparison with the Fc group. Learning process in wild type and p75ECD-Fc groups was improved. A significant reduction of escape latency and travel distance within day of 3rd, 4th, and 5th vs 1st were seen during learning process in Wild type group. In the p75ECD-Fc group the escape latency and travel distance were decreased within day of 4th and 5th vs 1st during learning process whereas no significant improvement of learning was seen in Fc group during learning process. However, p75ECD-Fc did not change the mean time in the target quadrant (FIG. 13 D), number of entries in the platform quadrants (FIG. 13 E) in the probe trial session. The number of crossings over the platform in the probe trial was unchanged between groups (FIG. 13 F). The results indicate that p75ECD-Fc could improve the process of learning in PR5 mouse.

p75ECD-Fc Reduced the Expression of BACE1 and sAPPβ Production in PR5 Mouse Brain In order to evaluate the effect of p75ECD-Fc on AD hallmarks in PR5 mouse, the brain lysate from both p75ECD-Fc and Fc treated groups were subjected to Western blot and incubated with different primary antibodies for measuring AD biomarkers proteins, BACE1, sAPPβ, and full length APP (APP.FL). The expression levels of BACE1 and sAPPβ in PR5 mouse brain in the Western blot data demonstrated that p75ECD-Fc significantly reduced BACE1 expression (p<0.05) (FIGS. 14 A and B). Further, it was observed that the levels of sAPPβ decreased in p75ECD-Fc treatment group compared to the Fc group in PR5 mice (FIGS. 14 A and C).

p75ECD-Fc Inhibited Tau Phosphorylation (p. Ser202 and Thr205) in PR5 Mouse Brain To test whether p75ECD-Fc inhibits Tau phosphorylation in PR5 mouse, the brain lysate from PR5 mice treated with either p75ECD-Fc or Fc was subjected to Western blot analysis in order to detect Tau-phosphorylated protein using mouse phosphor-PHF-Tau pSer202+Thr205 monoclonal (AT8) antibody. Our data indicated that p75ECD-Fc significantly reduced Tau (Ser202 and Thr205) phosphorylation in PR5 mouse (p<0.01) (FIGS. 15 A and B).

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

REFERENCES

Castellani, R. J. & Perry, G. (2012) *Arch Med Res* 43: 694-698
Chakravarthy, B. et al. (2012) *J Alzheimer's disease*: JAD 30: 675-684
Charidimou A, et al. (2012) *J Neurol Neurosurg Psychiatry* 83:124-37.
Conrad, C. D et al. (1999) *Neurobiol of learning and memory* 72: 39-46 (1999)
Dellu, F. et al. (1992) *Brain Res* 588: 132-139
Detters et al., (2008) *Eur J Neurosci.* 28(1): 137-47
Food and Drug Administration (2003) *Fed Regist* 68:2340-2341
Gotz et al. (2001) *Science* 293(5534):1491-5
Jellinger K A. (2002) *J Neural Transm* 109: 813
Jung, W. R et al. (2008) *Neurosci Lett* 439, 220-225
Keage H A et al. (2009) *BMC Neurol* 9: 3.
Kommaddi, R. P. et al. (2011) *FASEB J* 25: 2061-2070
Markowska A. L et al. (1993) *Behavioral Neurosci* 107: 627-632.
McKhann G. et al. (1984) *Neurology* 34: 939-944.
Rafii, M. S. (2013) *Reviews on Recent Clinical Trials* 8: 110-118
Saadipour, K. et al. (2013) *J Neurochem* 127: 152-162
Sarter M. et al. (1988) *Psychopharmacology* 94: 491-495
Schor, N. F. (2005). *Prog Neurobiol* 77(3): 201-214
Urra, S. et al. (2007) *J Biol Chem* 282: 7606-7615
Wang, Y. J. et al. (2009a) *Neurotoxicity Res* 15: 3-14
Wang Y. J. et al. (2009b) *Neurobiology of Aging* 30: 364-376
Wang Y. J. et al. (2010) *Brain, Behavior, and Immunity* 24: 1281-1293
Wang, Y. J. et al. (2011) *J Neurosci* 31: 2292-2304
Weskamp, G. et al. (2004) *J Biol Chem* 279: 4241-4249.
Yau J. L. et al. (2007) *J Neurosci.* 27: 10487-10496
Zhou L et al (2013) *J Affect Disorder* 150: 776-784

What is claimed is:

1. A method of treating cerebral amyloid angiopathy (CAA) in a human, comprising administering to a human in need thereof, a therapeutically-effective amount of a pharmaceutical formulation comprising: (a) an isolated p75 extracellular domain (p75ECD) peptide that consists of the sequence of SEQ ID NO:4; (b) an isolated p75ECD-Fc fusion protein that consists of the amino acid sequence of SEQ ID NO:6; or (c) a combination thereof, in an amount and for a time effective to treat the CAA in the human.

2. The method of claim 1, wherein the isolated p75ECD peptide or the isolated p75ECD-Fc fusion protein is a recombinant peptide.

3. The method of claim 2, wherein the isolated p75ECD peptide or the isolated p75ECD-Fc fusion protein is administered via one or more of intraperitoneal, intraventricular, intravenous, intrathecal, and intramuscular injections.

4. The method of claim 3, wherein the isolated p75ECD peptide or the isolated p75ECD-Fc fusion protein is administered at a dosage of between about 0.1 mg/kg and about 250 mg/kg of body weight.

* * * * *